(12) United States Patent (10) Patent No.: US 12,630,807 B2
Yoshida (45) Date of Patent: May 19, 2026

(54) MODIFIED TRANSGLUTAMINASE

(71) Applicant: AMANO ENZYME INC., Nagoya (JP)

(72) Inventor: Kazunori Yoshida, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 0 days.

(21) Appl. No.: 18/212,427

(22) Filed: Jun. 21, 2023

(65) Prior Publication Data

US 2024/0052323 A1 Feb. 15, 2024

Related U.S. Application Data

(62) Division of application No. 16/763,779, filed as application No. PCT/JP2018/043292 on Nov. 22, 2018, now abandoned.

(30) Foreign Application Priority Data

Nov. 30, 2017 (JP) ................................. 2017-231192

(51) Int. Cl.
*C12N 9/10* (2006.01)

(52) U.S. Cl.
CPC .... *C12N 9/1044* (2013.01); *C12Y 203/02013* (2013.01)

(58) Field of Classification Search
None
See application file for complete search history.

(56) References Cited

U.S. PATENT DOCUMENTS

| | | |
|---|---|---|
| 2003/0113407 A1 | 6/2003 | Lin et al. |
| 2009/0117640 A1 | 5/2009 | Norskov-Lauritsen et al. |
| 2009/0318349 A1 | 12/2009 | Hu et al. |
| 2010/0087371 A1 | 4/2010 | Hu et al. |
| 2010/0099610 A1 | 4/2010 | Hu et al. |
| 2010/0143970 A1 | 6/2010 | Yokoyama et al. |
| 2012/0021458 A1 | 1/2012 | Suzuki et al. |

FOREIGN PATENT DOCUMENTS

| | | |
|---|---|---|
| CN | 101126097 A | 2/2008 |
| CN | 101287757 A | 10/2008 |
| CN | 101631860 A | 1/2010 |
| CN | 102719411 A | 10/2012 |
| EP | 1310560 A1 | 5/2003 |

| | | |
|---|---|---|
| JP | H04-108381 A | 4/1992 |
| JP | 2002-253272 A | 9/2002 |
| JP | 2008-194004 A | 8/2008 |
| WO | 2010/101256 A1 | 9/2010 |
| WO | 2017-059160 A1 | 4/2017 |

OTHER PUBLICATIONS

C. K. Marx et al., "Random mutagenesis of a recombinant microbial transglutaminase for the generation of thermostable and heat-sensitive variants ," J Biotechnology, 2008, 136(3-4), pp. 156-162. (discussed in the spec).
U. Tagami et al., "Substrate specificity of microbial transglutaminase as revealed by three-dimensional docking simulation and mutagenesis," Protein Eng Design & Selections, 2009, 22(12), pp. 747-752. (discussed in the spec).
K. Yokoyama et al., "Screening for improved activity of a transglutaminase from *Streptomyces mobaraensis* created by a novel rational mutagenesis and random mutagenesis," Appl Microbiol Biotechnol, 2010, 87, pp. 2087-2096. (discussed in the spec).
K. Buettner et al., "Increased thermostability of microbial transglutaminase by combination of several hot spots evolved by random and saturation mutagenesis," Amino Acids, 2012, 42(2-3), pp. 987-996. (discussed in the spec).
International Search Report mailed Feb. 26, 2019, issued for PCT/JP2018/043292.
Supplementary European Search Report dated Aug. 2, 2021, issued for Counterpart European Patent Appln.No. 18883947.6.
Kashiwagi, T., et al. 2002 The Journal of Biological Chemistry 277(46): 44252-44260. (Year: 2002).
David A. Estell et al., "Engineering an Enzyme by Site-directed Mutagenesis to Be Resistant to Chemical Oxidation," The Journal of Biological Chemistry, vol. 260, No. 11, Issue of Jun. 10, 1985, pp. 6518-6521.
Yun Ho Kim et al. "Comparing the effect on protein stability of methionine oxidation versus mutagenesis: steps toward engineering oxidative resistance in proteins," Protein Engineering vol. 14 No. 5, 2001, pp. 343-347.
Office Action dated Mar. 6, 2025, issued for Counterpart Brazilian Patent Appln. No. 11 2020 009793 4.

*Primary Examiner* — Marsha Tsay
(74) *Attorney, Agent, or Firm* — Troutman Pepper Locke LLP

(57) ABSTRACT

An object of the present invention is to find a new mutation effective for improving transglutaminase, and to provide a highly useful modified transglutaminase. Disclosed is a highly useful modified transglutaminase having an amino acid substitution that results in a reduction in temperature stability, an improvement in heat resistance, an improvement in oxidation resistance, an improvement in reactivity, or conversion into deamidase.

9 Claims, 25 Drawing Sheets

Specification includes a Sequence Listing.

Mutation point V6

| Amino acid after substitution | TG activity (untreated) U/mL | TG activity (50°C, 30 min.) U/mL | Residual activity rate % | Rate relative to wild type % |
|---|---|---|---|---|
| Wild type | 15.8 | 6.4 | 41 | 100% |
| Gln | 14.2 | 3.2 | 23 | 55% |
| Ile | 11.8 | 2.3 | 20 | 49% |
| Met | 12.9 | 2.2 | 17 | 43% |
| Ser | 16.6 | 2.0 | 12 | 30% |
| Cys | 7.6 | 0.8 | 10 | 25% |
| Lys | 13.1 | 0.9 | 7 | 18% |
| Leu | 12.9 | 0.8 | 7 | 16% |
| His | 11.3 | 0.3 | 2 | 6% |
| Phe | 5.8 | 0.0 | 0 | 0% |
| Gly | 12.5 | 0.0 | 0 | 0% |
| Asn | 10.9 | 0.0 | 0 | 0% |
| Pro | 3.7 | 0.0 | 0 | 0% |
| Arg | 5.9 | 0.0 | 0 | 0% |
| Trp | 8.0 | 0.0 | 0 | 0% |
| Tyr | 6.1 | 0.0 | 0 | 0% |

Mutation point R26

| Amino acid after substitution | TG activity (untreated) U/mL | TG activity (50°C, 30 min.) U/mL | Residual activity rate % | Rate relative to wild type % |
|---|---|---|---|---|
| Wild type | 15.0 | 11.4 | 76 | 100% |
| Lys | 13.7 | 4.7 | 34 | 45% |
| Gln | 11.9 | 2.9 | 24 | 32% |
| Met | 15.4 | 3.4 | 22 | 29% |
| His | 14.8 | 0.3 | 2 | 3% |
| Tyr | 10.6 | 0.1 | 1 | 2% |
| Asp | 7.0 | 0.0 | 0 | 0% |
| Gly | 4.5 | 0.0 | 0 | 0% |
| Asn | 12.3 | 0.0 | 0 | 0% |
| Pro | 4.6 | 0.0 | 0 | 0% |
| Ser | 9.8 | 0.0 | 0 | 0% |

Mutation point E28

| Amino acid after substitution | TG activity (untreated) U/mL | TG activity (50°C, 30 min.) U/mL | Residual activity rate % | Rate relative to wild type % |
|---|---|---|---|---|
| Wild type | 11.4 | 4.7 | 41 | 100% |
| Val | 10.6 | 3.3 | 32 | 77% |
| Gln | 11.2 | 2.9 | 26 | 62% |
| Trp | 10.1 | 2.2 | 22 | 54% |
| Arg | 7.5 | 1.5 | 20 | 49% |
| Lys | 10.5 | 2.0 | 19 | 46% |
| Met | 10.4 | 1.5 | 14 | 35% |
| Asn | 8.7 | 0.6 | 7 | 17% |
| Phe | 8.3 | 0.3 | 4 | 9% |
| Gly | 10.7 | 0.2 | 2 | 4% |
| Leu | 8.5 | 0.0 | 0 | 0% |
| Pro | 1.2 | 0.0 | 0 | 0% |
| Tyr | 8.3 | 0.0 | 0 | 0% |

*Fig. 1-1*

Mutation point V30

| Amino acid after substitution | TG activity (untreated) U/mL | TG activity (50°C, 30 min.) U/mL | Residual activity rate % | Rate relative to wild type % |
|---|---|---|---|---|
| Wild type | 9.4 | 3.3 | 35 | 100% |
| Pro | 10.8 | 1.1 | 10 | 28% |
| Cys | 9.5 | 0.1 | 1 | 2% |
| Ala | 7.3 | 0.0 | 0 | 0% |
| Glu | 8.8 | 0.0 | 0 | 0% |
| Phe | 7.2 | 0.0 | 0 | 0% |
| Gly | 10.0 | 0.0 | 0 | 0% |
| His | 9.3 | 0.0 | 0 | 0% |
| Lys | 9.2 | 0.0 | 0 | 0% |
| Asn | 10.5 | 0.0 | 0 | 0% |
| Gln | 8.3 | 0.0 | 0 | 0% |
| Arg | 9.8 | 0.0 | 0 | 0% |
| Trp | 6.8 | 0.0 | 0 | 0% |
| Tyr | 10.2 | 0.0 | 0 | 0% |
| Leu | 9.0 | 0.0 | 0 | 0% |

Mutation point Y34

| Amino acid after substitution | TG activity (untreated) U/mL | TG activity (50°C, 30 min.) U/mL | Residual activity rate % | Rate relative to wild type % |
|---|---|---|---|---|
| Wild type | 18.8 | 6.8 | 36 | 100% |
| Ala | 0.9 | 0.0 | 0 | 0% |

Mutation point Y42

| Amino acid after substitution | TG activity (untreated) U/mL | TG activity (50°C, 30 min.) U/mL | Residual activity rate % | Rate relative to wild type % |
|---|---|---|---|---|
| Wild type | 15.3 | 5.6 | 37 | 100% |
| Phe | 7.6 | 1.8 | 23 | 64% |
| Ala | 3.9 | 0.0 | 0 | 0% |
| Cys | 12.4 | 0.0 | 0 | 0% |
| Asp | 2.0 | 0.0 | 0 | 0% |
| Glu | 4.6 | 0.0 | 0 | 0% |
| Gly | 1.9 | 0.0 | 0 | 0% |
| Ile | 2.1 | 0.0 | 0 | 0% |
| Leu | 11.9 | 0.0 | 0 | 0% |
| Met | 12.6 | 0.0 | 0 | 0% |
| Gln | 10.6 | 0.0 | 0 | 0% |
| Ser | 11.8 | 0.0 | 0 | 0% |
| Thr | 6.8 | 0.0 | 0 | 0% |
| Val | 5.1 | 0.0 | 0 | 0% |
| Trp | 9.5 | 0.0 | 0 | 0% |

Mutation point E58

| Amino acid after substitution | TG activity (untreated) U/mL | TG activity (50°C, 30 min.) U/mL | Residual activity rate % | Rate relative to wild type % |
|---|---|---|---|---|
| Wild type | 9.0 | 2.2 | 24 | 100% |
| Tyr | 9.0 | 1.7 | 19 | 78% |
| Met | 9.5 | 1.7 | 18 | 76% |
| Ala | 10.0 | 1.4 | 14 | 58% |
| Phe | 9.5 | 1.1 | 12 | 48% |
| Ile | 10.8 | 1.2 | 11 | 45% |
| Val | 10.8 | 1.1 | 11 | 44% |
| Arg | 8.0 | 0.8 | 10 | 42% |
| Lys | 8.6 | 0.9 | 10 | 42% |
| Asn | 9.8 | 0.9 | 9 | 37% |
| Leu | 10.5 | 0.8 | 8 | 32% |
| Ser | 9.5 | 0.7 | 8 | 32% |
| Gln | 10.0 | 0.7 | 7 | 31% |
| Gly | 9.4 | 0.5 | 5 | 21% |
| His | 8.8 | 0.3 | 3 | 14% |

*Fig. 1-2*

Mutation point W59

| Amino acid after substitution | TG activity (untreated) U/mL | TG activity (50°C, 30 min.) U/mL | Residual activity rate % | Rate relative to wild type % |
|---|---|---|---|---|
| Wild type | 14.5 | 8.8 | 61 | 100% |
| Arg | 10.8 | 2.9 | 27 | 45% |
| Asn | 13.6 | 3.5 | 26 | 43% |
| Tyr | 14.0 | 2.8 | 20 | 33% |
| Ala | 13.9 | 2.6 | 19 | 30% |
| Ser | 12.4 | 1.5 | 12 | 20% |
| Ile | 12.3 | 0.6 | 5 | 8% |
| Val | 14.8 | 0.6 | 4 | 7% |
| Asp | 6.7 | 0.3 | 4 | 6% |
| Gly | 10.8 | 0.2 | 2 | 3% |
| Pro | 3.6 | 0.0 | 0 | 0% |

Mutation point L60

| Amino acid after substitution | TG activity (untreated) U/mL | TG activity (50°C, 30 min.) U/mL | Residual activity rate % | Rate relative to wild type % |
|---|---|---|---|---|
| Wild type | 20.3 | 8.7 | 43 | 100% |
| Ile | 21.6 | 6.9 | 32 | 74% |
| Met | 14.3 | 1.1 | 7 | 17% |
| Val | 20.6 | 0.8 | 4 | 10% |
| Ala | 9.6 | 0.2 | 2 | 4% |
| Cys | 18.2 | 0.0 | 0 | 0% |
| Glu | 7.5 | 0.0 | 0 | 0% |
| Phe | 14.9 | 0.0 | 0 | 0% |
| Gln | 4.0 | 0.0 | 0 | 0% |
| Ser | 3.5 | 0.0 | 0 | 0% |
| Thr | 10.0 | 0.0 | 0 | 0% |
| Trp | 2.1 | 0.0 | 0 | 0% |
| Tyr | 3.7 | 0.0 | 0 | 0% |

Mutation point Y62

| Amino acid after substitution | TG activity (untreated) U/mL | TG activity (50°C, 30 min.) U/mL | Residual activity rate % | Rate relative to wild type % |
|---|---|---|---|---|
| Wild type | 12.7 | 5.2 | 41 | 100% |
| Cys | 11.8 | 0.1 | 1 | 1% |
| Arg | 6.8 | 0.0 | 0 | 0% |
| Gly | 2.7 | 0.0 | 0 | 0% |
| Lys | 3.7 | 0.0 | 0 | 0% |
| Ser | 4.8 | 0.0 | 0 | 0% |

Mutation point V65

| Amino acid after substitution | TG activity (untreated) U/mL | TG activity (50°C, 30 min.) U/mL | Residual activity rate % | Rate relative to wild type % |
|---|---|---|---|---|
| Wild type | 17.6 | 7.7 | 43 | 100% |
| Asn | 1.2 | 0.1 | 9 | 20% |
| Leu | 9.8 | 0.9 | 9 | 20% |
| Met | 5.6 | 0.2 | 4 | 9% |
| Phe | 5.7 | 0.0 | 0 | 0% |
| Trp | 1.9 | 0.0 | 0 | 0% |
| Tyr | 1.5 | 0.0 | 0 | 0% |

Mutation point V67

| Amino acid after substitution | TG activity (untreated) U/mL | TG activity (50°C, 30 min.) U/mL | Residual activity rate % | Rate relative to wild type % |
|---|---|---|---|---|
| Wild type | 14.3 | 3.6 | 25 | 100% |
| Leu | 13.3 | 0.9 | 7 | 27% |
| Asn | 6.5 | 0.2 | 3 | 14% |
| Ala | 6.9 | 0.0 | 0 | 0% |
| Cys | 8.8 | 0.0 | 0 | 0% |
| Met | 8.2 | 0.0 | 0 | 0% |
| Gln | 1.4 | 0.0 | 0 | 0% |
| Ser | 2.8 | 0.0 | 0 | 0% |

*Fig. 1-3*

Mutation point T68

| Amino acid after substitution | TG activity (untreated) U/mL | TG activity (50°C, 30 min.) U/mL | Residual activity rate % | Rate relative to wild type % |
|---|---|---|---|---|
| Wild type | 18.3 | 8.5 | 46 | 100% |
| Cys | 11.2 | 4.6 | 41 | 89% |
| Leu | 3.4 | 0.9 | 26 | 56% |
| Ala | 9.2 | 2.3 | 25 | 55% |
| Ser | 12.3 | 2.5 | 20 | 44% |
| Met | 4.9 | 0.6 | 13 | 29% |
| Phe | 2.2 | 0.0 | 0 | 0% |
| Asn | 3.7 | 0.0 | 0 | 0% |
| Gln | 4.1 | 0.0 | 0 | 0% |
| Tyr | 1.1 | 0.0 | 0 | 0% |

Mutation point W69

| Amino acid after substitution | TG activity (untreated) U/mL | TG activity (50°C, 30 min.) U/mL | Residual activity rate % | Rate relative to wild type % |
|---|---|---|---|---|
| Wild type | 15.4 | 10.6 | 69 | 100% |
| His | 6.5 | 1.6 | 25 | 36% |
| Met | 12.7 | 0.7 | 5 | 8% |
| Ile | 8.3 | 0.1 | 1 | 1% |
| Cys | 8.3 | 0.0 | 0 | 0% |
| Glu | 1.4 | 0.0 | 0 | 0% |
| Phe | 9.5 | 0.0 | 0 | 0% |
| Gly | 3.4 | 0.0 | 0 | 0% |
| Lys | 3.2 | 0.0 | 0 | 0% |
| Leu | 9.1 | 0.0 | 0 | 0% |
| Asn | 1.4 | 0.0 | 0 | 0% |
| Gln | 3.8 | 0.0 | 0 | 0% |
| Arg | 4.8 | 0.0 | 0 | 0% |
| Ser | 5.6 | 0.0 | 0 | 0% |
| Thr | 9.3 | 0.0 | 0 | 0% |
| Val | 9.6 | 0.0 | 0 | 0% |

Mutation point Q74

| Amino acid after substitution | TG activity (untreated) U/mL | TG activity (50°C, 30 min.) U/mL | Residual activity rate % | Rate relative to wild type % |
|---|---|---|---|---|
| Wild type | 16.7 | 8.7 | 52 | 100% |
| Glu | 16.3 | 8.2 | 51 | 97% |
| Ile | 16.5 | 8.1 | 49 | 94% |
| Trp | 14.5 | 6.5 | 45 | 86% |
| Asp | 17.1 | 7.3 | 43 | 81% |
| Gly | 17.7 | 6.7 | 38 | 72% |
| Lys | 13.1 | 4.9 | 37 | 71% |

Mutation point Y75

| Amino acid after substitution | TG activity (untreated) U/mL | TG activity (50°C, 30 min.) U/mL | Residual activity rate % | Rate relative to wild type % |
|---|---|---|---|---|
| Wild type | 13.8 | 7.2 | 52 | 100% |
| Arg | 13.2 | 2.9 | 22 | 42% |
| Gln | 11.9 | 1.9 | 16 | 31% |
| Thr | 7.3 | 0.3 | 4 | 8% |
| Gly | 4.2 | 0.0 | 0 | 0% |

Mutation point T77

| Amino acid after substitution | TG activity (untreated) U/mL | TG activity (50°C, 30 min.) U/mL | Residual activity rate % | Rate relative to wild type % |
|---|---|---|---|---|
| Wild type | 14.8 | 7.8 | 53 | 100% |
| Arg | 11.8 | 6.1 | 52 | 98% |
| Lys | 10.8 | 5.2 | 48 | 91% |
| Asp | 14.0 | 6.7 | 48 | 91% |
| Met | 16.0 | 7.5 | 47 | 88% |
| His | 13.5 | 6.2 | 46 | 87% |
| Glu | 16.6 | 7.3 | 44 | 84% |
| Cys | 15.7 | 6.5 | 42 | 79% |
| Gly | 12.3 | 4.4 | 36 | 68% |

*Fig. 1-4*

Mutation point F85

| Amino acid after substitution | TG activity (untreated) U/mL | TG activity (50°C, 30 min.) U/mL | Residual activity rate % | Rate relative to wild type % |
|---|---|---|---|---|
| Wild type | 12.4 | 10.8 | 87 | 100% |
| Met | 2.5 | 0.6 | 22 | 26% |

Mutation point F90

| Amino acid after substitution | TG activity (untreated) U/mL | TG activity (50°C, 30 min.) U/mL | Residual activity rate % | Rate relative to wild type % |
|---|---|---|---|---|
| Wild type | 13.7 | 6.5 | 47 | 100% |
| Tyr | 13.4 | 6.1 | 45 | 95% |
| Cys | 5.9 | 2.4 | 41 | 86% |
| Met | 7.7 | 2.9 | 38 | 80% |
| His | 7.6 | 2.6 | 34 | 71% |
| Leu | 5.1 | 1.6 | 32 | 67% |
| Val | 1.9 | 0.2 | 9 | 18% |

Mutation point F108

| Amino acid after substitution | TG activity (untreated) U/mL | TG activity (50°C, 30 min.) U/mL | Residual activity rate % | Rate relative to wild type % |
|---|---|---|---|---|
| Wild type | 24.2 | 13.7 | 57 | 100% |
| Arg | 7.1 | 1.9 | 26 | 46% |
| Leu | 5.4 | 1.2 | 22 | 40% |
| Thr | 4.0 | 0.6 | 14 | 24% |
| Ala | 1.3 | 0.0 | 0 | 0% |
| Ile | 1.5 | 0.0 | 0 | 0% |
| Lys | 1.9 | 0.0 | 0 | 0% |
| Asn | 0.9 | 0.0 | 0 | 0% |
| Val | 1.9 | 0.0 | 0 | 0% |

Mutation point F117

| Amino acid after substitution | TG activity (untreated) U/mL | TG activity (50°C, 30 min.) U/mL | Residual activity rate % | Rate relative to wild type % |
|---|---|---|---|---|
| Wild type | 21.4 | 12.2 | 57 | 100% |
| Met | 3.7 | 0.8 | 23 | 40% |
| Leu | 1.4 | 0.0 | 0 | 0% |

Mutation point S199

| Amino acid after substitution | TG activity (untreated) U/mL | TG activity (50°C, 30 min.) U/mL | Residual activity rate % | Rate relative to wild type % |
|---|---|---|---|---|
| Wild type | 16.5 | 6.9 | 42 | 100% |
| Gly | 17.7 | 6.3 | 36 | 86% |
| Met | 6.5 | 2.2 | 34 | 82% |
| Asn | 1.1 | 0.3 | 30 | 72% |
| Lys | 1.9 | 0.2 | 8 | 20% |
| Val | 3.9 | 0.2 | 6 | 15% |

Mutation point F202

| Amino acid after substitution | TG activity (untreated) U/mL | TG activity (50°C, 30 min.) U/mL | Residual activity rate % | Rate relative to wild type % |
|---|---|---|---|---|
| Wild type | 19.9 | 9.9 | 50 | 100% |
| Leu | 2.7 | 0.6 | 23 | 46% |
| Trp | 1.2 | 0.0 | 0 | 0% |

Mutation point W203X

| Amino acid after substitution | TG activity (untreated) U/mL | TG activity (50°C, 30 min.) U/mL | Residual activity rate % | Rate relative to wild type % |
|---|---|---|---|---|
| Wild type | 19.6 | 11.2 | 57 | 100% |
| Phe | 3.8 | 1.2 | 32 | 55% |

*Fig. 1-5*

Mutation point F254

| Amino acid after substitution | TG activity (untreated) U/mL | TG activity (50°C, 30 min.) U/mL | Residual activity rate % | Rate relative to wild type % |
|---|---|---|---|---|
| Wild type | 20.6 | 9.5 | 46 | 100% |
| Tyr | 8.3 | 3.0 | 37 | 80% |
| Met | 2.7 | 0.6 | 21 | 45% |

Mutation point T273

| Amino acid after substitution | TG activity (untreated) U/mL | TG activity (50°C, 30 min.) U/mL | Residual activity rate % | Rate relative to wild type % |
|---|---|---|---|---|
| Wild type | 16.0 | 7.5 | 47 | 100% |
| Ile | 10.1 | 3.6 | 36 | 76% |
| Val | 12.5 | 4.3 | 34 | 74% |
| Met | 12.2 | 3.1 | 25 | 54% |
| Cys | 11.9 | 2.5 | 21 | 46% |
| Ser | 9.0 | 1.7 | 19 | 40% |
| Leu | 11.6 | 1.5 | 13 | 27% |
| Arg | 5.7 | 0.6 | 11 | 24% |
| Gly | 2.3 | 0.2 | 10 | 21% |
| Ala | 9.9 | 0.6 | 6 | 13% |
| Glu | 4.4 | 0.2 | 6 | 12% |
| Phe | 12.3 | 0.3 | 2 | 5% |
| Tyr | 12.7 | 0.1 | 1 | 1% |
| Asp | 1.2 | 0.0 | 0 | 0% |
| Lys | 1.2 | 0.0 | 0 | 0% |
| Trp | 6.5 | 0.0 | 0 | 0% |
| His | 9.1 | 0.0 | 0 | 0% |

Mutation point N276

| Amino acid after substitution | TG activity (untreated) U/mL | TG activity (50°C, 30 min.) U/mL | Residual activity rate % | Rate relative to wild type % |
|---|---|---|---|---|
| Wild type | 22.6 | 10.8 | 48 | 100% |
| Asp | 9.8 | 4.6 | 47 | 98% |
| Cys | 2.5 | 0.0 | 0 | 0% |
| Glu | 1.1 | 0.0 | 0 | 0% |
| Lys | 2.8 | 0.0 | 0 | 0% |
| Leu | 1.8 | 0.0 | 0 | 0% |
| Thr | 9.0 | 0.0 | 0 | 0% |
| Val | 1.5 | 0.0 | 0 | 0% |
| Ser | 10.1 | 0.0 | 0 | 0% |

Mutation point Y278

| Amino acid after substitution | TG activity (untreated) U/mL | TG activity (50°C, 30 min.) U/mL | Residual activity rate % | Rate relative to wild type % |
|---|---|---|---|---|
| Wild type | 18.2 | 9.8 | 54 | 100% |
| Met | 15.6 | 2.7 | 17 | 32% |
| Leu | 15.7 | 2.2 | 14 | 27% |
| His | 5.2 | 0.7 | 13 | 23% |
| Ile | 7.7 | 0.8 | 11 | 20% |
| Lys | 5.9 | 0.3 | 5 | 10% |
| Arg | 6.9 | 0.2 | 3 | 6% |
| Trp | 15.6 | 0.3 | 2 | 4% |
| Cys | 4.1 | 0.0 | 0 | 0% |
| Gly | 2.7 | 0.0 | 0 | 0% |
| Asn | 1.4 | 0.0 | 0 | 0% |
| Gln | 7.1 | 0.0 | 0 | 0% |
| Ser | 2.6 | 0.0 | 0 | 0% |
| Thr | 1.8 | 0.0 | 0 | 0% |
| Val | 3.8 | 0.0 | 0 | 0% |

*Fig. 1-6*

Mutation point S284

| Amino acid after substitution | TG activity (untreated) U/mL | TG activity (50°C, 30 min.) U/mL | Residual activity rate % | Rate relative to wild type % |
|---|---|---|---|---|
| Wild type | 14.7 | 5.0 | 34 | 100% |
| Trp | 13.6 | 3.9 | 29 | 85% |
| Tyr | 15.3 | 4.4 | 28 | 84% |
| Met | 15.4 | 4.1 | 27 | 79% |
| Phe | 16.1 | 4.0 | 25 | 73% |
| Asn | 13.9 | 3.0 | 21 | 63% |

Mutation point Y291

| Amino acid after substitution | TG activity (untreated) U/mL | TG activity (50°C, 30 min.) U/mL | Residual activity rate % | Rate relative to wild type % |
|---|---|---|---|---|
| Wild type | 14.4 | 5.2 | 36 | 100% |
| Phe | 12.0 | 4.3 | 36 | 99% |
| Ile | 8.3 | 0.9 | 11 | 30% |
| Trp | 3.8 | 0.2 | 5 | 14% |
| Leu | 8.7 | 0.3 | 3 | 9% |
| Ala | 3.9 | 0.0 | 0 | 0% |
| Cys | 3.9 | 0.0 | 0 | 0% |
| Lys | 10.9 | 0.0 | 0 | 0% |
| Asn | 4.7 | 0.0 | 0 | 0% |
| Gln | 2.4 | 0.0 | 0 | 0% |
| Arg | 10.7 | 0.0 | 0 | 0% |
| Ser | 3.7 | 0.0 | 0 | 0% |
| Val | 6.0 | 0.0 | 0 | 0% |

Mutation point S299

| Amino acid after substitution | TG activity (untreated) U/mL | TG activity (50°C, 30 min.) U/mL | Residual activity rate % | Rate relative to wild type % |
|---|---|---|---|---|
| Wild type | 13.1 | 5.1 | 39 | 100% |
| Thr | 13.4 | 5.3 | 39 | 99% |
| Arg | 13.5 | 5.3 | 39 | 99% |
| His | 10.2 | 3.7 | 36 | 91% |
| Ile | 14.9 | 5.2 | 35 | 89% |
| Tyr | 10.3 | 3.5 | 34 | 86% |
| Val | 13.7 | 4.5 | 33 | 84% |
| Lys | 13.0 | 4.2 | 32 | 82% |
| Met | 14.6 | 4.6 | 32 | 81% |
| Gln | 13.3 | 4.2 | 31 | 80% |
| Ala | 13.6 | 4.2 | 31 | 79% |
| Phe | 10.2 | 2.6 | 25 | 63% |
| Gly | 8.0 | 1.5 | 19 | 49% |
| Glu | 1.7 | 0.0 | 0 | 0% |

Mutation point S303

| Amino acid after substitution | TG activity (untreated) U/mL | TG activity (50°C, 30 min.) U/mL | Residual activity rate % | Rate relative to wild type % |
|---|---|---|---|---|
| Wild type | 14.5 | 6.4 | 44 | 100% |
| Trp | 9.1 | 3.7 | 40 | 91% |
| Met | 13.5 | 5.4 | 40 | 91% |
| Asn | 12.3 | 4.9 | 40 | 90% |
| Gly | 8.5 | 3.3 | 39 | 88% |
| Cys | 11.5 | 4.3 | 37 | 84% |
| Val | 13.1 | 4.8 | 37 | 83% |
| Pro | 7.0 | 2.3 | 34 | 76% |
| Tyr | 11.0 | 3.6 | 33 | 75% |

Mutation point Y310

| Amino acid after substitution | TG activity (untreated) U/mL | TG activity (50°C, 30 min.) U/mL | Residual activity rate % | Rate relative to wild type % |
|---|---|---|---|---|
| Wild type | 19.1 | 10.1 | 53 | 100% |
| Cys | 1.2 | 0.5 | 37 | 70% |
| Met | 2.2 | 0.7 | 31 | 58% |
| Ile | 1.0 | 0.2 | 15 | 29% |

Fig. 1-7

Mutation point D3

| Amino acid after substitution | TG activity (untreated) U/mL | TG activity (50°C, 30 min.) U/mL | Residual activity rate % | Rate relative to wild type % |
|---|---|---|---|---|
| Wild type | 17.6 | 6.6 | 38 | 100% |
| Gly | 18.2 | 7.2 | 40 | 106% |
| Gln | 15.4 | 6.4 | 41 | 110% |
| Pro | 25.9 | 11.7 | 45 | 120% |
| Glu | 17.3 | 8.5 | 49 | 131% |
| Ser | 16.8 | 9.0 | 54 | 143% |
| Tyr | 11.3 | 6.9 | 60 | 161% |

Mutation point R26

| Amino acid after substitution | TG activity (untreated) U/mL | TG activity (50°C, 30 min.) U/mL | Residual activity rate % | Rate relative to wild type % |
|---|---|---|---|---|
| Wild type | 15.0 | 11.4 | 76 | 100% |
| Val | 9.5 | 11.4 | 120 | 159% |

Mutation point Y34

| Amino acid after substitution | TG activity (untreated) U/mL | TG activity (50°C, 30 min.) U/mL | Residual activity rate % | Rate relative to wild type % |
|---|---|---|---|---|
| Wild type | 18.8 | 6.8 | 36 | 100% |
| Trp | 18.7 | 11.3 | 61 | 169% |

Mutation point V67

| Amino acid after substitution | TG activity (untreated) U/mL | TG activity (50°C, 30 min.) U/mL | Residual activity rate % | Rate relative to wild type % |
|---|---|---|---|---|
| Wild type | 14.3 | 3.6 | 25 | 100% |
| His | 1.9 | 1.8 | 90 | 361% |

Mutation point T68

| Amino acid after substitution | TG activity (untreated) U/mL | TG activity (50°C, 30 min.) U/mL | Residual activity rate % | Rate relative to wild type % |
|---|---|---|---|---|
| Wild type | 18.3 | 8.5 | 46 | 100% |
| Val | 8.0 | 4.3 | 54 | 116% |
| Ile | 4.1 | 2.3 | 55 | 119% |

Mutation point Q74

| Amino acid after substitution | TG activity (untreated) U/mL | TG activity (50°C, 30 min.) U/mL | Residual activity rate % | Rate relative to wild type % |
|---|---|---|---|---|
| Wild type | 16.7 | 8.7 | 52 | 100% |
| Thr | 19.1 | 10.7 | 56 | 107% |
| Phe | 16.4 | 9.8 | 59 | 114% |

Mutation point T77

| Amino acid after substitution | TG activity (untreated) U/mL | TG activity (50°C, 30 min.) U/mL | Residual activity rate % | Rate relative to wild type % |
|---|---|---|---|---|
| Wild type | 14.8 | 7.8 | 53 | 100% |
| Gln | 18.2 | 11.7 | 64 | 122% |

*Fig. 2-1*

Mutation point S199

| Amino acid after substitution | TG activity (untreated) U/mL | TG activity (50°C, 30 min.) U/mL | Residual activity rate % | Rate relative to wild type % |
|---|---|---|---|---|
| Wild type | 16.5 | 6.9 | 42 | 100% |
| Cys | 20.1 | 10.2 | 51 | 122% |
| Gln | 5.1 | 2.9 | 57 | 138% |

Mutation point T273

| Amino acid after substitution | TG activity (untreated) U/mL | TG activity (50°C, 30 min.) U/mL | Residual activity rate % | Rate relative to wild type % |
|---|---|---|---|---|
| Wild type | 16.0 | 7.5 | 47 | 100% |
| Gln | 11.7 | 7.1 | 61 | 130% |

Mutation point S284

| Amino acid after substitution | TG activity (untreated) U/mL | TG activity (50°C, 30 min.) U/mL | Residual activity rate % | Rate relative to wild type % |
|---|---|---|---|---|
| Wild type | 14.7 | 5.0 | 34 | 100% |
| Ile | 16.6 | 5.9 | 36 | 105% |
| Val | 16.8 | 6.2 | 37 | 109% |
| Leu | 16.1 | 6.1 | 38 | 112% |
| His | 11.0 | 5.6 | 50 | 149% |
| Lys | 15.6 | 8.3 | 53 | 158% |
| Pro | 15.6 | 8.7 | 56 | 164% |
| Arg | 15.9 | 9.3 | 59 | 173% |

Mutation point S299

| Amino acid after substitution | TG activity (untreated) U/mL | TG activity (50°C, 30 min.) U/mL | Residual activity rate % | Rate relative to wild type % |
|---|---|---|---|---|
| Wild type | 13.1 | 5.1 | 39 | 100% |
| Asn | 6.9 | 3.2 | 47 | 120% |

Mutation point S303

| Amino acid after substitution | TG activity (untreated) U/mL | TG activity (50°C, 30 min.) U/mL | Residual activity rate % | Rate relative to wild type % |
|---|---|---|---|---|
| Wild type | 14.5 | 6.4 | 44 | 100% |
| Arg | 13.6 | 6.5 | 48 | 108% |
| Leu | 13.0 | 6.3 | 48 | 109% |
| Lys | 14.2 | 8.0 | 56 | 128% |

*Fig. 2-2*

Mutation point D3

| Amino acid after substitution | TG activity (untreated) U/mL | TG activity (H$_2$O$_2$) U/mL | Residual activity rate % | Rate relative to wild type % |
|---|---|---|---|---|
| Wild type | 21 | 12 | 57 | 100% |
| Glu | 23 | 15 | 66 | 117% |
| Gln | 20 | 14 | 67 | 118% |
| Ser | 21 | 14 | 69 | 122% |
| Tyr | 14 | 10 | 74 | 130% |

Mutation point V6

| Amino acid after substitution | TG activity (untreated) U/mL | TG activity (H$_2$O$_2$) U/mL | Residual activity rate % | Rate relative to wild type % |
|---|---|---|---|---|
| Wild type | 18 | 5 | 25 | 100% |
| Pro | 4 | 2 | 47 | 191% |

Mutation point R26

| Amino acid after substitution | TG activity (untreated) U/mL | TG activity (H$_2$O$_2$) U/mL | Residual activity rate % | Rate relative to wild type % |
|---|---|---|---|---|
| Wild type | 21 | 12 | 57 | 100% |
| His | 22 | 14 | 62 | 109% |
| Met | 21 | 15 | 68 | 118% |
| Lys | 18 | 12 | 68 | 120% |
| Trp | 16 | 11 | 70 | 122% |
| Cys | 21 | 15 | 75 | 130% |
| Gln | 16 | 12 | 77 | 135% |
| Gly | 6 | 5 | 78 | 137% |
| Tyr | 17 | 14 | 80 | 139% |
| Glu | 12 | 10 | 82 | 143% |
| Thr | 18 | 15 | 82 | 143% |
| Asn | 15 | 13 | 83 | 145% |
| Asp | 9 | 8 | 85 | 148% |
| Ile | 11 | 10 | 90 | 157% |
| Ser | 14 | 13 | 90 | 157% |
| Pro | 7 | 6 | 90 | 158% |
| Val | 14 | 13 | 90 | 158% |

Mutation point E28

| Amino acid after substitution | TG activity (untreated) U/mL | TG activity (H$_2$O$_2$) U/mL | Residual activity rate % | Rate relative to wild type % |
|---|---|---|---|---|
| Wild type | 18 | 4 | 22 | 100% |
| Leu | 13 | 3 | 27 | 121% |
| Met | 14 | 4 | 27 | 121% |
| Lys | 13 | 4 | 27 | 122% |
| Cys | 14 | 4 | 29 | 130% |
| Val | 15 | 5 | 29 | 131% |
| Arg | 14 | 5 | 36 | 158% |
| Trp | 15 | 5 | 36 | 161% |
| Gly | 16 | 7 | 45 | 201% |
| Asn | 13 | 6 | 46 | 205% |
| Phe | 11 | 6 | 51 | 226% |
| Tyr | 11 | 6 | 51 | 228% |
| His | 8 | 4 | 57 | 252% |

*Fig. 3-1*

Mutation point Y42

| Amino acid after substitution | TG activity (untreated) U/mL | TG activity (H$_2$O$_2$) U/mL | Residual activity rate % | Rate relative to wild type % |
|---|---|---|---|---|
| Wild type | 20 | 8 | 40 | 100% |
| Met | 17 | 7 | 44 | 109% |
| Leu | 16 | 7 | 46 | 115% |
| Asn | 16 | 8 | 47 | 116% |
| Phe | 19 | 10 | 53 | 131% |

Mutation point E58

| Amino acid after substitution | TG activity (untreated) U/mL | TG activity (H$_2$O$_2$) U/mL | Residual activity rate % | Rate relative to wild type % |
|---|---|---|---|---|
| Wild type | 17 | 4 | 23 | 100% |
| Gln | 15 | 4 | 27 | 116% |
| Ala | 16 | 4 | 29 | 123% |
| Ile | 17 | 5 | 31 | 133% |
| Val | 17 | 6 | 33 | 140% |
| Leu | 15 | 5 | 33 | 143% |
| Thr | 16 | 6 | 35 | 148% |
| Met | 15 | 5 | 35 | 151% |
| Lys | 12 | 5 | 39 | 167% |
| Tyr | 14 | 6 | 41 | 174% |
| Trp | 15 | 7 | 45 | 192% |
| Phe | 16 | 7 | 47 | 200% |
| Arg | 13 | 6 | 48 | 207% |

Mutation point V67

| Amino acid after substitution | TG activity (untreated) U/mL | TG activity (H$_2$O$_2$) U/mL | Residual activity rate % | Rate relative to wild type % |
|---|---|---|---|---|
| Wild type | 24 | 15 | 62 | 100% |
| Thr | 2 | 1 | 73 | 118% |
| Ser | 2 | 2 | 76 | 122% |
| Ala | 7 | 5 | 78 | 125% |

Mutation point T68

| Amino acid after substitution | TG activity (untreated) U/mL | TG activity (H$_2$O$_2$) U/mL | Residual activity rate % | Rate relative to wild type % |
|---|---|---|---|---|
| Wild type | 22 | 14 | 65 | 100% |
| Cys | 13 | 9 | 70 | 107% |
| Leu | 3 | 3 | 77 | 118% |
| Ile | 4 | 3 | 84 | 130% |
| Val | 10 | 8 | 85 | 131% |
| Met | 6 | 5 | 86 | 133% |

Mutation point Q74

| Amino acid after substitution | TG activity (untreated) U/mL | TG activity (H$_2$O$_2$) U/mL | Residual activity rate % | Rate relative to wild type % |
|---|---|---|---|---|
| Wild type | 20 | 10 | 53 | 100% |
| Val | 23 | 14 | 62 | 118% |

*Fig. 3-2*

Mutation point T77

| Amino acid after substitution | TG activity (untreated) U/mL | TG activity (H₂O₂) U/mL | Residual activity rate % | Rate relative to wild type % |
|---|---|---|---|---|
| Wild type | 20 | 11 | 55 | 100% |
| Cys | 21 | 12 | 60 | 108% |
| Arg | 16 | 10 | 61 | 110% |
| Asp | 23 | 14 | 61 | 111% |

Mutation point S199

| Amino acid after substitution | TG activity (untreated) U/mL | TG activity (H₂O₂) U/mL | Residual activity rate % | Rate relative to wild type % |
|---|---|---|---|---|
| Wild type | 15 | 7 | 47 | 100% |
| Cys | 24 | 14 | 56 | 120% |

Mutation point T273

| Amino acid after substitution | TG activity (untreated) U/mL | TG activity (H₂O₂) U/mL | Residual activity rate % | Rate relative to wild type % |
|---|---|---|---|---|
| Wild type | 18 | 8 | 44 | 100% |
| Glu | 2 | 1 | 54 | 124% |

Mutation point S284

| Amino acid after substitution | TG activity (untreated) U/mL | TG activity (H₂O₂) U/mL | Residual activity rate % | Rate relative to wild type % |
|---|---|---|---|---|
| Wild type | 17 | 8 | 48 | 100% |
| Arg | 18 | 11 | 61 | 127% |
| His | 13 | 8 | 64 | 134% |

Mutation point Y291

| Amino acid after substitution | TG activity (untreated) U/mL | TG activity (H₂O₂) U/mL | Residual activity rate % | Rate relative to wild type % |
|---|---|---|---|---|
| Wild type | 25 | 15 | 60 | 100% |
| Ile | 13 | 9 | 67 | 110% |
| Ser | 4 | 3 | 69 | 114% |
| Phe | 17 | 12 | 71 | 118% |
| Leu | 15 | 11 | 72 | 120% |
| Cys | 5 | 4 | 74 | 122% |
| Asn | 5 | 3 | 75 | 124% |
| Val | 10 | 7 | 76 | 126% |
| Met | 13 | 10 | 77 | 128% |

*Fig. 3-3*

Mutation point S284

| Amino acid after substitution | TG activity U/mL | Rate relative to wild type % |
|---|---|---|
| Wild type | 17.2 | 100% |
| Leu | 18.6 | 108% |
| Ile | 18.7 | 109% |
| Phe | 18.8 | 109% |
| Met | 19.2 | 112% |
| Lys | 19.3 | 112% |
| Val | 22.1 | 128% |

Mutation point F251

| Amino acid after substitution | TG activity U/mL | Rate relative to wild type % |
|---|---|---|
| Wild type | 12.4 | 100% |
| Tyr | 15.8 | 128% |

Mutation point V6, Y75

| | TG activity U/mL | Rate relative to wild type % |
|---|---|---|
| Wild type | 12.7 | 100% |
| Variant V6E | 11.9 | 94% |
| Variant Y75F | 16.9 | 133% |
| Double Variant V6E/Y75F | 31.5 | 248% |

Mutation point D3, T77

| | TG activity U/mL | Rate relative to wild type % |
|---|---|---|
| Wild type | 12.7 | 100% |
| Variant D3P | 17.6 | 139% |
| Variant T77Q | 5.9 | 46% |
| Double Variant D3P/T77Q | 28.5 | 224% |

*Fig. 4*

Mutation point D3

| Amino acid after substitution | Reduction in temperature stability | Improvement in heat resistance | Improvement in oxidation resistance | Improvement in reactivity |
|---|---|---|---|---|
| | Rate (%) relative to wild type | Rate (%) relative to wild type | Rate (%) relative to wild type | Rate (%) relative to wild type |
| Wild type | | 100% | 100% | 100% |
| Gln | | 110% | 118% | |
| Pro | | 120% | | 136% |
| Glu | | 131% | 117% | 110% |
| Ser | | 143% | 122% | |
| Tyr | | 161% | 130% | |

Mutation point V6

| Amino acid after substitution | Reduction in temperature stability | Improvement in heat resistance | Improvement in oxidation resistance | Improvement in reactivity |
|---|---|---|---|---|
| | Rate (%) relative to wild type | Rate (%) relative to wild type | Rate (%) relative to wild type | Rate (%) relative to wild type |
| Wild type | 100% | | 100% | |
| Pro | 0% | | 191% | |

Mutation point R26

| Amino acid after substitution | Reduction in temperature stability | Improvement in heat resistance | Improvement in oxidation resistance | Improvement in reactivity |
|---|---|---|---|---|
| | Rate (%) relative to wild type | Rate (%) relative to wild type | Rate (%) relative to wild type | Rate (%) relative to wild type |
| Wild type | 100% | | 100% | 100% |
| Lys | 45% | | 120% | |
| Gln | 32% | | 135% | |
| Met | 29% | | 118% | |
| His | 3% | | 109% | 109% |
| Tyr | 2% | | 139% | |
| Asp | 0% | | 148% | |
| Gly | 0% | | 137% | |
| Asn | 0% | | 145% | |
| Pro | 0% | | 158% | |
| Ser | 0% | | 157% | |
| Val | | 159% | 158% | |

Mutation point E28

| Amino acid after substitution | Reduction in temperature stability | Improvement in heat resistance | Improvement in oxidation resistance | Improvement in reactivity |
|---|---|---|---|---|
| | Rate (%) relative to wild type | Rate (%) relative to wild type | Rate (%) relative to wild type | Rate (%) relative to wild type |
| Wild type | 100% | | 100% | |
| Val | 77% | | 131% | |
| Arg | 49% | | 158% | |
| Lys | 46% | | 122% | |
| Met | 35% | | 121% | |
| Asn | 17% | | 205% | |
| Phe | 9% | | 226% | |
| Gly | 4% | | 201% | |
| Leu | 0% | | 121% | |
| Tyr | 0% | | 228% | |

Mutation point V30

| Amino acid after substitution | Reduction in temperature stability | Improvement in heat resistance | Improvement in oxidation resistance | Improvement in reactivity |
|---|---|---|---|---|
| | Rate (%) relative to wild type | Rate (%) relative to wild type | Rate (%) relative to wild type | Rate (%) relative to wild type |
| Wild type | 100% | | | 100% |
| Pro | 28% | | | 108% |
| Gly | 0% | | | 116% |
| Asn | 0% | | | 109% |
| Arg | 0% | | | 126% |
| Tyr | 0% | | | 106% |

*Fig. 5-1*

Mutation point Y42

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | | 100% | |
| Phe | 64% | | 131% | |
| Leu | 0% | | 115% | |
| Met | 0% | | 109% | |

Mutation point E58

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | | 100% | |
| Tyr | 78% | | 174% | |
| Met | 76% | | 151% | |
| Ala | 58% | | 123% | |
| Phe | 48% | | 200% | |
| Ile | 45% | | 133% | |
| Val | 44% | | 140% | |
| Arg | 42% | | 207% | |
| Lys | 42% | | 167% | |
| Leu | 32% | | 143% | |
| Gln | 31% | | 116% | |

Mutation point L60

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | | | 100% |
| Ile | 74% | | | 107% |

Mutation point V67

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | | 100% | |
| Ala | 0% | | 125% | |
| Ser | 0% | | 122% | |

Mutation point T68

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | 100% | 100% | |
| Cys | 89% | | 107% | |
| Leu | 56% | | 118% | |
| Met | 29% | | 133% | |
| Val | | 116% | 131% | |
| Ile | | 119% | 130% | |

Mutation point Q74

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | | | 100% | 100% |
| Val | | | 118% | 115% |

Mutation point T77

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | | 100% | 100% |
| Glu | 84% | | | 110% |
| Cys | 79% | | 108% | |
| Asp | | | 111% | 113% |

*Fig. 5-2*

Mutation point S199

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | 100% | 100% | 100% |
| Gly | 86% | | | 113% |
| Cys | | 122% | 120% | 158% |

Mutation point T273

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | | 100% | |
| Glu | 12% | | 124% | |

Mutation point S284

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | 100% | 100% | 100% |
| Met | 79% | | | 112% |
| Phe | 73% | | | 109% |
| Leu | | 112% | | 108% |
| His | | 149% | 134% | |
| Lys | | 158% | | 112% |
| Arg | | 173% | 127% | |

Mutation point Y291

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | | 100% | |
| Ile | 30% | | 110% | |
| Leu | 9% | | 120% | |
| Cys | 0% | | 122% | |
| Asn | 0% | | 124% | |
| Ser | 0% | | 114% | |
| Val | 0% | | 126% | |

Mutation point S299

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | 100% | | | 100% |
| Val | 84% | | | 129% |
| Lys | 82% | | | 123% |
| Met | 81% | | | 125% |
| Ala | 79% | | | 123% |

Mutation point S303

| Amino acid after substitution | Reduction in temperature stability | Improvement in heat resistance | Improvement in oxidation resistance | Improvement in reactivity |
| --- | --- | --- | --- | --- |
| | Rate (%) relative to wild type | Rate (%) relative to wild type | Rate (%) relative to wild type | Rate (%) relative to wild type |
| Wild type | | 100% | | 100% |
| Lys | | 128% | | 111% |

*Fig. 5-3*

Mutation point R5

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Gln | 92% | 68% | 1.3 |
| Pro | 98% | 72% | 1.4 |
| Cys | 79% | 55% | 1.4 |
| Met | 60% | 42% | 1.4 |
| Ile | 87% | 58% | 1.5 |
| Val | 91% | 59% | 1.5 |
| Tyr | 56% | 22% | 2.5 |
| Phe | 57% | 22% | 2.6 |
| Ser | 47% | 15% | 3.1 |
| Asn | 54% | 14% | 3.8 |
| Thr | 49% | 7% | 6.6 |
| Gly | 37% | 4% | 8.5 |

Mutation point Y34

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| His | 66% | 37% | 1.8 |
| Met | 40% | 10% | 4.2 |

Mutation point W59

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Lys | 71% | 53% | 1.3 |
| Glu | 54% | 30% | 1.8 |

Mutation point S61

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Thr | 54% | 16% | 3.4 |
| Val | 52% | 14% | 3.7 |
| Tyr | 36% | 1% | 35.5 |
| Asp | 36% | 1% | 36.2 |
| Ile | 40% | 1% | 40.0 |
| Leu | 40% | 1% | 40.1 |
| Asn | 40% | 1% | 40.4 |
| Glu | 41% | 1% | 40.9 |
| Met | 42% | 1% | 42.2 |
| Phe | 43% | 1% | 42.7 |
| Trp | 45% | 1% | 44.6 |
| Gln | 45% | 1% | 44.9 |
| Pro | 45% | 1% | 45.5 |
| His | 48% | 1% | 48.3 |
| Lys | 54% | 1% | 53.8 |

*Fig. 6-1*

Mutation point Y62

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Asp | 64% | 41% | 1.6 |
| Pro | 37% | 1% | 37.1 |

Mutation point G63

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Asp | 28% | 1% | 27.6 |
| Gln | 31% | 1% | 30.5 |
| Tyr | 31% | 1% | 31.3 |
| Arg | 31% | 1% | 31.4 |
| Lys | 32% | 1% | 32.2 |
| His | 33% | 1% | 33.3 |
| Pro | 35% | 1% | 35.1 |
| Met | 35% | 1% | 35.4 |
| Asn | 40% | 1% | 39.7 |
| Cys | 41% | 1% | 40.6 |
| Phe | 41% | 1% | 40.6 |
| Leu | 42% | 1% | 41.9 |
| Trp | 43% | 1% | 42.6 |
| Thr | 44% | 1% | 44.5 |
| Val | 47% | 1% | 47.3 |
| Ser | 50% | 1% | 50.1 |

Mutation point V65

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Cys | 45% | 18% | 2.5 |
| Thr | 35% | 1% | 34.5 |
| Lys | 35% | 1% | 34.9 |

Mutation point G66

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Trp | 56% | 29% | 1.9 |
| Lys | 31% | 3% | 11.7 |

Mutation point T68

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Pro | 30% | 1% | 30.4 |
| His | 32% | 1% | 31.7 |

*Fig. 6-2*

Mutation point W69

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Tyr | 80% | 58% | 1.4 |
| Asp | 31% | 1% | 30.8 |
| Pro | 36% | 1% | 35.8 |

Mutation point Q74

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Arg | 84% | 53% | 1.6 |
| Pro | 65% | 33% | 2.0 |

Mutation point F85

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Tyr | 60% | 43% | 1.4 |
| Trp | 101% | 64% | 1.6 |
| Leu | 53% | 22% | 2.4 |
| Ile | 39% | 14% | 2.8 |
| Gln | 57% | 21% | 2.8 |
| Cys | 61% | 20% | 3.0 |
| Thr | 44% | 14% | 3.3 |
| Ala | 58% | 17% | 3.4 |
| Val | 49% | 12% | 4.2 |
| Ser | 42% | 10% | 4.2 |
| Arg | 33% | 3% | 9.8 |
| His | 34% | 2% | 22.5 |
| Asn | 31% | 1% | 33.5 |

Mutation point F108

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Gln | 75% | 47% | 1.6 |
| Cys | 50% | 25% | 2.0 |
| Glu | 33% | 12% | 2.8 |
| Ser | 33% | 9% | 3.6 |
| Asn | 41% | 11% | 3.7 |

Mutation point F117

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Cys | 48% | 18% | 2.7 |
| Ile | 40% | 12% | 3.3 |
| Trp | 49% | 13% | 3.7 |
| Val | 52% | 11% | 4.8 |
| Ala | 41% | 5% | 8.7 |
| Gly | 36% | 2% | 18.8 |
| Thr | 33% | 2% | 19.2 |
| Asn | 42% | 1% | 63.5 |

*Fig. 6-3*

Mutation point Y198

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Phe | 71% | 58% | 1.2 |
| His | 76% | 45% | 1.7 |
| Leu | 47% | 5% | 9.1 |
| Ser | 36% | 2% | 22.1 |
| Met | 34% | 1% | 33.9 |
| Ile | 37% | 1% | 37.4 |

Mutation point S199

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Gln | 39% | 17% | 2.3 |
| Pro | 31% | 1% | 30.8 |

Mutation point K200

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Tyr | 60% | 23% | 2.6 |
| Met | 33% | 1% | 32.5 |
| Ile | 34% | 1% | 34.1 |
| Arg | 37% | 1% | 36.8 |
| Leu | 38% | 1% | 37.6 |
| Val | 47% | 1% | 46.8 |

Mutation point H201

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Lys | 72% | 12% | 5.9 |
| Arg | 64% | 9% | 7.0 |
| Met | 33% | 1% | 33.3 |
| Leu | 34% | 1% | 33.7 |
| Gln | 34% | 1% | 34.2 |

Mutation point F202

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Tyr | 95% | 76% | 1.3 |
| Met | 43% | 18% | 2.4 |
| His | 46% | 6% | 8.0 |
| Val | 33% | 1% | 29.3 |
| Cys | 34% | 1% | 34.3 |

Mutation point W203

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Tyr | 32% | 3% | 11.1 |

*Fig. 6-4*

Mutation point F223

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Tyr | 87% | 64% | 1.4 |
| Met | 37% | 9% | 3.9 |
| Leu | 32% | 5% | 6.7 |
| Trp | 35% | 2% | 15.7 |
| Val | 30% | 1% | 30.0 |
| His | 30% | 1% | 30.0 |
| Gly | 33% | 1% | 32.7 |
| Ala | 37% | 1% | 36.8 |

Mutation point R238

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Ala | 115% | 82% | 1.4 |
| Asp | 90% | 63% | 1.4 |
| Val | 97% | 63% | 1.5 |
| Gly | 99% | 60% | 1.6 |
| His | 69% | 33% | 2.1 |
| Ser | 42% | 17% | 2.5 |

Mutation point F251

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| His | 71% | 49% | 1.5 |
| Asn | 67% | 28% | 2.4 |
| Cys | 55% | 20% | 2.7 |
| Met | 47% | 17% | 2.8 |
| Arg | 44% | 12% | 3.6 |
| Ser | 39% | 6% | 6.7 |
| Ala | 36% | 5% | 6.8 |
| Thr | 41% | 6% | 7.4 |
| Leu | 31% | 2% | 14.6 |
| Pro | 29% | 1% | 29.3 |
| Gly | 32% | 1% | 31.7 |
| Val | 33% | 1% | 33.2 |
| Gln | 33% | 1% | 33.3 |

Mutation point V252

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Met | 76% | 38% | 2.0 |
| Leu | 117% | 46% | 2.5 |
| Thr | 36% | 9% | 3.8 |
| Cys | 43% | 10% | 4.5 |

*Fig. 6-5*

Mutation point N253

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Thr | 34% | 1% | 34.0 |
| Val | 41% | 1% | 41.2 |
| Lys | 47% | 1% | 47.2 |
| Cys | 37% | 1% | 59.9 |
| Arg | 62% | 1% | 61.5 |

Mutation point Y256

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Leu | 41% | 1% | 41.3 |
| Val | 46% | 1% | 45.7 |
| Ile | 49% | 1% | 49.4 |

Mutation point G257

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Ala | 92% | 38% | 2.4 |
| Cys | 56% | 1% | 56.0 |

Mutation point W258

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Tyr | 61% | 29% | 2.1 |
| Phe | 42% | 18% | 2.3 |
| Asn | 32% | 1% | 31.7 |

Mutation point T273

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Asn | 43% | 9% | 4.5 |

*Fig. 6-6*

Mutation point G275

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Ala | 106% | 73% | 1.5 |
| Cys | 95% | 34% | 2.8 |
| Ser | 92% | 30% | 3.1 |
| Val | 53% | 2% | 22.9 |
| Lys | 30% | 1% | 30.4 |
| Ile | 32% | 1% | 32.1 |
| Phe | 33% | 1% | 33.4 |
| His | 33% | 1% | 33.5 |
| Arg | 53% | 2% | 33.5 |
| Leu | 34% | 1% | 33.9 |
| Pro | 34% | 1% | 34.4 |
| Gln | 34% | 1% | 34.5 |
| Tyr | 36% | 1% | 35.7 |
| Asn | 37% | 1% | 37.2 |
| Met | 38% | 1% | 38.5 |
| Thr | 59% | 1% | 46.5 |

Mutation point N276

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Gly | 33% | 1% | 33.5 |
| Met | 34% | 1% | 34.4 |
| Gln | 35% | 1% | 35.0 |
| His | 36% | 1% | 36.4 |

Mutation point H277

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Asn | 59% | 38% | 1.6 |
| Ser | 61% | 4% | 14.8 |
| Gln | 50% | 2% | 29.3 |
| Cys | 38% | 1% | 31.0 |
| Glu | 33% | 1% | 32.7 |
| Lys | 33% | 1% | 32.7 |
| Asp | 34% | 1% | 34.2 |
| Ile | 35% | 1% | 34.8 |
| Arg | 59% | 2% | 34.9 |
| Met | 39% | 1% | 39.3 |
| Pro | 44% | 1% | 43.9 |
| Leu | 46% | 1% | 46.0 |
| Trp | 52% | 1% | 46.9 |
| Val | 47% | 1% | 47.4 |
| Tyr | 51% | 1% | 50.7 |
| Gly | 64% | 1% | 51.7 |
| Phe | 52% | 1% | 52.1 |
| Thr | 52% | 1% | 52.1 |

*Fig. 6-7*

Mutation point Y278

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Pro | 53% | 2% | 31.6 |
| Asp | 42% | 1% | 41.5 |

Mutation point H279

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Asn | 100% | 75% | 1.3 |

Mutation point S284

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Cys | 58% | 40% | 1.5 |

Mutation point M288

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Val | 53% | 43% | 1.2 |
| Gln | 43% | 17% | 2.5 |
| Thr | 39% | 3% | 15.3 |

Mutation point V290

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Thr | 84% | 59% | 1.4 |
| Cys | 82% | 54% | 1.5 |
| Leu | 53% | 27% | 2.0 |
| Met | 69% | 29% | 2.3 |
| Ala | 69% | 25% | 2.7 |
| Ser | 45% | 1% | 44.8 |
| Asn | 49% | 1% | 48.9 |

Mutation point Y291

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| His | 70% | 47% | 1.5 |
| Thr | 51% | 23% | 2.2 |
| Glu | 32% | 3% | 9.3 |
| Gly | 32% | 1% | 32.2 |

*Fig. 6-8*

Mutation point W298

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Phe | 75% | 33% | 2.3 |
| Tyr | 54% | 5% | 10.0 |
| Ile | 34% | 1% | 33.6 |
| Leu | 36% | 1% | 35.6 |
| Met | 38% | 1% | 38.1 |

Mutation point S299

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Asn | 70% | 57% | 1.2 |
| Pro | 51% | 10% | 5.1 |

Mutation point Y302

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Leu | 53% | 27% | 2.0 |
| His | 68% | 33% | 2.1 |
| Met | 54% | 21% | 2.6 |
| Val | 49% | 16% | 3.0 |
| Cys | 47% | 14% | 3.4 |
| Thr | 38% | 9% | 4.3 |
| Pro | 31% | 7% | 4.6 |
| Ser | 35% | 7% | 5.1 |
| Trp | 71% | 13% | 5.5 |

Mutation point S303

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Ile | 108% | 82% | 1.3 |
| Gln | 106% | 80% | 1.3 |
| Asp | 98% | 67% | 1.5 |
| His | 98% | 67% | 1.5 |
| Glu | 102% | 67% | 1.5 |

Mutation point F305

| Amino acid after substitution | Deamidation activity ratio to wild type (%) | transglutaminase activity ratio to wild type (%) | Deamidation activity/ transglutaminase activity value relative to wild type |
|---|---|---|---|
| Wild type | 100% | 100% | 1.0 |
| Trp | 80% | 40% | 2.0 |
| His | 79% | 35% | 2.2 |
| Tyr | 55% | 5% | 10.4 |

*Fig. 6-9*

MODIFIED TRANSGLUTAMINASE

TECHNICAL FIELD

The present invention relates to transglutaminase. More specifically, the present invention relates to a modified transglutaminase having changed or improved properties, use thereof and the like. The present application claims priority based on Japanese Patent Application No. 2017-231192 filed on Nov. 30, 2017, the entire contents of which are incorporated herein by reference.

Sequence Listing

The instant application contains a Sequence Listing which has been submitted in XML format and is hereby incorporated by reference in its entirety. The XML Sequence Listing file is named 18212427_SEQLIST.xml and was created on Oct. 24, 2023 and is 49,829 bytes (48.6 KB) in size.

BACKGROUND ART

Transglutaminase is an enzyme that catalyzes the acyl transfer reaction of the γ-carboxamide group of a glutamine residue in a peptide chain. When the ε-amino group of a lysine residue in a protein acts as an acyl acceptor, intramolecular or intermolecular ε-(γ-Gln)-Lys crosslinks are formed within or between the molecules of the protein. Therefore, since the protein or peptide can be modified by utilizing the action of transglutaminase, transglutaminase derived from the genus *Streptomyces* (see, for example, PTL 1) is used in the binding of meat, and the manufacture of sausages, tofu, bread and noodles. In addition, the utilization of transglutaminase in not only the field of foods but also the fields of fibers, medicines, cosmetics and the like is being studied. With such expanded use, it has been attempted to improve the properties of transglutaminase (heat resistance, specific activity, substrate specificity, stability, etc.) (for example, PTL 2 and PTL 3, and NPL 1 to NPL 4).

CITATION LIST

Patent Literature

[PTL 1] JP H04-108381A
[PTL 2] JP 2002-253272A
[PTL 3] JP 2008-194004A

Non Patent Literature

[NPL 1] Marx C K et al., J Biotechnol. 2008 Sep. 10; 136 (3-4): 156-62.
[NPL 2] Tagami U et al., Protein Eng Des S el. 2009 December; 22 (12): 747-752.
[NPL 3] Yokoyama K et al., Appl Microbiol Biotechnol (2010) 87: 2087-2096.
[NPL 4] Buettner K et al., Amino Acids. 2012 February; 42(2-3): 987-96.

SUMMARY OF INVENTION

Technical Problem

As described above, attempts have been made so far to improve transglutaminase for the purpose of improving heat resistance and specific activity. However, for reasons such as high utility and further expansion of use, the need for improvement of transglutaminase is still high. Accordingly, an object of the present invention is to find a new mutation effective for improving transglutaminase, and to thereby provide a highly useful modified transglutaminase (variant), use thereof and the like.

Solution to Problem

In order to solve the above problems, the present inventors have tried to improve *Streptomyces mobaraensis* derived transglutaminase by an amino acid substitution (conversion of a specific amino acid residue to another amino acid). After trials and errors, the inventors have successfully identified a plurality of mutations (combinations of an amino acid residue and an amino acid after substitution) effective for changes in its properties (reduction in temperature stability, improvement in heat resistance, improvement in oxidation resistance, improvement in reactivity, or conversion into deamidase). Notably, mutations that result in changes in two or more properties have also been found. Furthermore, some of the mutations by which such multiple improvements have been achieved have caused contradictory property changes, i.e., reduction in temperature stability and improvement in oxidation resistance. This fact is extremely unpredictable and falls beyond all expectations, and is remarkable. On the other hand, the above results are also important in providing information and means for designing and obtaining a modified transglutaminase that can achieve the purpose of improving transglutaminase.

On the other hand, many cases are also encountered in which it is highly likely that for a given enzyme, combinations of two effective mutations result in additive or synergistic effects. In addition, in light of the common technical knowledge that enzymes of the same kind show high levels of similarity in their structures (primary structures and steric structures) and it is highly probable that for these enzymes, a similar mutation leads to similar effects, if a mutations that has been found to be useful in a *Streptomyces mobaraensis*-derived transglutaminase having the amino acid sequence represented by SEQ ID NO: 1 is applied to another transglutaminase having a high structural similarity relative to the *Streptomyces mobaraensis*-derived transglutaminase, then there is a high probability that such a transglutaminase has effects comparable to those achieved in the *Streptomyces mobaraensis*-derived transglutaminase. Moreover, one skilled in the art could recognize that this approach is effective.

The following inventions are based mainly on the above results and considerations.

[1] A modified transglutaminase having an amino acid sequence which comprises any one of the following amino acid substitutions (1) to (134) in the sequence of SEQ ID NO: 1 or an amino acid sequence showing 80% or more identity to the amino acid sequence (provided that a difference in amino acid sequence occurs at a portion other than the position of the amino acid substitution), the modified transglutaminase exhibiting a property change corresponding to the amino acid substitution:

(1) an amino acid substitution in which the mutation point is V6, the amino acid after substitution is Q, I, M, S, C, K, L, H, F, G, N, P, R, W or Y, and the property change due to the amino acid substitution is a reduction in temperature stability;

(2) an amino acid substitution in which the mutation point is R26, the amino acid after substitution is K, Q, M, H, Y, D, G, N, P or S, and the property change due to the amino acid substitution is a reduction in temperature stability;

(3) an amino acid substitution in which the mutation point is E28, the amino acid after substitution is V, Q, W, R, K, M, N, F, G, L, P or Y, and the property change due to the amino acid substitution is a reduction in temperature stability;

(4) an amino acid substitution in which the mutation point is V30, the amino acid after substitution is P, C, A, E, F, G, H, K, N, Q, R, W, Y or L, and the property change due to the amino acid substitution is a reduction in temperature stability;

(5) an amino acid substitution in which the mutation point is Y34, the amino acid after substitution is A, and the property change due to the amino acid substitution is a reduction in temperature stability;

(6) an amino acid substitution in which the mutation point is Y42, the amino acid after substitution is F, A, C, D, E, G, I, L, M, Q, S, T, V or W, and the property change due to the amino acid substitution is a reduction in temperature stability;

(7) an amino acid substitution in which the mutation point is E58, the amino acid after substitution is Y, M, A, F, I, V, R, K, N, L, S, Q, G or H, and the property change due to the amino acid substitution is a reduction in temperature stability;

(8) an amino acid substitution in which the mutation point is W59, the amino acid after substitution is R, N, Y, A, S, I, V, D, G or P, and the property change due to the amino acid substitution is a reduction in temperature stability;

(9) an amino acid substitution in which the mutation point is L60, the amino acid after substitution is I, M, V, A, C, E, F, Q, S, T, W or Y, and the property change due to the amino acid substitution is a reduction in temperature stability;

(10) an amino acid substitution in which the mutation point is Y62, the amino acid after substitution is C, R, G, K or S, and the property change due to the amino acid substitution is a reduction in temperature stability;

(11) an amino acid substitution in which the mutation point is V65, the amino acid after substitution is N, L, M, F, W or Y, and the property change due to the amino acid substitution is a reduction in temperature stability;

(12) an amino acid substitution in which the mutation point is V67, the amino acid after substitution is L, N, A, C, M, Q or S, and the property change due to the amino acid substitution is a reduction in temperature stability;

(13) an amino acid substitution in which the mutation point is T68, the amino acid after substitution is C, L, A, S, M, F, N, Q or Y, and the property change due to the amino acid substitution is a reduction in temperature stability;

(14) an amino acid substitution in which the mutation point is W69, the amino acid after substitution is H, M, I, C, E, F, G, K, L, N, Q, R, S, T or V, and the property change due to the amino acid substitution is a reduction in temperature stability;

(15) an amino acid substitution in which the mutation point is Q74, the amino acid after substitution is W, D, G or K, and the property change due to the amino acid substitution is a reduction in temperature stability;

(16) an amino acid substitution in which the mutation point is Y75, the amino acid after substitution is R, Q, T or G, and the property change due to the amino acid substitution is a reduction in temperature stability;

(17) an amino acid substitution in which the mutation point is T77, the amino acid after substitution is M, H, E, C or G, and the property change due to the amino acid substitution is a reduction in temperature stability;

(18) an amino acid substitution in which the mutation point is F85, the amino acid after substitution is M, and the property change due to the amino acid substitution is a reduction in temperature stability;

(19) an amino acid substitution in which the mutation point is F90, the amino acid after substitution is C, M, H, L or V, and the property change due to the amino acid substitution is a reduction in temperature stability;

(20) an amino acid substitution in which the mutation point is F108, the amino acid after substitution is R, L, T, A, I, K, N or V, and the property change due to the amino acid substitution is a reduction in temperature stability;

(21) an amino acid substitution in which the mutation point is F117, the amino acid after substitution is M or L, and the property change due to the amino acid substitution is a reduction in temperature stability;

(22) an amino acid substitution in which the mutation point is S199, the amino acid after substitution is G, M, N, K or V, and the property change due to the amino acid substitution is a reduction in temperature stability;

(23) an amino acid substitution in which the mutation point is F202, the amino acid after substitution is L or W, and the property change due to the amino acid substitution is a reduction in temperature stability;

(24) an amino acid substitution in which the mutation point is W203, the amino acid after substitution is F, and the property change due to the amino acid substitution is a reduction in temperature stability;

(25) an amino acid substitution in which the mutation point is F254, the amino acid after substitution is Y or M, and the property change due to the amino acid substitution is a reduction in temperature stability;

(26) an amino acid substitution in which the mutation point is T273, and the amino acid after substitution is I, V, M, C, S, L, R, G, A, E, F, Y, D, K, W or H, and the property change due to the amino acid substitution is a reduction in temperature stability;

(27) an amino acid substitution in which the mutation point is N276, the amino acid after substitution is C, E, K, L, S, T or V, and the property change due to the amino acid substitution is a reduction in temperature stability;

(28) an amino acid substitution in which the mutation point is Y278, the amino acid after substitution is M, L, H, I, K, R, W, C, G, N, Q, S, T or V, and the property change due to the amino acid substitution is a reduction in temperature stability;

(29) an amino acid substitution in which the mutation point is S284, the amino acid after substitution is W, Y, M, F or N, and the property change due to amino acid substitution is a reduction in temperature stability;

(30) an amino acid substitution in which the mutation point is Y291, the amino acid after substitution is I, W, L, A, C, K, N, Q, R, S or V, and the property change due to the amino acid substitution is a reduction in temperature stability;

(31) an amino acid substitution in which the mutation point is S299, the amino acid after substitution is I, Y, V, K, M, Q, A, F, G or E, and the property change due to the amino acid substitution is a reduction in temperature stability;

(32) an amino acid substitution in which the mutation point is S303, the amino acid after substitution is N, G, C, V, P or Y, and the property change due to the amino acid substitution is a reduction in temperature stability;

(33) an amino acid substitution in which the mutation point is Y310, the amino acid after substitution is C, M or I, and the property change due to the amino acid substitution is a reduction in temperature stability;

(34) an amino acid substitution in which the mutation point is D3, the amino acid after substitution is Q, P, E, S or Y, and the property change due to the amino acid substitution is an improvement in heat resistance;

(35) an amino acid substitution in which the mutation point is R26, the amino acid after substitution is V, and the property change due to the amino acid substitution is an improvement in heat resistance;

(36) an amino acid substitution in which the mutation point is Y34, the amino acid after substitution is W, and the property change due to the amino acid substitution is an improvement in heat resistance;

(37) an amino acid substitution in which the mutation point is V67, the amino acid after substitution is H, and the property change due to the amino acid substitution is an improvement in heat resistance;

(38) an amino acid substitution in which the mutation point is T68, the amino acid after substitution is V or I, and the property change due to the amino acid substitution is an improvement in heat resistance;

(39) an amino acid substitution in which the mutation point is Q74, the amino acid after substitution is F, and the property change due to the amino acid substitution is an improvement in heat resistance;

(40) an amino acid substitution in which the mutation point is T77, the amino acid after substitution is Q, and the property change due to the amino acid substitution is an improvement in heat resistance;

(41) an amino acid substitution in which the mutation point is S199, the amino acid after substitution is C or Q, and the property change due to the amino acid substitution is an improvement in heat resistance;

(42) an amino acid substitution in which the mutation point is T273, the amino acid after substitution is Q, and the property change due to the amino acid substitution is an improvement in heat resistance;

(43) an amino acid substitution in which the mutation point is S284, the amino acid after substitution is L, H, K, P or R, and the property change due to the amino acid substitution is an improvement in heat resistance;

(44) an amino acid substitution in which the mutation point is S299, the amino acid after substitution is N, and the property change due to the amino acid substitution is an improvement in heat resistance;

(45) an amino acid substitution in which the mutation point is S303, the amino acid after substitution is K, and the property change due to the amino acid substitution is an improvement in heat resistance;

(46) an amino acid substitution in which the mutation point is D3, the amino acid after substitution is E, Q, S or Y, and the property change due to the amino acid substitution is an improvement in oxidation resistance;

(47) an amino acid substitution in which the mutation point is V6, the amino acid after substitution is P, and the property change due to the amino acid substitution is an improvement in oxidation resistance;

(48) an amino acid substitution in which the mutation point is R26, the amino acid after substitution is M, K, W, C, Q, G, Y, E, T, N, D, I, S, P or V, and the property change due to the amino acid substitution is an improvement in oxidation resistance;

(49) an amino acid substitution in which the mutation point is E28, the amino acid after substitution is L, M, K, C, V, R, W, G, N, F, Y or H, and the property change due to the amino acid substitution is an improvement in oxidation resistance;

(50) an amino acid substitution in which the mutation point is Y42, the amino acid after substitution is L, N or F, and the property change due to the amino acid substitution is an improvement in oxidation resistance;

(51) an amino acid substitution in which the mutation point is E58, the amino acid after substitution is Q, A, I, V, L, T, M, K, Y, W, F or R, and the property change due to the amino acid substitution is an improvement in oxidation resistance;

(52) an amino acid substitution in which the mutation point is V67, the amino acid after substitution is T, S or A, and the property change due to the amino acid substitution is an improvement in oxidation resistance;

(53) an amino acid substitution in which the mutation point is T68, the amino acid after substitution is L, I, V or M, and the property change due to the amino acid substitution is an improvement in oxidation resistance;

(54) an amino acid substitution in which the mutation point is Q74, the amino acid after substitution is V, and the property change due to the amino acid substitution is an improvement in oxidation resistance;

(55) an amino acid substitution in which the mutation point is T77, the amino acid after substitution is D, and the property change due to the amino acid substitution is an improvement in oxidation resistance;

(56) an amino acid substitution in which the mutation point is S199, the amino acid after substitution is C, and the property change due to the amino acid substitution is an improvement in oxidation resistance;

(57) an amino acid substitution in which the mutation point is T273, the amino acid after substitution is E, and the property change due to the amino acid substitution is an improvement in oxidation resistance;

(58) an amino acid substitution in which the mutation point is S284, the amino acid after substitution is R or H, and the property change due to the amino acid substitution is an improvement in oxidation resistance;

(59) an amino acid substitution in which the mutation point is Y291, the amino acid after substitution is I, S, F, L, C, N, V or M, and the property change due to the amino acid substitution is an improvement in oxidation resistance;

(60) an amino acid substitution in which the mutation point is S284, the amino acid after substitution is M, K or V, and the property change due to the amino acid substitution is an improvement in reactivity;

(61) an amino acid substitution in which the mutation point is F251, the amino acid after substitution is Y, and the property change due to the amino acid substitution is an improvement in reactivity;

(62) an amino acid substitution in which the mutation points are V6 and Y75, the amino acid after substitution at the mutation point V6 is E, the amino acid after substitution at the mutation point Y75 is F, and the property change due to the amino acid substitution is an improvement in reactivity;

(63) an amino acid substitution in which the mutation points are D3 and T77, the amino acid after substitution at the mutation point D3 is P, the amino acid after substitution at the mutation point T77 is Q, and the property change due to the amino acid substitution is an improvement in reactivity;

(64) an amino acid substitution in which the mutation point is D3, the amino acid after substitution is Q, S or Y, and the property changes due to the amino acid substitution are improvements in heat resistance and oxidation resistance;

(65) an amino acid substitution in which the mutation point is D3, the amino acid after substitution is P, and the property changes due to the amino acid substitution are improvements in heat resistance and reactivity;

(66) an amino acid substitution in which the mutation point is D3, the amino acid after substitution is E, and the property changes due to the amino acid substitution are improvements in heat resistance, oxidation resistance and reactivity;

(67) an amino acid substitution in which the mutation point is V6, the amino acid after substitution is P, and the property changes due to the amino acid substitution are a reduction in temperature stability and an improvement in oxidation resistance;

(68) an amino acid substitution in which the mutation point is R26, the amino acid after substitution is K, Q, M, Y, D, G, N, P or S, and the property changes due to the amino acid substitution are a reduction in temperature stability and an improvement in oxidation resistance;

(69) an amino acid substitution in which the mutation point is R26, the amino acid after substitution is V, and the property changes due to the amino acid substitution are improvements in heat resistance and oxidation resistance;

(70) an amino acid substitution in which the mutation point is R26, the amino acid after substitution is H, and the property changes due to the amino acid substitution are a reduction in temperature stability, and improvements in oxidation resistance and reactivity;

(71) an amino acid substitution in which the mutation point is E28, the amino acid after substitution is V, R, K, M, N, F, G, L or Y, and the property changes due to the amino acid substitution are a reduction in temperature stability and an improvement in oxidation resistance;

(72) an amino acid substitution in which the mutation point is V30, the amino acid after substitution is P, G, N, R or Y, and the property changes due to the amino acid substitution are a reduction in temperature stability and an improvement in reactivity;

(73) an amino acid substitution in which the mutation point is Y42, the amino acid after substitution is F, L or M, and the property changes due to the amino acid substitution are a reduction in temperature stability and an improvement in oxidation resistance;

(74) an amino acid substitution in which the mutation point is E58, the amino acid after substitution is Y, M, A, F, I, V, R, K, L or Q, and the property changes due to the amino acid substitution are a reduction in temperature stability and an improvement in oxidation resistance;

(75) an amino acid substitution in which the mutation point is L60, the amino acid after substitution is I, and the property changes due to the amino acid substitution are a reduction in temperature stability and an improvement in reactivity;

(76) an amino acid substitution in which the mutation point is V67, the amino acid after substitution is A or S, and the property changes due to the amino acid substitution are a reduction in temperature stability and an improvement in oxidation resistance;

(77) an amino acid substitution in which the mutation point is T68, the amino acid after substitution is C, L or M, and the property changes due to the amino acid substitution are a reduction in temperature stability and an improvement in oxidation resistance;

(78) an amino acid substitution in which the mutation point is T68, the amino acid after substitution is V or I, and the property changes due to the amino acid substitution are improvements in heat resistance and oxidation resistance;

(79) an amino acid substitution in which the mutation point is Q74, the amino acid after substitution is V, and the property changes due to the amino acid substitution are improvements in oxidation resistance and reactivity;

(80) an amino acid substitution in which the mutation point is T77, the amino acid after substitution is C, and the property changes due to the amino acid substitution are a reduction in temperature stability and an improvement in oxidation resistance;

(81) an amino acid substitution in which the mutation point is T77, the amino acid after substitution is E, and the property changes due to the amino acid substitution are a reduction in temperature stability and an improvement in reactivity;

(82) an amino acid substitution in which the mutation point is T77, the amino acid after substitution is D, and the property changes due to the amino acid substitution are improvements in oxidation resistance and reactivity;

(83) an amino acid substitution in which the mutation point is S199, the amino acid after substitution is G, and the property changes due to the amino acid substitution are a reduction in temperature stability and an improvement in reactivity;

(84) an amino acid substitution in which the mutation point is S199, the amino acid after substitution is C, and the property changes due to the amino acid substitution are improvements in heat resistance, oxidation resistance and reactivity;

(85) an amino acid substitution in which the mutation point is T273, the amino acid after substitution is E, and the property changes due to the amino acid substitution are a reduction in temperature stability and an improvement in oxidation resistance;

(86) an amino acid substitution in which the mutation point is S284, the amino acid after substitution is M or F, and the property changes due to the amino acid substitution are a reduction in temperature stability and an improvement in reactivity;

(87) an amino acid substitution in which the mutation point is S284, the amino acid after substitution is L or K, and the property changes due to the amino acid substitution are improvements in heat resistance and reactivity;

(88) an amino acid substitution in which the mutation point is S284, the amino acid after substitution is H or R, and the property changes due to the amino acid substitution are improvements in heat resistance and oxidation resistance;

(89) an amino acid substitution in which the mutation point is Y291, the amino acid after substitution is I, L, C, N, S or V, and the property changes due to the amino acid substitution are a reduction in temperature stability and an improvement in oxidation resistance;

(90) an amino acid substitution in which the mutation point is S299, the amino acid after substitution is V, K, M or A, and the property changes due to the amino acid substitution are a reduction in temperature stability and an improvement in reactivity;

(91) an amino acid substitution in which the mutation point is S303, the amino acid after substitution is K, and the property changes due to the amino acid substitution are improvements in heat resistance and reactivity;

(92) an amino acid substitution in which the mutation point is R5, the amino acid after substitution is Q, P, C, M, I, V, Y, F, S, N, T or G, and the property change due to the amino acid substitution is conversion into deamidase;

(93) an amino acid substitution in which the mutation point is Y34, the amino acid after substitution is H or M, and the property change due to the amino acid substitution is conversion into deamidase;

(94) an amino acid substitution in which the mutation point is W59, the amino acid after substitution is K or E, and the property change due to the amino acid substitution is conversion into deamidase;

(95) an amino acid substitution in which the mutation point is S61, the amino acid after substitution is T, V, Y, D, I, L, N, E, M, F, W, Q, P, H or K, and the property change due to the amino acid substitution is conversion into deamidase;

(96) an amino acid substitution in which the mutation point is Y62, the amino acid after substitution is D or P, and the property change due to the amino acid substitution is conversion into deamidase;

(97) an amino acid substitution in which the mutation point is G63, the amino acid after substitution is D, Q, Y, R, K, H, P, M, N, C, F, L, W, T, V or S, and the property change due to the amino acid substitution is conversion into deamidase;

(98) an amino acid substitution in which the mutation point is V65, the amino acid after substitution is C, T or K, and the property change due to the amino acid substitution is conversion into deamidase;

(99) an amino acid substitution in which the mutation point is G66, the amino acid after substitution is W or K, and the property change due to the amino acid substitution is conversion into deamidase;

(100) an amino acid substitution in which the mutation point is T68, the amino acid after substitution is P or H, and the property change due to the amino acid substitution is conversion into deamidase;

(101) an amino acid substitution in which the mutation point is W69, the amino acid after substitution is Y, D or P, and the property change due to the amino acid substitution is conversion into deamidase;

(102) an amino acid substitution in which the mutation point is Q74, the amino acid after substitution is R or P, and the property change due to the amino acid substitution is conversion into deamidase;

(103) an amino acid substitution in which the mutation point is F85, the amino acid after substitution is Y, W, L, I, Q, C, T, A, V, S, R, H or N, and the property change due to the amino acid substitution is conversion into deamidase;

(104) an amino acid substitution in which the mutation point is F108, the amino acid after substitution is Q, C, E, S or N, and the property change due to the amino acid substitution is conversion into deamidase;

(105) an amino acid substitution in which the mutation point is F117, the amino acid after substitution is C, I, W, V, A, G, T or N, and the property change due to the amino acid substitution is conversion into deamidase;

(106) an amino acid substitution in which the mutation point is Y198, the amino acid after substitution is F, H, L, S, M or I, and the property change due to the amino acid substitution is conversion into deamidase;

(107) an amino acid substitution in which the mutation point is S199, the amino acid after substitution is Q or P, and the property change due to the amino acid substitution is conversion into deamidase;

(108) an amino acid substitution in which the mutation point is K200, the amino acid after substitution is Y, M, I, R, L or V, and the property change due to the amino acid substitution is conversion into deamidase;

(109) an amino acid substitution in which the mutation point is H201, the amino acid after substitution is K, R, M, L or Q, and the property change due to the amino acid substitution is conversion into deamidase;

(110) an amino acid substitution in which the mutation point is F202, the amino acid after substitution is Y, M, H, V or C, and the property change due to the amino acid substitution is conversion into deamidase;

(111) an amino acid substitution in which the mutation point is W203, the amino acid after substitution is Y, and the property change due to the amino acid substitution is conversion into deamidase;

(112) an amino acid substitution in which the mutation point is F223, the amino acid after substitution is Y, M, L, W, V, H, G or A, and the property change due to the amino acid substitution is conversion into deamidase;

(113) an amino acid substitution in which the mutation point is R238, the amino acid after substitution is A, D, V, G, H or S, and the property change due to the amino acid substitution is conversion into deamidase;

(114) an amino acid substitution in which the mutation point is F251, the amino acid after substitution is H, N, C, M, R, S, A, T, L, P, G, V or Q, and the property change due to the amino acid substitution is conversion into deamidase;

(115) an amino acid substitution in which the mutation point is V252, the amino acid after substitution is M, L, T or C, and the property change due to the amino acid substitution is conversion into deamidase;

(116) an amino acid substitution in which the mutation point is N253, the amino acid after substitution is T, V, K, C or R, and the property change due to the amino acid substitution is conversion into deamidase;

(117) an amino acid substitution in which the mutation point is Y256, the amino acid after substitution is L, V or I, and the property change due to the amino acid substitution is conversion into deamidase;

(118) an amino acid substitution in which the mutation point is G257, the amino acid after substitution is A or C, and the property change due to the amino acid substitution is conversion into deamidase;

(119) an amino acid substitution in which the mutation point is W258, the amino acid after substitution is Y, F or N, and the property change due to the amino acid substitution is conversion into deamidase;

(120) an amino acid substitution in which the mutation point is T273, the amino acid after substitution is N, and the property change due to the amino acid substitution is conversion into deamidase;

(121) an amino acid substitution in which the mutation point is G275, the amino acid after substitution is A, C, S, V, K, I, F, H, R, L, P, Q, Y, N, M or T, and the property change due to the amino acid substitution is conversion into deamidase;

(122) an amino acid substitution in which the mutation point is N276, the amino acid after substitution is G, M, Q or H, and the property change due to the amino acid substitution is conversion into deamidase;

(123) an amino acid substitution in which the mutation point is H277, the amino acid after substitution is N, S, Q, C, E, K, D, I, R, M, P, L, W, V, Y, G, F or T, and the property change due to the amino acid substitution is conversion into deamidase;

(124) an amino acid substitution in which the mutation point is Y278, the amino acid after substitution is P or D, and the property change due to the amino acid substitution is conversion into deamidase;

(125) an amino acid substitution in which the mutation point is H279, the amino acid after substitution is N, and the property change due to the amino acid substitution is conversion into deamidase;

(126) an amino acid substitution in which the mutation point is S284, the amino acid after substitution is C, and the property change due to the amino acid substitution is conversion into deamidase;

(127) an amino acid substitution in which the mutation point is M288, the amino acid after substitution is V, Q or T, and the property change due to the amino acid substitution is conversion into deamidase;

(128) an amino acid substitution in which the mutation point is V290, the amino acid after substitution is T, C, L, M, A, S or N, and the property change due to the amino acid substitution is conversion into deamidase;

(129) an amino acid substitution in which the mutation point is Y291, the amino acid after substitution is H, T, E or G, and the property change due to the amino acid substitution is conversion into deamidase;

(130) an amino acid substitution in which the mutation point is W298, the amino acid after substitution is F, Y, I, L or M, and the property change due to the amino acid substitution is conversion into deamidase;

(131) an amino acid substitution in which the mutation point is S299, the amino acid after substitution is N or P, and the property change due to the amino acid substitution is conversion into deamidase;

(132) an amino acid substitution in which the mutation point is Y302, the amino acid after substitution is L, H, M, V, C, T, P, S or W, and the property change due to the amino acid substitution is conversion into deamidase;

(133) an amino acid substitution in which the mutation point is S303, the amino acid after substitution is I, Q, D, H or E, and the property change due to the amino acid substitution is conversion into deamidase; and (134) an amino acid substitution in which the mutation point is F305, the amino acid after substitution is W, H or Y, and the property change due to the amino acid substitution is conversion into deamidase.

[2] The modified transglutaminase according to [1], wherein the identity is 82% or more.

[3] The modified transglutaminase according to [1], wherein the identity is 85% or more.

[4] The modified transglutaminase according to [1], wherein the identity is 90% or more.

[5] The modified transglutaminase according to [1], which comprises an amino acid sequence of any of SEQ ID NOs: 2 to 10.

[6] A gene coding for the modified transglutaminase according to any one of [1] to [5].

[7] The gene according to [6], which comprises a base sequence of any of SEQ ID NOs: 18 to 26.

[8] A recombinant DNA comprising the gene according to [6] or [7].

[9] A microorganism possessing the recombinant DNA according to [8].

[10] An enzyme preparation comprising the modified transglutaminase according to any one of [1] to [5].

[11] A method for preparing a modified transglutaminase, comprising the following steps (I) to (III):

(I) providing a nucleic acid encoding the amino acid sequence of the modified transglutaminase according to any one of [1] to [5];

(II) expressing the nucleic acid, and (III) recovering an expression product.

[12] The method according to [11], wherein the amino acid sequence is an amino acid sequence of any of SEQ ID NOs: 2 to 10.

[13] The preparation method according to [12], wherein the nucleic acid comprises a base sequence according to any of SEQ ID NOs: 18 to 26.

BRIEF DESCRIPTION OF DRAWINGS

FIG. 1-1 Mutation points effective for reducing temperature stability. Effective amino acid substitutions were identified by substituting each mutation point with various amino acids and comparing the residual activity rate of each enzyme (variant) after substitution with that of the wild-type enzyme. From the measured activity values, the TG (transglutaminase) activity per mL of the culture solution of each mutated strain was calculated and used for evaluation.

FIG. 1-2 Continuation of FIG. 1.

FIG. 1-3 Continuation of FIG. 1.

FIG. 1-4 Continuation of FIG. 1.

FIG. 1-5 Continuation of FIG. 1.

FIG. 1-6 Continuation of FIG. 1.

FIG. 1-7 Continuation of FIG. 1.

FIG. 2-1 Mutation points effective for improving heat resistance. Effective amino acid substitutions were identified by substituting each mutation point with various amino acids and comparing the residual activity rate of each enzyme (variant) after substitution with that of the wild-type enzyme. From the measured activity values, the TG (transglutaminase) activity per mL of the culture solution of each mutated strain was calculated and used for evaluation.

FIG. 2-2 Continuation of FIG. 2.

FIG. 3-1 Mutation points effective for improving oxidation resistance. Effective amino acid substitutions were identified by substituting each mutation point with various amino acids and comparing the residual activity rate of each enzyme (variant) after substitution with that of the wild-type enzyme. From the measured activity values, the TG (transglutaminase) activity per mL of the culture solution of each mutated strain was calculated and used for evaluation.

FIG. 3-2 Continuation of FIG. 3.

FIG. 3-3 Continuation of FIG. 3.

FIG. 4 Mutation points effective for improving reactivity. Effective amino acid substitutions were identified by substituting each mutation point with various amino acids and comparing the activity of the enzymes (variants) after substitution with the wild-type enzyme. From the measured activity values, the TG (transglutaminase) activity per mL of the culture solution of each mutated strain was calculated and used for evaluation. V6E/Y75F and D3P/T77Q are double variants having two amino acid substitutions.

FIG. 5-1 Mutation points effective for changing two or more properties. Mutations (amino acid substitutions) effective for multiple improvements are shown for each mutation point.

FIG. 5-2 Continuation of FIG. 5.

FIG. 5-3 Continuation of FIG. 5.

FIG. 6-1 Mutation points effective for conversion into deamidase. Each mutation point was substituted with various amino acids, the deamidation activity and transglutaminase activity of each enzyme (variant) after substitution were calculated as values relative to those of the wild type enzyme, and the deamidation activity (ratio relative to the wild type)/transglutaminase activity (ratio relative to the wild type) value was determined and used for evaluation.

FIG. 6-2 Continuation of FIG. 6.

FIG. 6-3 Continuation of FIG. 6.

FIG. 6-4 Continuation of FIG. 6.

FIG. 6-5 Continuation of FIG. 6.

FIG. 6-6 Continuation of FIG. 6.

FIG. 6-7 Continuation of FIG. 6.

FIG. 6-8 Continuation of FIG. 6.

FIG. 6-9 Continuation of FIG. 6.

DESCRIPTION OF EMBODIMENTS

For convenience of description, some of the terms used in relation to the present invention are defined as follows.

Terminology

The term "modified transglutaminase" refers to an enzyme obtained by modification or mutation of a particular transglutaminase (which is referred to as a "reference transglutaminase" for convenience of description). Typically, the reference transglutaminase is a *Streptomyces mobaraensis* derived transglutaminase having the amino acid sequence of SEQ ID NO:1.

The term "*Streptomyces mobaraensis* derived transglutaminase" is a transglutaminase that is obtained from a strain of *Streptomyces mobaraensis* as the source, and includes transglutaminase produced by *Streptomyces mobaraensis*, transglutaminases expressed, for example, in other microorganism, using the genetic information of such enzyme, or the like.

In the present invention, an "amino acid substitution" is carried out as modification or mutation. Therefore, some amino acid residues are found to be different when a modified transglutaminase and the reference transglutaminase therefor are compared. In the specification, a modified transglutaminase is also referred to as a modified enzyme or as a variant.

In the specification, amino acids are designated according to the common practice, as their single letters as described below:

methionine: M; serine: S; alanine: A; threonine: T; valine: V; tyrosine: Y; leucine: L; asparagine: N; isoleucine: I; glutamine: Q; proline: P; aspartic acid: D; phenylalanine: F;

glutamic acid: E; tryptophan: W; lysine: K; cysteine: C; arginine: R; glycine: G; and histidine: H.

In the specification, the positions of amino acids in an amino acid sequence are specified by assigning the numbers from the N-terminus toward the C-terminus of the amino acid sequence, wherein the amino acid residue at the N-terminus of a mature transglutaminase is assigned to 1, i.e., the first amino acid.

According to conventional practices, an amino acid residue to be subjected to an amino acid substitution, i.e., a "mutation point", is expressed by a combination of one letter representing the type of amino acid and a numeral representing the position thereof. In addition, a mutation due to an amino acid substitution is expressed by adding one letter representing the type of amino acid after substitution to the right of the indication of the mutation point. Therefore, for example, if the mutation point is valine at position 6, it is expressed as "V6", and if the valine at position 6 is substituted with glutamine, the mutation is expressed as "V6Q".

1. Modified Transglutaminase

A first aspect of the present invention relates to a modified transglutaminase (hereinafter, referred to as "modified enzyme"). The modified enzyme of the present invention typically has an amino acid sequence which comprises one or more specific amino acid substitution(s) (mutation(s)) in the amino acid sequence of SEQ ID NO: 1. Due to this characteristic, the modified enzyme has a reduction in temperature stability, an improvement in heat resistance, an improvement in oxidation resistance, an improvement in reactivity or conversion into deamidase (improvement in ratio of the deamidation activity to the transglutaminase activity), or two or more of these property changes, relative to the transglutaminase comprising the amino acid sequence of SEQ ID NO: 1. The modified enzyme having a reduced temperature stability has a practical advantage of preventing denaturation of food in the heat inactivation step of the enzyme, and is highly useful in applications such as production of yogurt and cheese. On the other hand, the modified enzyme having an improved heat resistance exhibits high activity even at high temperatures, and is particularly suitable for use in applications such as synthesis of peptide compounds. Further, the modified enzyme having an improved oxidation resistance has an advantage such as high storage stability, and can be expected to have an effect of preventing inactivation during production, storage, and use of the enzyme. The modified enzyme having an improved reactivity has advantages of providing a high reaction efficiency and reducing the amount of the enzyme to be used, and is highly useful regardless of the application. Conversion into deamidase alters the substrate specificity, and particularly leads to expansion or creation of use (for example, use for purposes such as solubilization, emulsification, and improvement of foamability of protein). Transglutaminase is an enzyme that catalyzes an acyl transfer reaction between the primary amine and the γ-carboxamide group of the glutamine residue in the peptide chain. In the absence of the primary amine, water acts as an acyl receptor and transglutaminase catalyzes a deamidation reaction that converts the glutamine residue into a glutamic acid residue. The modified enzyme converted into deamidase exhibits a high deamidation catalytic capability, and is more preferable as an enzyme for use in deamidation. The amino acid sequence of SEQ ID NO: 1 is a sequence of *Streptomyces mobaraensis* derived transglutaminase.

As used herein, "comprising an amino acid substitution" means that the substituted amino acid is located at the mutation point, that is, the position of the amino acid residue at which a specified amino acid substitution occurs. Therefore, when an amino acid sequence comprising an amino acid substitution, i.e., a mutated amino-acid sequence, is compared with that represented by SEQ ID NO: 1 (reference amino-acid sequence) having no amino acid substitution, the mutated amino-acid sequence will be found to have a different amino acid residue at the position at which the amino acid substitution has occurred.

The temperature stability can be evaluated, for example, based on the residual activity when the enzyme is treated at 50° C. for 30 minutes. In the modified enzyme having a reduced temperature stability, the residual activity rate is lower than that of the reference transglutaminase. The residual activity rate of the modified enzyme is, for example, 90% or less, preferably 30% or less, more preferably 10% or less of that of the reference transglutaminase. The residual activity rate is calculated as follows.

$$\text{Residual activity rate (\%)} = \text{(enzyme activity after heat treatment)/(enzyme activity before heat treatment)} \times 100$$

The heat resistance can be evaluated, for example, based on the residual activity when the enzyme is treated at 50° C. for 30 minutes, as with the temperature stability. In the modified enzyme having an improved heat resistance, the residual activity rate is higher than that of the reference transglutaminase. The residual activity rate of the modified enzyme is, for example, 110% or more, preferably 120% or more, more preferably 130% or more of that of the reference transglutaminase.

The oxidation resistance can be evaluated based on the residual activity when the modified enzyme is treated with hydrogen peroxide as an oxidizing agent. A detailed evaluation method will be described later. In the modified enzyme having an improved oxidation resistance, the residual activity rate is higher than that of the reference transglutaminase. The residual activity rate of the modified enzyme is, for example, 110% or more, preferably 120% or more, more preferably 130% or more of that of the reference transglutaminase. The residual activity rate is calculated as follows.

$$\text{Residual activity rate (\%)} = \text{(enzyme activity after hydrogen peroxide treatment)/(enzyme activity before treatment)} \times 100$$

The modified enzyme in which the above property (temperature stability, heat resistance or oxidation resistance) has been changed is more useful than the reference transglutaminase in terms of the changed property, but a higher reactivity of the modified enzyme is better because the amount of the enzyme used (enzyme amount) can be reduced. For example, the reactivity of the modified enzyme is preferably 50% or more of that of the reference transglutaminase.

The reactivity can be evaluated, for example, based on the activity calculated by a measurement method which will be described in the Examples below. The modified enzyme having an improved reactivity shows activity higher than that of the reference transglutaminase. The reactivity (activity) of the modified enzyme is 110% or more, preferably 120% or more, further preferably 130% or more of the reactivity (activity) of the reference transglutaminase.

The conversion into deamidase can be evaluated based on the ratio of the deamidation activity (ratio relative to the reference transglutaminase) to the transglutaminase activity (ratio relative to the reference transglutaminase) (deamidation activity/transglutaminase activity). A detailed evaluation method will be described later. In the modified enzyme in which conversion into deamidase has occurred, the deamidation activity (ratio relative to the reference transglutaminase)/transglutaminase activity (ratio relative to reference transglutaminase) has a value of more than 1, preferably 1.2 or more, more preferably 2 or more, further preferably 10 or more.

Hereinafter, amino acid substitutions (mutation points and amino acids after substitution) that result in the property changes described above will be listed.

<Amino Acid Substitution Effective for Reducing Temperature Stability>

(1) An amino acid substitution in which the mutation point is V6, and the amino acid after substitution is Q, I, M, S, C, K, L, H, F, G, N, P, R, W or Y (2) An amino acid substitution in which the mutation point is R26, and the amino acid after substitution is K, Q, M, H, Y, D, G, N, P or S (3) An amino acid substitution in which the mutation point is E28, and the amino acid after substitution is V, Q, W, R, K, M, N, F, G, L, P or Y (4) An amino acid substitution in which the mutation point is V30, and the amino acid after substitution is P, C, A, E, F, G, H, K, N, Q, R, W, Y or L (5) An amino acid substitution in which the mutation point is Y34, and the amino acid after substitution is A (6) An amino acid substitution in which the mutation point is Y42, and the amino acid after substitution is F, A, C, D, E, G, I, L, M, Q, S, T, V or W (7) An amino acid substitution in which the mutation point is E58, and the amino acid after substitution is Y, M, A, F, I, V, R, K, N, L, S, Q, G or H (8) An amino acid substitution in which the mutation point is W59, and the amino acid after substitution is R, N, Y, A, S, I, V, D, G or P (9) An amino acid substitution in which the mutation point is L60, and the amino acid after substitution is I, M, V, A, C, E, F, Q, S, T, W or Y

(10) An amino acid substitution in which the mutation point is Y62, and the amino acid after substitution is C, R, G, K or S

(11) An amino acid substitution in which the mutation point is V65, and the amino acid after substitution is N, L, M, F, W or Y

(12) An amino acid substitution in which the mutation point is V67, and the amino acid after substitution is L, N, A, C, M, Q or S

(13) An amino acid substitution in which the mutation point is T68, and the amino acid after substitution is C, L, A, S, M, F, N, Q or Y

(14) An amino acid substitution in which the mutation point is W69, and the amino acid after substitution is H, M, I, C, E, F, G, K, L, N, Q, R, S, T or V

(15) An amino acid substitution in which the mutation point is Q74, and the amino acid after substitution is W, D, G or K

(16) An amino acid substitution in which the mutation point is Y75, and the amino acid after substitution is R, Q, T or G

(17) An amino acid substitution in which the mutation point is T77, and the amino acid after substitution is M, H, E, C or G

(18) An amino acid substitution in which the mutation point is F85, and the amino acid after substitution is M

(19) An amino acid substitution in which the mutation point is F90, and the amino acid after substitution is C, M, H, L or V

(20) An amino acid substitution in which the mutation point is F108, and the amino acid after substitution is R, L, T, A, I, K, N or V

(21) An amino acid substitution in which the mutation point is F117, and the amino acid after substitution is M or L

(22) An amino acid substitution in which the mutation point is S199, and the amino acid after substitution is G, M, N, K or V

(23) An amino acid substitution in which the mutation point is F202, and the amino acid after substitution is L or W

(24) An amino acid substitution in which the mutation point is W203, and the amino acid after substitution is F

(25) An amino acid substitution in which the mutation point is F254, and the amino acid after substitution is Y or M

(26) An amino acid substitution in which the mutation point is T273, and the amino acid after substitution is I, V, M, C, S, L, R, G, A, E, F, Y, D, K, W or H

(27) An amino acid substitution in which the mutation point is N276, and the amino acid after substitution is C, E, K, L, S, T or V

(28) An amino acid substitution in which the mutation point is Y278, and the amino acid after substitution is M, L, H, I, K, R, W, C, G, N, Q, S, T or V

(29) An amino acid substitution in which the mutation point is S284, and the amino acid after substitution is W, Y, M, F or N

(30) An amino acid substitution in which the mutation point is Y291, and the amino acid after substitution is I, W, L, A, C, K, N, Q, R, S or V

(31) An amino acid substitution in which the mutation point is S299, and the amino acid after substitution is I, Y, V, K, M, Q, A, F, G or E

(32) An amino acid substitution in which the mutation point is S303, and the amino acid after substitution is N, G, C, V, P or Y

(33) An amino acid substitution in which the mutation point is Y310, and the amino acid after substitution is C, M or I Among the above amino acid substitutions, the following amino acid substitutions provide a high degree of reduction in temperature stability, and thus are more preferable.

V6S, V6C, V6K, V6L, V6H, V6F, V6G, V6N, V6P, V6R, V6W, V6Y

R26M, R26H, R26Y, R26D, R26G, R26N, R26P, R26S

E28N, E28F, E28G, E28L, E28P, E28Y

V30P, V30C, V30A, V30E, V30F, V30G, V30H, V30K, V30N, V30Q, V30R, V30W, V30Y, V30L

Y34A

Y42A, Y42C, Y42D, Y42E, Y42G, Y421, Y42L, Y42M, Y42Q, Y42S, Y42T, Y42V, Y42W

E58G, E58H

W59S, W591, W59V, W59D, W59G, W59P

L60M, L60V, L60A, L60C, L60E, L60F, L60Q, L60S, L60T, L60W, L60Y

Y62C, Y62R, Y62G, Y62K, Y62S

V65N, V65L, V65M, V65F, V65W, V65Y

V67L, V67N, V67A, V67C, V67M, V67Q, V67S

T68M, T68F, T68N, T68Q, T68Y

W69M, W691, W69C, W69E, W69F, W69G, W69K, W69L, W69N, W69Q, W69R, W69S, W69T, W69V

Y75T, Y75G

F85M

F90V

F108T, F108A, F1081, F108K, F108N, F108V

F117L

S199K, S199V

F202W

T273L, T273R, T273G, T273A, T273E, T273F, T273Y, T273D, T273K, T273W, T273H

N276C, N276E, N276K, N276L, N276T, N276V, N276S

Y278L, Y278H, Y2781, Y278K, Y278R, Y278W, Y278C, Y278G, Y278N, Y278Q, Y278S, Y278T, Y278V

Y291W, Y291L, Y291A, Y291C, Y291K, Y291N, Y291Q, Y291R, Y291S, Y291V

S299E

Y310I

The following amino acid substitutions provide a particularly high degree of reduction in temperature stability, and thus are particularly preferable.

V6H, V6F, V6G, V6N, V6P, V6R, V6W, V6Y

R26H, R26Y, R26D, R26G, R26N, R26P, R26S

E28F, E28G, E28L, E28P, E28Y

V30C, V30A, V30E, V30F, V30G, V30H, V30K, V30N, V30Q, V30R, V30W, V30Y, V30L

Y34A

Y42A, Y42C, Y42D, Y42E, Y42G, Y421, Y42L, Y42M, Y42Q, Y42S, Y42T, Y42V, Y42W

W591, W59V, W59D, W59G, W59P

L60V, L60A, L60C, L60E, L60F, L60Q, L60S, L60T, L60W, L60Y

Y62C, Y62R, Y62G, Y62K, Y62S

V65M, V65F, V65W, V65Y

V67A, V67C, V67M, V67Q, V67S

T68F, T68N, T68Q, T68Y

W69M, W691, W69C, W69E, W69F, W69G, W69K, W69L, W69N, W69Q, W69R, W69S, W69T, W69V

Y75T, Y75G

F108A, F1081, F108K, F108N, F108V

F117L

F202W

T273F, T273Y, T273D, T273K, T273W, T273H

N276C, N276E, N276K, N276L, N276S, N276T, N276V

Y278K, Y278R, Y278W, Y278C, Y278G, Y278N, Y278Q, Y278S, Y278T, Y278V

Y291L, Y291A, Y291C, Y291K, Y291N, Y291Q, Y291R, Y291S, Y291V

S299E

The following amino acid substitutions provide a particularly high degree of reduction in temperature stability and a high reactivity, and thus are extremely preferable.

V6H, V6G, V6N, V6W

R26H, R26Y, R26N, R26S

E28F, E28G, E28L, E28Y

V30C, V30A, V30E, V30F, V30G, V30H, V30K, V30N, V30Q, V30R, V30W, V30Y, V30L

Y42C, Y42L, Y42M, Y42Q, Y42S, Y42W

W59I, W59V, W59G

L60V, L60C, L60F

Y62C, Y62R

V67C, V67M

W69M, W69I, W69C, W69F, W69L, W69T, W69V

Y75T

T273F, T273Y, T273H

Y278W

Y291L, Y291K, Y291R

<Amino Acid Substitution Effective for Improving Heat Resistance>

(34) An amino acid substitution in which the mutation point is D3, and the amino acid after substitution is Q, P, E, S or Y

(35) An amino acid substitution in which the mutation point is R26, and the amino acid after substitution is V

(36) An amino acid substitution in which the mutation point is Y34, and the amino acid after substitution is W

(37) An amino acid substitution in which the mutation point is V67, and the amino acid after substitution is H

(38) An amino acid substitution in which the mutation point is T68, and the amino acid after substitution is V or I

(39) An amino acid substitution in which the mutation point is Q74, and the amino acid after substitution is F

(40) An amino acid substitution in which the mutation point is T77, and the amino acid after substitution is Q

(41) An amino acid substitution in which the mutation point is S199, and the amino acid after substitution is C or Q

(42) An amino acid substitution in which the mutation point is T273, and the amino acid after substitution is Q

(43) An amino acid substitution in which the mutation point is S284, and the amino acid after substitution is L, H, K, P or R

(44) An amino acid substitution in which the mutation point is S299, and the amino acid after substitution is N

(45) An amino acid substitution in which the mutation point is S303, and the amino acid after substitution is K Among the above amino acid substitutions, the following amino acid substitutions provide a high degree of improvement in heat resistance, and thus are more preferable.

D3P, D3E, D3S, D3Y

R26V

Y34W

V67H

T77Q

S199C, S199Q

T273Q

S284H, S284K, S284P, S284R

S303K

The following amino acid substitutions provide a particularly high degree of improvement in heat resistance, and thus are particularly preferable.

D3E, D3S, D3Y

R26V

Y34W

V67H

S199Q

T273Q

S284H, S284K, S284P, S284R

The following amino acid substitutions provide a particularly high degree of improvement in heat resistance and a high reactivity, and thus are particularly preferable.

D3E, D3S, D3Y

R26V

Y34W

T273Q

S284H, S284K, S284P, S284R

<Amino Acid Substitution Effective for Improving Oxidation Resistance>

(46) An amino acid substitution in which the mutation point is D3, and the amino acid after substitution is E, Q, S or Y

(47) An amino acid substitution in which the mutation point is V6, and the amino acid after substitution is P

(48) An amino acid substitution in which the mutation point is R26, and the amino acid after substitution is M, K, W, C, Q, G, Y, E, T, N, D, I, S, P or V

(49) An amino acid substitution in which the mutation point is E28, and the amino acid after substitution is L, M, K, C, V, R, W, G, N, F, Y or H

(50) An amino acid substitution in which the mutation point is Y42, and the amino acid after substitution is L, N or F

(51) An amino acid substitution in which the mutation point is E58, and the amino acid after substitution is Q, A, I, V, L, T, M, K, Y, W, F or R

(52) An amino acid substitution in which the mutation point is V67, and the amino acid after substitution is T, S or A

(53) An amino acid substitution in which the mutation point is T68, and the amino acid after substitution is L, I, V or M

(54) An amino acid substitution in which the mutation point is Q74, and the amino acid after substitution is V

(55) An amino acid substitution in which the mutation point is T77, and the amino acid after substitution is D

(56) An amino acid substitution in which the mutation point is S199, and the amino acid after substitution is C

(57) An amino acid substitution in which the mutation point is T273, and the amino acid after substitution is E

(58) An amino acid substitution in which the mutation point is S284, and the amino acid after substitution is R or H

(59) An amino acid substitution in which the mutation point is Y291, and the amino acid after substitution is I, S, F, L, C, N, V or M Among the above amino acid substitutions, the following amino acid substitutions provide a high degree of improvement in oxidation resistance, and thus are more preferable.

D3S, D3Y

V6P

R26W, R26C, R26Q, R26G, R26Y, R26E, R26T, R26N, R26D, R26I, R26S, R26P, R26V

E28L, E28M, E28K, E28C, E28V, E28R, E28W, E28G, E28N, E28F, E28Y, E28H

E58A, E58I, E58V, E58L, E58T, E58M, E58K, E58Y, E58W, E58F, E58R

V67S, V67A

T68I, T68V, T68M

T273E

S284R, S284H

Y291C, Y291N, Y291V, Y291M

The following amino acid substitutions provide a particularly high degree of improvement in oxidation resistance, and thus are particularly preferable.

V6P

R26C, R26Q, R26G, R26Y, R26E, R26T, R26N, R26D, R26I, R26S, R26P, R26V

E28V, E28R, E28W, E28G, E28N, E28F, E28Y, E28H

Y42F

E58I, E58V, E58L, E58T, E58M, E58K, E58Y, E58W, E58F, E58R

T68I, T68V, T68M

S284H

The following amino acid substitutions provide a particularly high degree of improvement in oxidation resistance and a high reactivity, and thus are particularly preferable.

R26C, R26Q, R26Y, R26E, R26T, R26N, R26I, R26S, R26V

E28V, E28R, E28W, E28G, E28N, E28F, E28Y

Y42F

E58I, E58V, E58L, E58T, E58M, E58K, E58Y, E58W, E58F, E58R

S284H

<Amino Acid Substitution Effective for Improving Reactivity>

(60) An amino acid substitution in which the mutation point is S284, and the amino acid after substitution is M, K or V

(61) An amino acid substitution in which the mutation point is F251, and the amino acid after substitution is Y

(62) An amino acid substitution in which the mutation point is V6 and Y75, the amino acid after substitution at mutation point V6 is E, and the amino acid after substitution at mutation point Y75 is F

(63) An amino acid substitution in which the mutation points are D3 and T77, the amino acid after substitution at the mutation point D3 is P, and the amino acid after substitution at the mutation point T77 is Q Among the above amino acid substitutions, the following amino acid substitutions provide a high degree of improvement in reactivity, and thus are more preferable.

S284V

F251Y

Double variant of V6E and Y75F

Double variant of D3P and T77Q

The following amino acid substitutions provide a particularly high degree of improvement in reactivity, and thus are particularly preferable.

Double variant of V6E and Y75F

Double variant of D3P and T77Q

As will be described in the Examples below, some amino acid substitutions resulted in two or more property changes. That is, amino acid substitutions effective for multiple improvements were identified. Hereinafter, amino acid substitutions (mutation points and amino acids after substitution) that have been successfully identified will be listed together with the corresponding property changes.

(64) An amino acid substitution in which the mutation point is D3, the amino acid after substitution is Q, S or Y, and the property changes due to the amino acid substitution are improvements in heat resistance and oxidation resistance

(65) An amino acid substitution in which the mutation point is D3, the amino acid after substitution is P, and the property changes due to the amino acid substitution are improvements in heat resistance and reactivity

(66) An amino acid substitution in which the mutation point is D3, the amino acid after substitution is E, and the property changes due to the amino acid substitution are improvements in heat resistance, oxidation resistance and reactivity

(67) An amino acid substitution in which the mutation point is V6, the amino acid after substitution is P, and the property changes due to the amino acid substitution are a reduction in temperature stability and an improvement in oxidation resistance

(68) An amino acid substitution in which the mutation point is R26, the amino acid after substitution is K, Q, M, Y, D, G, N, P or S, and the property changes due to the amino acid substitution are a reduction in temperature stability and an improvement in oxidation resistance

(69) An amino acid substitution in which the mutation point is R26, the amino acid after substitution is V, and the property changes due to the amino acid substitution are improvements in heat resistance and oxidation resistance

(70) An amino acid substitution in which the mutation point is R26, the amino acid after substitution is H, and the property changes due to the amino acid substitution are a reduction in temperature stability, and improvements in oxidation resistance and reactivity

(71) An amino acid substitution in which the mutation point is E28, the amino acid after substitution is V, R, K, M, N, F, G, L or Y, and the property changes due to the amino acid substitution are a reduction in temperature stability and an improvement in oxidation resistance

(72) An amino acid substitution in which the mutation point is V30, the amino acid after substitution is P, G, N, R or Y, and the property changes due to the amino acid substitution a reduction in temperature stability and an improvement in reactivity

(73) An amino acid substitution in which the mutation point is Y42, the amino acid after substitution is F, L or M, and the property changes due to the amino acid substitution are a reduction in temperature stability and an improvement in oxidation resistance

(74) An amino acid substitution in which the mutation point is E58, the amino acid after substitution is Y, M, A, F, I, V, R, K, L or Q, and the property changes due to the amino acid substitution are a reduction in temperature stability and an improvement in oxidation resistance

(75) An amino acid substitution in which the mutation point is L60, the amino acid after substitution is I, and the property changes due to the amino acid substitution are a reduction in temperature stability and an improvement in reactivity

(76) An amino acid substitution in which the mutation point is V67, the amino acid after substitution is A or S, and the property changes due to the amino acid substitution are a reduction in temperature stability and an improvement in oxidation resistance

(77) An amino acid substitution in which the mutation point is T68, the amino acid after substitution is C, L or M, and the property changes due to the amino acid substitution are a reduction in temperature stability and an improvement in oxidation resistance

(78) An amino acid substitution in which the mutation point is T68, the amino acid after substitution is V or I, and the property changes due to the amino acid substitution are improvements in heat resistance and oxidation resistance

(79) An amino acid substitution in which the mutation point is Q74, the amino acid after substitution is V, and the property changes due to the amino acid substitution are improvements in oxidation resistance and reactivity

(80) An amino acid substitution in which the mutation point is T77, the amino acid after substitution is C, and the property changes due to the amino acid substitution are a reduction in temperature stability and an improvement in oxidation resistance

(81) An amino acid substitution in which the mutation point is T77, the amino acid after substitution is E, and the property changes due to the amino acid substitution are a reduction in temperature stability and an improvement in reactivity

(82) An amino acid substitution in which the mutation point is T77, the amino acid after substitution is D, and the property changes due to the amino acid substitution are improvements in oxidation resistance and reactivity

(83) An amino acid substitution in which the mutation point is S199, the amino acid after substitution is G, and the property changes due to the amino acid substitution are a reduction in temperature stability and an improvement in reactivity

(84) An amino acid substitution in which the mutation point is S199, the amino acid after substitution is C, and the property changes due to the amino acid substitution are improvements in heat resistance, oxidation resistance and reactivity

(85) An amino acid substitution in which the mutation point is T273, the amino acid after substitution is E, and the property changes due to the amino acid substitution are a reduction in temperature stability and an improvement in oxidation resistance

(86) An amino acid substitution in which the mutation point is S284, the amino acid after substitution is M or F, and the property changes due to the amino acid substitution are a reduction in temperature stability and an improvement in reactivity

(87) An amino acid substitution in which the mutation point is S284, the amino acid after substitution is L or K, and the property changes due to the amino acid substitution are improvements in heat resistance and reactivity

(88) An amino acid substitution in which the mutation point is S284, the amino acid after substitution is H or R, and the property changes due to the amino acid substitution are improvements in heat resistance and oxidation resistance

(89) An amino acid substitution in which the mutation point is Y291, the amino acid after substitution is I, L, C, N, S or V, and the property changes due to the amino acid substitution are a reduction in temperature stability and an improvement in oxidation resistance

(90) An amino acid substitution in which the mutation point is S299, the amino acid after substitution is V, K, M or A, and the property changes due to amino acid substitution are a reduction in temperature stability and an improvement in reactivity

(91) An amino acid substitution in which the mutation point is S303, the amino acid after substitution is K, and the property changes due to the amino acid substitution are improvements in heat resistance and reactivity.

Among the above amino acid substitutions, the following amino acid substitutions are accompanied by two contradictory property changes, i.e., a reduction in temperature stability and an improvement in oxidation resistance.

V6P

R26K, R26Q, R26M, R26Y, R26D, R26G, R26N, R26P, R26S

E28V, E28R, E28K, E28M, E28N, E28F, E28G, E28L, E28Y

Y42F, Y42L, Y42M

E58Y, E58M, E58A, E58F, E58I, E58V, E58R, E58K, E58L, E58Q

V67A, V67S

T68C, T68L, T68M

T77C

T273E

Y2911, 291L, Y291C, Y291N, Y291S, Y291V

<Amino Acid Substitution Effective for Conversion into Deamidase>

(92) An amino acid substitution in which the mutation point is R5, and the amino acid after substitution is Q, P, C, M, I, V, Y, F, S, N, T or G

(93) An amino acid substitution in which the mutation point is Y34, and the amino acid after substitution is H or M

(94) An amino acid substitution in which the mutation point is W59, and the amino acid after substitution is K or E

(95) An amino acid substitution in which the mutation point is S61, and the amino acid after substitution is T, V, Y, D, I, L, N, E, M, F, W, Q, P, H or K

(96) An amino acid substitution in which the mutation point is Y62, and the amino acid after substitution is D or P

(97) An amino acid substitution in which the mutation point is G63, and the amino acid after substitution is D, Q, Y, R, K, H, P, M, N, C, F, L, W, T, V or S

(98) An amino acid substitution in which the mutation point is V65, and the amino acid after substitution is C, T or K

(99) An amino acid substitution in which the mutation point is G66, and the amino acid after substitution is W or K (100) An amino acid substitution in which the mutation point is T68, and the amino acid after substitution is P or H (101) An amino acid substitution in which the mutation point is W69, and the amino acid after substitution is Y, D or P (102) An amino acid substitution in which the mutation point is Q74, and the amino acid after substitution is R or P (103) An amino acid substitution in which the mutation point is F85, and the amino acid after substitution is Y, W, L, I, Q, C, T, A, V, S, R, H or N (104) An amino acid substitution in which the mutation point is F108, and the amino acid after substitution is Q, C, E, S or N (105) An amino acid substitution in which the mutation point is F117, and the amino acid after substitution is C, I, W, V, A, G, T or N (106) An amino acid substitution in which the mutation point is Y198, and the amino acid after substitution is F, H, L, S, M or I (107) An amino acid substitution in which the mutation point is S199, and the amino acid after substitution is Q or P (108) An amino acid substitution in which the mutation point is K200, and the amino acid after substitution is Y, M, I, R, L or V (109) An amino acid substitution in which the mutation point is H201, and the amino acid after substitution is K, R, M, L or Q (110) An amino acid substitution in which the mutation point is F202, and the amino acid after substitution is Y, M, H, V or C (111) An amino acid substitution in which the mutation point is W203, and the amino acid after substitution is Y (112) An amino acid substitution in which the mutation point is F223, and the amino acid after substitution is Y, M, L, W, V, H, G or A (113) An amino acid substitution in which the mutation point is R238, and the amino acid after substitution is A, D, V, G, H or S (114) An amino acid substitution in which the mutation point is F251, and the amino acid after substitution is H, N, C, M, R, S, A, T, L, P, G, V or Q (115) An amino acid substitution in which the mutation point is V252, and the amino acid after substitution is M, L, T or C (116) An amino acid substitution in which the mutation point is N253, and the amino acid after substitution is T, V, K, C or R (117) An amino acid substitution in which the mutation point is Y256, and the amino acid after substitution is L, V or I (118) An amino acid substitution in which the mutation point is G257, and the amino acid after substitution is A or C (119) An amino acid substitution in which the mutation point is W258, and the amino acid after substitution is Y, F or N (120) An amino acid substitution in which the mutation point is T273, and the amino acid after substitution is N (121) An amino acid substitution in which the mutation point is G275, and the amino acid after substitution is A, C, S, V, K, I, F, H, R, L, P, Q, Y, N, M or T (122) An amino acid substitution in which the mutation point is N276, and the amino acid after substitution is G, M, Q or H (123) An amino acid substitution in which the mutation point is H277, and the amino acid after substitution is N, S, Q, C, E, K, D, I, R, M, P, L, W, V, Y, G, F or T (124) An amino acid substitution in which the mutation point is Y278, and the amino acid after substitution is P or D (125) An amino acid substitution in which the mutation point is H279, and the amino acid after substitution is N (126) An amino acid substitution in which the mutation point is S284, and the amino acid after substitution is C (127) An amino acid substitution in which the mutation point is M288, and the amino acid after substitution is V, Q or T (128) An amino acid substitution in which the mutation point is V290, and the amino acid after substitution is T, C, L, M, A, S or N (129) An amino acid substitution in which the mutation point is Y291, and the amino acid after substitution is H, T, E or G (130) An amino acid substitution in which the mutation point is W298, and the amino acid after substitution is F, Y, I, L or M (131) An amino acid substitution in which the mutation point is S299, and the amino acid after substitution is N or P (132) An amino acid substitution in which the mutation point is Y302, and the amino acid after substitution is L, H, M, V, C, T, P, S or W (133) An amino acid substitution in which the mutation point is S303, and the amino acid after substitution is I, Q, D, H or E (134) An amino acid substitution in which the mutation point is F305, and the amino acid after substitution is W, H or Y Among the above amino acid substitutions, the following amino acid substitutions provide a high degree of conversion into deamidase, and thus are more preferable.

R5Q, R5P, R5C, R5M, R5I, R5V, R5Y, R5F, R5S, R5N, R5T, R5G

Y34H, Y34M

W59K, W59E

S61T, S61V, S61Y, S61D, S61I, S61L, S61N, S61E, S61M, S61F, S61W, S61Q, S61P, S61H, S61K

Y62D, Y62P

G63D, G63Q, G63Y, G63R, G63K, G63H, G63P, G63M, G63N, G63C, G63F, G63L, G63W, G63T, G63V, G63S

V65C, V65T, V65K

G66W, G66K

T68P, T68H

W69Y, W69D, W69P

Q74R, Q74P

F85Y, F85W, F85L, F85I, F85Q, F85C, F85T, F85A, F85V, F85S, F85R, F85H, F85N

F108Q, F108C, F108E, F108S, F108N

F117C, F117I, F117W, F117V, F117A, F117G, F117T, F117N

Y198F, Y198H, Y198L, Y198S, Y198M, Y198I

S199Q, S199P

K200Y, K200M, K200I, K200R, K200L, K200V

H201K, H201R, H201M, H201L, H201Q

F202Y, F202M, F202H, F202V, F202C

W203Y

F223Y, F223M, F223L, F223W, F223V, F223H, F223G, F223A

R238A, R238D, R238V, R238G, R238H, R238S

F251H, F251N, F251C, F251M, F251R, F251S, F251A, F251T, F251L, F251P, F251G, F251V, F251Q

V252M, V252L, V252T, V252C

N253T, N253V, N253K, N253C, N253R

Y256L, Y256V, Y256I

G257A, G257C

W258Y, W258F, W258N

T273N

G275A, G275C, G275S, G275V, G275K, G275I, G275F, G275H, G275R, G275L, G275P, G275Q, G275Y, G275N, G275M, G275T

N276G, N276M, N276Q, N276H

H277N, H277S, H277Q, H277C, H277E, H277K, H277D, H277I, H277R, H277M, H277P, H277L, H277W, H277V, H277Y, H277G, H277F, H277T

Y278P, Y278D

H279N

S284C

M288V, M288Q, M288T

V290T, V290C, V290L, V290M, V290A, V290S, V290N

Y291H, Y291T, Y291E, Y291G

W298F, W298Y, W298I, W298L, W298M

S299N, S299P

Y302L, Y302H, Y302M, Y302V, Y302C, Y302T, Y302P, Y302S, Y302W

S303I, S303Q, S303D, S303H, S303E

F305W, F305H, F305Y

The following amino acid substitutions provide a still higher degree of conversion into deamidase, and thus are more preferable.

R5Y, R5F, R5S, R5N, R5T, R5G

Y34M

S61T, S61V, S61Y, S61D, S61I, S61L, S61N, S61E, S61M, S61F, S61W, S61Q, S61P, S61H, S61K

Y62P

G63D, G63Q, G63Y, G63R, G63K, G63H, G63P, G63M, G63N, G63C, G63F, G63L, G63W, G63T, G63V, G63S

V65C, V65T, V65K

G66K

T68P, T68H

W69D, W69P

F85L, F851, F85Q, F85C, F85T, F85A, F85V, F85S, F85R, F85H, F85N

F108C, F108E, F108S, F108N

F117C, F1171, F117W, F117V, F117A, F117G, F117T, F117N

Y198L, Y198S, Y198M, Y198I

S199Q, S199P

K200Y, K200M, K200I, K200R, K200L, K200V

H201K, H201R, H201M, H201L, H201Q

F202M, F202H, F202V, F202C

W203Y

F223M, F223L, F223W, F223V, F223H, F223G, F223A

R238H, R238S

F251N, F251C, F251M, F251R, F251S, F251A, F251T, F251L, F251P, F251G, F251V, F251Q

V252L, V252T, V252C

N253T, N253V, N253K, N253C, N253R

Y256L, Y256V, Y256I

G257A, G257C

W258Y, W258F, W258N

T273N

G275C, G275S, G275V, G275K, G275I, G275F, G275H, G275R, G275L, G275P, G275Q, G275Y, G275N, G275M, G275T

N276G, N276M, N276Q, N276H

H277S, H277Q, H277C, H277E, H277K, H277D, H277I, H277R, H277M, H277P, H277L, H277W, H277V, H277Y, H277G, H277F, H277T

Y278P, Y278D

M288Q, M288T

V290M, V290A, V290S, V290N

Y291T, Y291E, Y291G

W298F, W298Y, W298I, W298L, W298M

S299P

Y302L, Y302H, Y302M, Y302V, Y302C, Y302T, Y302P, Y302S, Y302W

F305H, F305Y

The following amino acid substitutions provide a particularly high degree of conversion into deamidase, and thus are particularly preferable.

S61Y, S61D, S61I, S61L, S61N, S61E, S61M, S61F, S61W, S61Q, S61P, S61H, S61K

Y62P

G63D, G63Q, G63Y, G63R, G63K, G63H, G63P, G63M, G63N, G63C, G63F, G63L, G63W, G63T, G63V, G63S

V65T, V65K

G66K

T68P, T68H

W69D, W69P

F85H, F85N

F117G, F117T, F117N

Y198S, Y198M, Y198I

S199P

K200M, K200I, K200R, K200L, K200V

H201M, H201L, H201Q

F202V, F202C

W203Y

F223W, F223V, F223H, F223G, F223A

F251L, F251P, F251G, F251V, F251Q

N253T, N253V, N253K, N253C, N253R

Y256L, Y256V, Y256I

G257C

W258N

G275V, G275K, G275I, G275F, G275H, G275R, G275L, G275P, G275Q, G275Y, G275N, G275M, G275T

N276G, N276M, N276Q, N276H

H277S, H277Q, H277C, H277E, H277K, H277D, H277I, H277R, H277M, H277P, H277L, H277W, H277V, H277Y, H277G, H277F, H277T

Y278P, Y278D

M288T

V290S, V290N

Y291G

W298Y, W298I, W298L, W298M

F305Y

Specific examples of the modified enzyme of the present invention include transglutaminase comprising an amino acid sequence of any of SEQ ID NOs: 2 to 10 (corresponding to an R26N variant, an R26Y variant, an R26S variant, an E28N variant, an E28G variant, an E28F variant, an E28Y variant, an E58R variant and an E58L variant, in this order). As will be described in the Examples below, it has been confirmed that these variants have a reduced temperature stability and an improved oxidation resistance.

Generally, when the amino acid sequence of a given protein is partially changed by mutation, the protein obtained after the mutation may have the same function as that before the mutation. In other words, it is sometimes observed that a mutation in the amino acid sequence of a given protein does not substantially affect the function of the resulting protein and in these proteins, the function is maintained before and after the mutation. In addition, it is highly probable that two proteins exhibit equivalent properties when sharing high identity in their amino acid sequences. In light of common technical knowledge of these things, a modified enzyme can be considered to be an enzyme that is substantially identical to the above-described modified enzyme (or can be referred to as a substantially identical transglutaminase), with the proviso that such a modified enzyme has an amino acid sequence that is not completely identical (i.e., does not have a sequence identity of 100%) to that of any of the above-described modified enzymes, that is, an "amino acid sequence comprising any one of amino acid substitutions (1) to (134) in the amino acid sequence represented by SEQ ID NO: 1 (specific examples of which amino acid sequence are those represented by SEQ ID NOs: 2 to 10)" and displays a high level of sequence identity therewith, and has a desired change in characteristics. Such a sequence identity is 70% or more, 80% or more, 82% or more, 85% or more, 90% or more, 93% or more, 95% or more, 98% or more, or 99% or more. The higher the identity, the better. Therefore, the sequence identity of the most preferable embodiment.

When the above modified enzymes and substantially identical transglutaminases are compared, a slight difference in amino acid sequence is recognized, provided that the difference in amino acid sequence occurs at a position other than the position where the amino acid substitution is made. Thus, for example, if the reference for identity is the amino acid sequence of SEQ ID NO: 2, a difference in amino acid sequence occurs at a position other than N at position 26. If the reference for identity is the amino acid sequence of SEQ ID NO: 3, a difference in amino acid sequence occurs at a position other than Y at position 26. If the reference for identity is the amino acid sequence of SEQ ID NO: 4, a difference in amino acid sequence occurs at a position other than S at position 26. If the reference for identity is the amino acid sequence of SEQ ID NO: 5, a difference in amino acid sequence occurs at a position other than N at position 28. If the reference for identity is the amino acid sequence of SEQ ID NO: 6, a difference in amino acid sequence occurs at a position other than G at position 28. If the reference for identity is the amino acid sequence of SEQ ID NO: 7, a difference in amino acid sequence occurs at a position other than F at position 28. If the reference for identity is the amino acid sequence of SEQ ID NO: 8, a difference in amino acid sequence occurs at a position other than Y at position 28. If the reference for identity is the amino acid sequence of SEQ ID NO: 9, a difference in amino acid sequence occurs at a position other than R at position 58. If the reference for identity is the amino acid sequence of SEQ ID NO: 10, a difference in amino acid sequence occurs at a position other than a position other than L at position 58. In other words, in the amino acid sequences showing the above identity (70% or more, 80% or more, 82% or more, 85% or more, 90% or more, 93% or more, 95% or more, 98%, or 99% or more) to the amino acid sequence of SEQ ID NO: 2, the amino acid at position 26 is N. Similarly, in the amino acid sequences showing the above identity to the amino acid sequence of SEQ ID NO: 3, the amino acid at position 26 is Y. In the amino acid sequences showing the above identity to the amino acid sequence of SEQ ID NO: 4, the amino acid at position 26 is S. In the amino acid sequences showing the above identity to the amino acid sequence of SEQ ID NO: 5, the amino acid at position 28 is N. In the amino acid sequences showing the above identity to the amino acid sequence of SEQ ID NO: 6, the amino acid at position 28 is G. In the amino acid sequences showing the above identity to the amino acid sequence of SEQ ID NO: 7, the amino acid at position 28 is F. In the amino acid sequences showing the above identity to the amino acid sequence of SEQ ID NO: 8, the amino acid at position 28 is Y. In the amino acid sequences showing the above identity to the amino acid sequence of SEQ ID NO: 9, the amino acid at position 58 is R. In the amino acid sequences showing the above identity to the amino acid sequence of SEQ ID NO: 10, the amino acid at position 58 is L.

Here, a "slightly different amino acid sequence" results from amino acid deletion, substitution, addition, insertion, or a combination thereof. This means that in typical cases, a given amino acid sequence is mutated (or changed) by deletion or substitution of one to several (for example, up to three, five, seven, ten) amino acids constituting the amino acid sequence, or addition or insertion of one to several (for example, up to three, five, seven, ten) amino acids, or a combination thereof. A "slightly different amino acid sequence" preferably results from a conservative amino acid substitution. Here, by "conservative amino acid substitution" is meant that a certain amino acid residue is substituted with an amino acid residue of which the side chain is similar in properties. Amino acid residues are classified into several families, on the basis of their side chains, such as families of amino acids having basic side chains (for example, lysine, arginine, histidine), acidic side chains (for example, aspartic acid, glutamic acid), uncharged polar side chains (e.g. glycine, asparagine, glutamine, serine, threonine, tyrosine, cysteine), nonpolar side chains (for example, alanine, valine, leucine, isoleucine, proline, phenylalanine, methionine, tryptophan), β-branched side chains (for example, threonine, valine, isoleucine), and aromatic side chains (for example, tyrosine, phenylalanine, tryptophan, histidine). The conservative amino acid substitution preferably is a substitution between amino acid residues within the same family. In connection with this, it is known that the active residue of Streptomyces mobaraensis-derived transglutaminase (SEQ ID NO: 1) is cysteine at position 64, and thus mutation should be made so that there is no influence on these amino acid residues.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an equivalent nucleic acid sequence, for example, BLAST nucleotide search with score=100 and word length=12 may be carried out by the NBLAST program. In order to obtain an equivalent amino acid sequence, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see www.ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. The identity between two nucleic acid sequences can be determined by using the GAP program in the GCG software package (available at www.gcg.com), with the gap weight of 50, and the gap length weight of 3.

Typically, transglutaminase comprising the amino acid sequence of SEQ ID NO: 1, that is, *Streptomyces mobaraensis* derived transglutaminase is mutated (subjected to any of the above amino acid substitutions (1) to (134)) to obtain the modified enzyme of the present invention. The above substantially identical transglutaminase can be obtained by further adding a mutation to the mutated (any of the above amino acid substitutions (1) to (134)) transglutaminase comprising the amino acid sequence of SEQ ID NO: 1, adding an equivalent mutation to transglutaminase comprising an amino acid sequence having a high identity to the amino acid sequence of SEQ ID NO: 1, such as transglutaminase derived from a strain of the same species and genus as the *Streptomyces mobaraensis* strain that produces transglutaminase comprising the amino acid sequence of SEQ ID NO: 1, or further adding a mutation to the mutated transglutaminase obtained by the mutation. The "equivalent mutation" herein involves substitution of an amino acid residue corresponding to the amino acid residue at the mutation point (mutation point in any of the above amino acid substitutions (1) to (134)) in the present invention, in an amino acid sequence having a high identity to the amino acid sequence of SEQ ID NO: 1. Examples of transglutaminases comprising an amino acid sequence having a high identity to the amino acid sequence of SEQ ID NO: 1 can include transglutaminase derived from *Streptomyces mobaraensis* (previously classified as *Streptoverticillium ladakanum*) and having an amino acid sequence of SEQ ID NO: 11 (amino acid sequence identity: 93%); transglutaminase derived from *Streptomyces albireticuli* and having an amino acid sequence of SEQ ID NO: 12 (amino acid sequence identity: 82%); transglutaminase derived from *Streptomyces luteireticuli* and having an amino acid sequence of SEQ ID NO: 13 (amino acid sequence identity: 82%); transglutaminase derived from *Streptomyces cinnamoneus* and having an amino acid sequence of SEQ ID NO: 14 (amino acid sequence identity: 81%); transglutaminase derived from *Streptomyces platensis* and having an amino acid sequence of SEQ ID NO: 15 (amino acid sequence identity: 80%); and transglutaminase derived from *Streptomyces hygroscopicus* and having an amino acid sequence of SEQ ID NO: 16 (amino acid sequence identity: 80%).

Herein, the term "corresponding" when used for an amino acid residue in the present specification means contributing equally to exhibition of functions among proteins (enzymes) being compared. For example, when an amino acid sequence for comparison to the base amino acid sequence (that is, the amino acid sequence set forth in SEQ ID NO: 1) is aligned while considering partial homology of the primary structure (that is, an amino acid sequence) so that the most appropriate comparison can be achieved (in this event, the alignment may be optimized by introducing gaps if necessary), an amino acid located at a position corresponding to a specific amino acid in the base amino acid sequence can be specified as a "corresponding amino acid". The "corresponding amino acid" can also be specified by comparison between conformations (three-dimensional structures) in place of or in addition to the comparison between primary structures. Utilization of conformational information can give highly credible comparison results. In this case, a technique of performing an alignment with comparing atomic coordinates of conformations of a plurality of enzymes can be adopted. Conformational information of an enzyme to be mutated is available from, for example, the Protein Data Bank (www.pdbj.org/index_j.html).

One example of a method for determination of a protein conformation by the X-ray crystal structure analysis will be shown below.

(1) A protein is crystallized. Crystallization is essential to determine a conformation, and in addition, crystallization is industrially useful as a purification method of a protein at high purity and a stable preservation method of a protein at high density. In this case, a protein to which a substrate as a ligand or its analogous compound is bound may be preferably used for crystallization.

(2) The prepared crystal is irradiated with X ray to collect diffraction data. There are many cases that a protein crystal is damaged due to X ray irradiation and the diffraction ability is deteriorated. In such cases, a low-temperature measurement technique of rapidly cooling the crystal to about −173° C. and collecting diffraction data in the state has been recently prevailed. In addition, ultimately, synchrotron orbit radiation having high luminance is utilized to collect high resolution data that is used for structural determination.

(3) In addition to the diffraction data, phase information is necessary in order to perform the crystal structure analysis. When a crystal structure of an analogous protein to a desired protein is unknown, it is impossible to determine the structure in a molecular substitution method, and a phase problem has to be solved by a heavy-atom isomorphous replacement method. The heavy-atom isomorphous replacement method is a method in which a metallic atom having a high atomic number such as mercury or platinum is introduced into a crystal and contribution of a large X ray scattering ability of such a metallic atom to X ray diffraction data is utilized to collect phase information. The determined phase is possibly improved by smoothing an electron density of a solvent region in the crystal. Since a water molecule in the solvent region has large fluctuation, the electron density is hardly observed, and thus adjusting the electron density in this region to close to 0 makes it possible to approach the real electron density, which results in improving a phase. When plural molecules are contained in an asymmetrical unit, equation of electron densities of these molecules makes it possible to more significantly improve a phase. A model of a protein is fit to an electron density map calculated using the phase improved as described above. This process is performed on computer graphics using a program such as QUANTA made by MSI Co. (USA). After the process, structural precision is performed using a program such as X-PLOR made by MSI Co. to complete the structure analysis. When a crystal structure of an analogous protein to a desired protein is known, it can be determined in a molecular substitution method using the atomic coordinate of the known protein. Molecular substitution and structure refinement can be performed using a program such as CNS_SOLVE ver.11.

2. Nucleic Acid Coding for Modified Transglutaminase Etc.

The second aspect of the present invention provides a nucleic acid relating to the modified enzyme of the invention. That is, provided are a gene coding for the modified enzyme, a nucleic acid that can be used as a probe for identifying a nucleic acid coding for the modified enzyme, and a nucleic acid that can be used as a primer for amplifying or mutating a nucleic acid coding for the modified enzyme.

The gene coding for a modified enzyme is typically used in preparation of the modified enzyme. According to a genetic engineering procedure using the gene coding for a modified enzyme, a modified enzyme in a more homogeneous state can be obtained. Further, the method can be a preferable method also in the case of preparing a large amount of a modified enzyme. Note that uses of the gene coding for a modified enzyme are not limited to preparation of a modified enzyme. For example, the nucleic acid can also be used as a tool for an experiment intended for clarification of action mechanisms of a modified enzyme or a tool for designing or preparing a further modified form of an enzyme.

The "gene coding for a modified enzyme" herein refers to a nucleic acid capable of obtaining the modified enzyme when it is expressed, and includes, as a matter of course of a nucleic acid having a base sequence corresponding to the amino acid sequence of the modified enzyme, also a nucleic acid obtained by adding a sequence that does not code for an amino acid sequence to such a nucleic acid. Degeneracy of a codon is also considered.

Examples of the sequence (base sequence) of the gene coding for the modified enzyme are shown in SEQ ID NOs: 18 to 26. These sequences encode variants which will be indicated in the Examples below.

SEQ ID NO: 18: R26N variant
SEQ ID NO: 19: R26Y variant
SEQ ID NO: 20: R26S variant
SEQ ID NO: 21: E28N variant
SEQ ID NO: 22: E28G variant
SEQ ID NO: 23: E28F variant
SEQ ID NO: 24: E28Y variant
SEQ ID NO: 25: E58R variant
SEQ ID NO: 26: E58L variant When the gene of the present invention is expressed in a host, a gene construct in which a sequence encoding a pro-peptide (pro-sequence) is added to the 5' end side of any of the above sequences (for example, any of SEQ ID NOs: 18 to 26) is usually introduced into the host, for example, for stabilizing the structure of the modified enzyme as an expression product. When the gene of the present invention is expressed as a secretory protein, a gene contract in which a sequence encoding a pre-sequence (signal sequence) is added to the 5' end side of the sequence encoding the pro-sequence is provided. When the gene construct is used, the gene is expressed as a prepro-type transglutaminase in which the pre-sequence and the pro-sequence are linked, and then the expression product is subjected to cleavage of the pre-sequence (conversion to a pro-type transglutaminase) and cleavage of the pro-sequence, so that a mature trans-glutaminase is obtained. As the sequence encoding the pre-sequence and the sequence encoding the pro-sequence, the original sequences, that is, the sequences of the reference transglutaminase (transglutaminase before modification) are preferably used. A specific example of the pre-sequence is SEQ ID NO: 27 (pre-sequence of *Streptomyces mobaraensis* derived transglutaminase); a specific example of the pro-sequence is SEQ ID NO: 28 (pro-sequence of *Streptomyces mobaraensis* derived transglutaminase); a specific example of the sequence encoding the pre-sequence is SEQ ID NO: 29 (sequence encoding the pre-sequence of *Streptomyces mobaraensis* derived transglutaminase); and a specific example of the sequence encoding the pro sequence is SEQ ID NO: 30 (sequence encoding the pro-sequence of *Strep-tomyces mobaraensis* derived transglutaminase).

The nucleic acid of the present invention can be prepared in an isolated state by use of a standard genetic engineering technique, molecular biological technique, biochemical technique, chemical synthesis and the like in reference to the present specification or the sequence information disclosed in the appended sequence listing.

Another embodiment of the present invention provides a nucleic acid different in a base sequence in a part (herein-after also referred to as a "homologous nucleic acid", and a base sequence defining a homologous nucleic acid is also referred to as a "homologous base sequence") as compared to the base sequence of the gene coding for the modified enzyme of the invention, although functions of a protein coded by the nucleic acid are equal. An example of the homologous nucleic acid includes a DNA composed of a base sequence containing substitution, deletion, insertion, addition or inversion of 1 to several bases on the basis of the base sequence of the nucleic acid coding for the modified enzyme of the present invention and coding for a protein having activity which is characteristic to the modified enzyme (i.e. transglutaminase activity). Substitution or dele-tion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

The homologous nucleic acid has, for example, a sequence identity of 60% or more, preferably 70% or more, more preferably 80% or more, even more preferably 85% or more, further preferably about 90% or more, still further preferably 95% or more, most preferably 99% or more, with a reference base sequence.

Such a homologous nucleic acid as described above can be obtained by, for example, a restriction enzyme treatment, a treatment with exonuclease, DNA ligase, etc., and intro-duction of mutation by a site directed mutation introduction method (Molecular Cloning, Third Edition, Chapter 13, Cold Spring Harbor Laboratory Press, New York), and random mutation introduction method (Molecular Cloning, Third Edition, Chapter 13, Cold Spring Harbor Laboratory Press, New York). The homologous nucleic acid can be obtained also in other methods such as exposure to ultra-violet radiation.

Another embodiment of the present invention relates to a nucleic acid having a base sequence complementary to the base sequence of the gene coding for the modified enzyme of the invention. Another embodiment of the present inven-tion provides a nucleic acid having a base sequence with an identity of at least about 60%, 70%, 80%, 90%, 95%, 99%, or 99.9% to the base sequence of the gene coding for the modified enzyme of the invention or a base sequence complementary to the base sequence.

Another embodiment of the present invention relates to a nucleic acid having a base sequence hybridizing to a base sequence complementary to the base sequence of the gene coding for the modified enzyme of the invention or its homologous base sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include condi-tions of using a hybridization liquid (50% formamide, 10×SSC (0.15 M NaCl, 15 mM sodium citrate, pH 7.0), a 5×Denhardt solution, 1% SDS, 10% dextran sulfate, 10 μg/ml of modified salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 µg/ml of modified salmon sperm DNA, and a 50 mM phosphate buffer (pH 7.5) as a hybridization liquid.

Another embodiment of the present invention provides a nucleic acid (nucleic acid fragment) having a part of the base sequence of the gene coding for the modified enzyme of the invention or a base sequence complementary to the base sequence. Such a nucleic acid fragment can be used in detection, identification, and/or amplification of a nucleic acid having the base sequence of the gene coding for the modified enzyme of the present invention. For example, the nucleic acid fragment is designed so as to at least contain a part being hybridized to a sequential nucleotide moiety (for example, about 10 to about 100 bases length, preferably about 20 to about 100 bases length, more preferably about 30 to about 100 bases length) in the base sequence of the gene coding for the modified enzyme of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a modified enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a 2 phage or an altered form thereof, and pBR322 or an altered form thereof (e.g., pB325, pAT153, pUC8), etc. as a vector having *Escherichia coli* as a host, pYepSec 1, pMFa, pYES2 and pPIC3.5K as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed in a standard recombinant DNA technique (for example, a known method of using a restriction enzyme and a DNA ligase, which can be referred in Molecular Cloning, Third Edition, 1.84, Cold Spring Harbor Laboratory Press, New York).

From the viewpoint of ease of handling, the host cell can be microorganisms such as an *aspergillus* (e.g., *Aspergillus oryzae*), a *bacillus* bacterium (e.g., *Bacillus subtilis, Bacillus licheniformis*, or *Bacillus aminoliquaciens*), a brevibacillus bacterium (e.g., *Brevibacillus choshinensis*), *E. coli* (*Escherichia coli*) and budding yeast (*Saccharomyces cerevisiae*). Any host cell can be used so long as it allows replication of the recombinant DNA and expression of the gene of the modified enzyme. Preferably, *E. coli* (*Escherichia coli*) and budding yeast (*Saccharomyces cerevisiae*) can be used. A microorganism of the genus *Streptomyces* (e.g.,

*Streptomyces morabaensis*) can also be used as the host. An example of *E. coli* can be *E. coli* BL21 (DE3) when a T7 promoter is used, and can be *E. coli* JM109 otherwise. Examples of budding yeast can include budding yeast SHY2, budding yeast AH22 and budding yeast INVSc1 (Invitrogen).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, electroporation (Potter, H. et al., Proc. Natl. Acad. Sci. U.S.A. 81, 7161-7165 (1984)), and lipofectin (Felgner, P. L. et al., Proc. Natl. Acad. Sci. U.S.A. 84, 7413-7417 (1984)). The microorganism of the present invention can be used for producing the modified enzyme of the invention.

3. Enzyme Preparation Containing Modified Transglutaminase

The modified enzyme of the present invention is provided, for example, in the form of an enzyme preparation. The enzyme preparation may contain, in addition to the active ingredient (modified enzyme of the present invention), an excipient, a buffer, a suspending agent, a stabilizer, a preservative, an antiseptic, physiological saline, various proteins, degradation products of various proteins, various extracts, various salts, various antioxidants, cysteine, glutathione, sodium glutamate, sodium inosinate, sodium guanylate, calcined shell calcium, silicon dioxide, or the like. As the excipient, starch, dextrin, maltose, trehalose, lactose, D-glucose, sorbitol, D-mannitol, sucrose, glycerol and the like can be used. As the buffer agent, phosphates, citrates, acetates, and the like can be used. As the stabilizer, propylene glycol, ascorbic acid, and the like can be used. As the preservative, phenol, benzalkonium chloride, benzyl alcohol, chlorobutanol, methylparaben, and the like can be used. As the antiseptic, benzalkonium chloride, paraoxybenzoic acid, chlorobutanol, and the like can be used. Examples of proteins include soy protein, wheat protein, corn protein, milk protein, and animal-derived protein. Examples of extracts include meat extracts, plant extracts, and yeast extracts. Examples of salts include chloride salts, phosphates, polyphosphates, pyrophosphates, citrates, lactates, and carbonates. Examples of antioxidants include L-ascorbic acid salts, and sodium bisulfite. The shape of the enzyme preparation of the present invention is not particularly limited, and is, for example, powder, granule, liquid, capsule or the like.

4. Methods for Preparation of Modified Transglutaminases

A further aspect of the present invention relates to a method for preparing a modified enzyme according to the present invention. In an embodiment of the method for preparation according to the present invention, modified enzymes of the present invention are prepared by genetic engineering procedures. In this embodiment, a nucleic acid encoding the amino acid sequence of the modified enzyme of the present invention (for example, any of SEQ ID NOs: 2 to 10) is prepared (step (I)). Here, a "nucleic acid encoding a particular amino acid sequence" gives, upon its expression, a polypeptide having the amino acid sequence encoded thereby, and includes not only a nucleic acid consisting of a base sequence corresponding to the amino acid sequence, but also a nucleic acid that may have an additional sequence added thereto, which may or may not encode an amino acid sequence. The degeneracy of codons is also taken into consideration. A "nucleic acid encoding the amino acid sequence of the modified transglutaminase of the present invention" can be prepared in an isolated state, for example, by standard genetic engineering, molecular biological, and biochemical procedures, with reference to the sequence information disclosed in the specification and accompanying sequence listing. As mentioned above, the amino acid sequence of the modified transglutaminase of the present invention results from a particular mutation of the amino acid sequence of the reference transglutaminase. Therefore, "a nucleic acid encoding the amino acid sequence of the modified transglutaminase of the present invention" can also be obtained by applying a required mutation to the gene encoding the reference transglutaminase. A large number of methods for site-specific base sequence substitution are known in the art (see, for example, Molecular Cloning, Third Edition, Cold Spring Harbor Laboratory Press, New York), and from among these, suitable methods can be selected and used. As a site-specific mutagenesis method, site-specific saturation mutagenesis of amino acids can be employed. The site-specific saturation mutagenesis of amino acids is a "Semi-rational, semi-random" method in which the position involved in the desired function of a given protein is estimated on the basis of the three-dimensional structure of the protein, which is then subjected to amino acid saturation mutagenesis (J. Mol. Biol. 331, 585-592 (2003)). For example, site-specific saturation mutagenesis of amino acids can be performed by using kits, such as Quick change (Stratagene), and overlap extention PCR (Nucleic Acid Res. 16, 7351-7367 (1988)). As the DNA polymerase for use in the PCR, for example, Taq polymerase can be employed. Preferably, use is made of high-accuracy DNA polymerases such as KOD-PLUS- (Toyobo Co., Ltd.) and Pfu turbo (Stratagene).

Following the step (I), the prepared nucleic acid is expressed (step (II)). For example, firstly, an expression vector inserted with the above described nucleic acid is prepared and a host cell is transformed using this constructed vector.

Then, a transformant is cultured under the condition of producing a modified enzyme that is an expressed product. Culture of the transformant may follow a general method. An assimilable carbon compound may be used as a carbon source used for a medium, and examples such as glucose, sucrose, lactose, maltose, molasses, and pyruvic acid are used. An available nitrogen compound may be used as a nitrogen source, and examples such as peptone, meat extract, yeast extract, casein hydrolysate, and soybean bran alkali extract are used. Other than those substances, phosphate, carbonate, sulfate, salts of magnesium, calcium, potassium, iron, manganese and zinc, specific amino acids, specific vitamins, and the like are used according to necessity.

On the other hand, a culture temperature can be set within the range from 30 to 40° C. (preferably at around 33-37° C.). A culture time can be set by considering growing characteristics of a transformant to be cultured and production characteristics of a modified enzyme. A pH of a medium is set within the range wherein a transformant grows and an enzyme is produced. The pH of a medium is preferably set at about 6.0 to 9.0 (preferably at around pH 7.0).

Subsequently, the expressed product (modified enzyme) is collected (step (III)). A culture liquid containing fungas bodies after culture may be used as an enzyme solution directly or after undergoing condensation, removal of impurities, or the like, but the expressed product is generally once collected from the culture liquid or fungas bodies. When the expressed product is a secretion type protein, it can be collected from the culture liquid, and in other cases, the expressed product can be collected from cells. In the case of collecting from the culture liquid, for example, an undissolved substance is removed by filtration and centrifugation on a culture supernatant, and then, a purified product of a modified enzyme can be obtained by separation and purification in combination of vacuum concentration, membrane concentration, salting out using ammonium sulfate or sodium sulfate, fractional precipitation by methanol, ethanol, or acetone, dialysis, heating treatment, isoelectric treatment, various kinds of chromatography such as gel filtration, adsorption chromatography, ion exchange chromatography, and affinity chromatography (for example, gel filtration with Sephadex gel (GE Healthcare Life Sciences), etc., DEAE sepharose CL-6B (GE Healthcare Life Sciences), octyl sepharose CL-6B (GE Healthcare Life Sciences), CM sepharose CL-6B (GE Healthcare Life Sciences)). On the other hand, in the case of collecting the expressed product from cells, a culture liquid is subjected to filtration, centrifugation, or the like, to thus obtain the cells, then the cells are crushed by a mechanical method such as a pressure treatment and an ultrasonic treatment, or an enzymatic method with a lysozyme or the like, thereafter carrying out separation and purification in the same manner as described above, and a purified product of a modified enzyme can be thus obtained.

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

Generally, genetic expression and collection of the expressed product (modified enzyme) are carried our using an appropriate host-vector system as described above, but a cell-free synthesis system may also be employed. Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disruptor that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al.: Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make each amino acid combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

Examples

<Search for Effective Mutation Points to Improve Properties>

For obtaining highly useful modified transglutaminases, an attempt was made to improve the enzyme function (reduction in temperature stability, improvement in heat resistance, improvement in oxidation resistance, improvement in reactivity, or conversion into deamidase) of *Streptomyces mobaraensis* derived transglutaminase (wild type enzyme; SEQ ID NO: 1) by using protein engineering. First, for introducing a mutation due to an amino acid substitution, a CASTing library (for example, see Angew Chem Int Ed Engl. 2006 Feb. 13; 45 (8): 1236-41) and alanine scanning (Ala scanning) (for example, J Mol Biol 1995 Feb. 17; 246 (2): 317-30) were utilized to select candidate mutation points. Next, a mutation was introduced into each mutation point by the following method to prepare a mutated enzyme.

1. Preparation of Mutated Enzyme 1-1. Introduction of Mutation (1) A PCR primer is designed for introduction of a mutation.
(2) A primer set for each mutation point is used for PCR using plasmid pET20b in which transglutaminase gene (SEQ ID NO: 17) has been incorporated as a template (15 cycles of reactions at 98° C. for 1 minute, at 98° C. for 10 seconds, at 60° C. for 15 seconds and at 68° C. for 2 minutes are performed, and the resultant product is reacted at 68° C. for 5 minutes, and then allowed to stand at 4° C.).
(3) DpnI (1.5 μL/tube) is added to the PCR reaction solution (25 μL/tube) for treatment (37° C., 3 hours or longer).
(4) Ligation treatment (16° C., overnight) is performed using T4 kinase.
(5) *E. coli* BL21 (DE3) is transformed with the ligation reaction solution (11 μL/tube), and cultured in an LB medium containing ampicillin (37° C., overnight).

1-2. Obtainment of Enzyme Extract (1) A strain into which a mutation has been introduced (mutated strain) is inoculated into a TB medium containing ampicillin, and cultured at 33° C. for 48 hours. IPTG (final concentration: 0.1 mM) is added 24 hours after the start of the culture.

(2) After centrifugation of the culture solution (3,000 g×10 minutes), the supernatant is removed, and the bacterial cells are recovered.
(3) A bacteriolytic agent is added to lyse the bacterial cells.
(4) After centrifugation of the bacterial lysate (3,000 g×10 minutes), the supernatant is recovered and used as an enzyme extract.

1-3. Maturation (Removal of Pro-Peptide Sequence)

(1) Equal amounts of the enzyme extract and a 2 mg/mL protease (Dispase) solution are mixed to cause a reaction (30° C., 2 hours or longer).
(2) After centrifugation of the mixed solution (3,000 g×10 minutes), the supernatant is recovered and used as a maturated enzyme.

2. Evaluation of Property of Mutated Enzyme

The following activity measurement methods were used to evaluate the properties of each prepared mutated enzyme.

<Activity Measurement Method>

The maturated enzyme is diluted to an appropriate concentration with 200 mM Tris-HCl pH 6.0 (sample solution). To 10 μL of the sample solution, 100 μL of the substrate solution (R-1) is added, and the solution mixture is mixed and caused to react at 37° C. for 10 minutes. A coloring solution (R-2) (100 μL) was added to stop the reaction and form an Fe complex, and then the absorbance at 525 nm is measured. As a control, the absorbance of a previously heat-inactivated enzyme solution subjected to a similar reaction is measured, and the absorbance difference thereof from the sample solution is determined. Separately, a calibration curve is prepared using L-glutamic acid-γ-monohydroxamic acid instead of the enzyme solution, and the amount of hydroxamic acid produced is determined from the absorbance difference. The enzyme activity that produces 1 μmol of hydroxamic acid per minute is defined as one unit (1 U).

(Substrate Solution (R-1))

2-Amino-2-hydroxymethyl-1.3-propanediol (2.42 g), hydroxyammonium hydrochloride (0.70 g), reduced glutathione (0.31 g), and Z-Gln-Gly (benzyloxycarbonyl-L-glutaminylglycine) (1.01 g) were dissolved in distilled water to attain a total volume of 100 mL (pH 6.0).

(Substrate Solution (R-2))

Mixed are 30 mL of a 3M hydrochloric acid solution, 30 mL of a 12% trichloroacetic acid solution, and 30 mL of a 5% iron (III) chloride solution.

2-1. Evaluation of Temperature Stability/Heat Resistance

The matured enzyme is diluted twice with 200 mM Tris-HCl pH 6.0, and the diluted enzyme is treated at a predetermined temperature (20° C., 30° C., 40° C., 50° C. or 60° C.) for 30 minutes. The activity is measured after the treatment, and the residual activity rate is calculated by comparison with the activity before the treatment.

The residual activity rate and the value relative to the wild type in the case of the treatment at 50° C. for 30 minutes are calculated using the following formulas to identify amino acid substitutions effective for reducing the temperature stability and those effective for improving the heat resistance.

Residual activity rate (%)=(enzyme activity after heat treatment)/(enzyme activity before heat treatment)×100

Rate (%) relative to wild type=(residual activity rate of mutated enzyme)/(residual activity rate of wild-type enzyme)×100

FIG. 1 shows the evaluation results of the temperature stability. The following amino acid substitutions (1) to (33)

providing a rate (%), relative to the wild type, of 90% or less were determined to be effective.

(1) An amino acid substitution in which the mutation point is V6, and the amino acid after substitution is Q, I, M, S, C, K, L, H, F, G, N, P, R, W or Y (2) An amino acid substitution in which the mutation point is R26, and the amino acid after substitution is K, Q, M, H, Y, D, G, N, P or S (3) An amino acid substitution in which the mutation point is E28, and the amino acid after substitution is V, Q, W, R, K, M, N, F, G, L, P or Y (4) An amino acid substitution in which the mutation point is V30, and the amino acid after substitution is P, C, A, E, F, G, H, K, N, Q, R, W, Y or L (5) An amino acid substitution in which the mutation point is Y34, and the amino acid after substitution is A (6) An amino acid substitution in which the mutation point is Y42, and the amino acid after substitution is F, A, C, D, E, G, I, L, M, Q, S, T, V or W (7) An amino acid substitution in which the mutation point is E58, and the amino acid after substitution is Y, M, A, F, I, V, R, K, N, L, S, Q, G or H (8) An amino acid substitution in which the mutation point is W59, and the amino acid after substitution is R, N, Y, A, S, I, V, D, G or P (9) An amino acid substitution in which the mutation point is L60, and the amino acid after substitution is I, M, V, A, C, E, F, Q, S, T, W or Y

(10) An amino acid substitution in which the mutation point is Y62, and the amino acid after substitution is C, R, G, K or S

(11) An amino acid substitution in which the mutation point is V65, and the amino acid after substitution is N, L, M, F, W or Y

(12) An amino acid substitution in which the mutation point is V67, and the amino acid after substitution is L, N, A, C, M, Q or S

(13) An amino acid substitution in which the mutation point is T68, and the amino acid after substitution is C, L, A, S, M, F, N, Q or Y

(14) An amino acid substitution in which the mutation point is W69, and the amino acid after substitution is H, M, I, C, E, F, G, K, L, N, Q, R, S, T or V

(15) An amino acid substitution in which the mutation point is Q74, and the amino acid after substitution is W, D, G or K

(16) An amino acid substitution in which the mutation point is Y75, and the amino acid after substitution is R, Q, T or G

(17) An amino acid substitution in which the mutation point is T77, and the amino acid after substitution is M, H, E, C or G

(18) An amino acid substitution in which the mutation point is F85, and the amino acid after substitution is M

(19) An amino acid substitution in which the mutation point is F90, and the amino acid after substitution is C, M, H, L or V

(20) An amino acid substitution in which the mutation point is F108, and the amino acid after substitution is R, L, T, A, I, K, N or V

(21) An amino acid substitution in which the mutation point is F117, and the amino acid after substitution is M or L

(22) An amino acid substitution in which the mutation point is S199, and the amino acid after substitution is G, M, N, K or V

(23) An amino acid substitution in which the mutation point is F202, and the amino acid after substitution is L or W

(24) An amino acid substitution in which the mutation point is W203, and the amino acid after substitution is F

(25) An amino acid substitution in which the mutation point is F254, and the amino acid after substitution is Y or M

(26) An amino acid substitution in which the mutation point is T273, and the amino acid after substitution is I, V, M, C, S, L, R, G, A, E, F, Y, D, K, W or H

(27) An amino acid substitution in which the mutation point is N276, and the amino acid after substitution is C, E, K, L, S, T or V

(28) An amino acid substitution in which the mutation point is Y278, and the amino acid after substitution is M, L, H, I, K, R, W, C, G, N, Q, S, T or V

(29) An amino acid substitution in which the mutation point is S284, and the amino acid after substitution is W, Y, M, F or N

(30) An amino acid substitution in which the mutation point is Y291, and the amino acid after substitution is I, W, L, A, C, K, N, Q, R, S or V

(31) An amino acid substitution in which the mutation point is S299, and the amino acid after substitution is I, Y, V, K, M, Q, A, F, G or E

(32) An amino acid substitution in which the mutation point is S303, and the amino acid after substitution is N, G, C, V, P or Y

(33) An amino acid substitution in which the mutation point is Y310, and the amino acid after substitution is C, M or I As more preferred amino acid substitutions, the following amino acid substitutions providing a rate (%), relative to the wild type, of 30% or less were identified.

V6S, V6C, V6K, V6L, V6H, V6F, V6G, V6N, V6P, V6R, V6W, V6Y

R26M, R26H, R26Y, R26D, R26G, R26N, R26P, R26S

E28N, E28F, E28G, E28L, E28P, E28Y

V30P, V30C, V30A, V30E, V30F, V30G, V30H, V30K, V30N, V30Q, V30R, V30W, V30Y, V30L

Y34A

Y42A, Y42C, Y42D, Y42E, Y42G, Y42I, Y42L, Y42M, Y42Q, Y42S, Y42T, Y42V, Y42W

E58G, E58H

W59S, W59I, W59V, W59D, W59G, W59P

L60M, L60V, L60A, L60C, L60E, L60F, L60Q, L60S, L60T, L60W, L60Y

Y62C, Y62R, Y62G, Y62K, Y62S

V65N, V65L, V65M, V65F, V65W, V65Y

V67L, V67N, V67A, V67C, V67M, V67Q, V67S

T68M, T68F, T68N, T68Q, T68Y

W69M, W69I, W69C, W69E, W69F, W69G, W69K, W69L, W69N, W69Q, W69R, W69S, W69T, W69V

Y75T, Y75G

F85M

F90V

F108T, F108A, F108I, F108K, F108N, F108V

F117L

S199K, S199V

F202W

T273L, T273R, T273G, T273A, T273E, T273F, T273Y, T273D, T273K, T273W, T273H

N276C, N276E, N276K, N276L, N276T, N276V, N276S

Y278L, Y278H, Y278I, Y278K, Y278R, Y278W, Y278C, Y278G, Y278N, Y278Q, Y278S, Y278T, Y278V

Y291W, Y291L, Y291A, Y291C, Y291K, Y291N, Y291Q, Y291R, Y291S, Y291V

S299E

Y310I

As particularly preferred amino acid substitutions, the following amino acid substitutions providing a rate (%), relative to the wild type, of 10% or less were identified.

V6H, V6F, V6G, V6N, V6P, V6R, V6W, V6Y

R26H, R26Y, R26D, R26G, R26N, R26P, R26S

E28F, E28G, E28L, E28P, E28Y

V30C, V30A, V30E, V30F, V30G, V30H, V30K, V30N, V30Q, V30R, V30W, V30Y, V30L

Y34A

Y42A, Y42C, Y42D, Y42E, Y42G, Y42I, Y42L, Y42M, Y42Q, Y42S, Y42T, Y42V, Y42W

W59I, W59V, W59D, W59G, W59P

L60V, L60A, L60C, L60E, L60F, L60Q, L60S, L60T, L60W, L60Y

Y62C, Y62R, Y62G, Y62K, Y62S

V65M, V65F, V65W, V65Y

V67A, V67C, V67M, V67Q, V67S

T68F, T68N, T68Q, T68Y

W69M, W69I, W69C, W69E, W69F, W69G, W69K, W69L, W69N, W69Q, W69R, W69S, W69T, W69V

Y75T, Y75G

F108A, F108I, F108K, F108N, F108V

F117L

F202W

T273F, T273Y, T273D, T273K, T273W, T273H

N276C, N276E, N276K, N276L, N276S, N276T, N276V

Y278K, Y278R, Y278W, Y278C, Y278G, Y278N, Y278Q, Y278S, Y278T, Y278V

Y291L, Y291A, Y291C, Y291K, Y291N, Y291Q, Y291R, Y291S, Y291V

S299E

FIG. 2 shows the evaluation results of the heat resistance. The following amino acid substitutions (34) to (45) providing a rate (%), relative to the wild type, of 110% or more were determined to be effective.

(34) An amino acid substitution in which the mutation point is D3, and the amino acid after substitution is Q, P, E, S or Y

(35) An amino acid substitution in which the mutation point is R26, and the amino acid after substitution is V

(36) An amino acid substitution in which the mutation point is Y34, and the amino acid after substitution is W

(37) An amino acid substitution in which the mutation point is V67, and the amino acid after substitution is H

(38) An amino acid substitution in which the mutation point is T68, and the amino acid after substitution is V or I

(39) An amino acid substitution in which the mutation point is Q74, and the amino acid after substitution is F

(40) An amino acid substitution in which the mutation point is T77, and the amino acid after substitution is Q

(41) An amino acid substitution in which the mutation point is S199, and the amino acid after substitution is C or Q

(42) An amino acid substitution in which the mutation point is T273, and the amino acid after substitution is Q

(43) An amino acid substitution in which the mutation point is S284, and the amino acid after substitution is L, H, K, P or R

(44) An amino acid substitution in which the mutation point is S299, and the amino acid after substitution is N

(45) An amino acid substitution in which the mutation point is S303, and the amino acid after substitution is K As more preferred amino acid substitutions, the following amino acid substitutions providing a rate (%), relative to the wild type, of 120% or more were identified.

D3P, D3E, D3S, D3Y

R26V

Y34W

V67H

T77Q

S199C, S199Q

T273Q

S284H, S284K, S284P, S284R

S303K

As particularly preferred amino acid substitutions, the following amino acid substitutions providing a rate (%), relative to the wild type, of 130% or more were identified.

D3E, D3S, D3Y

R26V

Y34W

V67H

S199Q

T273Q

S284H, S284K, S284P, S284R 2-2. Evaluation of Oxidation Resistance

Hydrogen peroxide (30 to 35%) (Wako, special grade reagent) is diluted with 200 mM Tris-HCl pH 6.0 to prepare a hydrogen peroxide solution (0.03%) as an oxidizing agent. The mature enzyme is diluted twice with the hydrogen peroxide solution, and then the solution mixture is caused to react at 30° C. for 1 hour. The activity is measured after the reaction, and compared with the activity before the treatment to calculate the residual activity rate.

The residual activity rate and the value relative to the wild type in the case of the hydrogen peroxide treatment are calculated using the following formulas to identify amino acid substitutions effective for improving the oxidation resistance.

Residual activity rate (%)=(enzyme activity after hydrogen peroxide treatment)/(enzyme activity before treatment)×100

Rate (%) relative to wild type=(residual activity rate of mutated enzyme)/(residual activity rate of wild-type enzyme)×100

FIG. 3 shows the evaluation results of the oxidation resistance. The following amino acid substitutions (46) to (59) providing a rate (%), relative to the wild type, of 110% or more were determined to be effective.

(46) An amino acid substitution in which the mutation point is D3, and the amino acid after substitution is E, Q, S or Y

(47) An amino acid substitution in which the mutation point is V6, and the amino acid after substitution is P

(48) An amino acid substitution in which the mutation point is R26, and the amino acid after substitution is M, K, W, C, Q, G, Y, E, T, N, D, I, S, P or V

(49) An amino acid substitution in which the mutation point is E28, and the amino acid after substitution is L, M, K, C, V, R, W, G, N, F, Y or H

(50) An amino acid substitution in which the mutation point is Y42, and the amino acid after substitution is L, N or F

(51) An amino acid substitution in which the mutation point is E58, and the amino acid after substitution is Q, A, I, V, L, T, M, K, Y, W, F or R

(52) An amino acid substitution in which the mutation point is V67, and the amino acid after substitution is T, S or A

(53) An amino acid substitution in which the mutation point is T68, and the amino acid after substitution is L, I, V or M

(54) An amino acid substitution in which the mutation point is Q74, and the amino acid after substitution is V

(55) An amino acid substitution in which the mutation point is T77, and the amino acid after substitution is D

(56) An amino acid substitution in which the mutation point is S199, and the amino acid after substitution is C

(57) An amino acid substitution in which the mutation point is T273, and the amino acid after substitution is E

(58) An amino acid substitution in which the mutation point is S284, and the amino acid after substitution is R or H

(59) An amino acid substitution in which the mutation point is Y291, and the amino acid after substitution is I, S, F, L, C, N, V or M As more preferred amino acid substitutions, the following amino acid substitutions providing a rate (%), relative to the wild type, of 120% or more were identified.

D3S, D3Y

V6P

R26W, R26C, R26Q, R26G, R26Y, R26E, R26T, R26N, R26D, R26I, R26S, R26P, R26V

E28L, E28M, E28K, E28C, E28V, E28R, E28W, E28G, E28N, E28F, E28Y, E28H

E58A, E58I, E58V, E58L, E58T, E58M, E58K, E58Y, E58W, E58F, E58R

V67S, V67A

T68I, T68V, T68M

T273E

S284R, S284H

Y291C, Y291N, Y291V, Y291M

As particularly preferred amino acid substitutions, the following amino acid substitutions providing a rate (%), relative to the wild type, of 130% or more were identified.

V6P

R26C, R26Q, R26G, R26Y, R26E, R26T, R26N, R26D, R26I, R26S, R26P, R26V

E28V, E28R, E28W, E28G, E28N, E28F, E28Y, E28H

Y42F

E58I, E58V, E58L, E58T, E58M, E58K, E58Y, E58W, E58F, E58R

T68I, T68V, T68M

S284H 2-3. Evaluation of Reactivity

The mature enzyme is diluted to an appropriate concentration with 200 mM Tris-HCl pH 6.0 (sample solution), and the activity is measured. The value relative to the wild type was calculated based on the following formula, and amino acid substitutions effective for improving the reactivity were identified.

Rate (%) relative to wild type=(activity of mutated enzyme)/(activity of wild-type enzyme)×100

When the specific activity is determined, the absorbance of the sample solution at 280 nm is measured to calculate the protein concentration, and the specific activity is calculated from the measured activity value and the protein concentration.

FIG. 4 shows the evaluation results of the reactivity. The following amino acid substitutions (60) to (63) providing a rate (%), relative to the wild type, of 110% or more were determined to be effective.

(60) An amino acid substitution in which the mutation point is S284, and the amino acid after substitution is M, K or V

(61) An amino acid substitution in which the mutation point is F251, and the amino acid after substitution is Y

(62) An amino acid substitution in which the mutation point is V6 and Y75, the amino acid after substitution at mutation point V6 is E, and the amino acid after substitution at mutation point Y75 is F

(63) An amino acid substitution in which the mutation points are D3 and T77, the amino acid after substitution at the mutation point D3 is P, and the amino acid after substitution at the mutation point T77 is Q As more preferred amino acid substitutions, the following amino acid substitutions providing a rate (%), relative to the wild type, of 120% or more were identified.

S284V

F251Y

Double variant of V6E and Y75F

Double variant of D3P and T77Q

As particularly preferred amino acid substitutions, the following amino acid substitutions providing a rate (%), relative to the wild type, of 130% or more were identified.

Double variant of V6E and Y75F

Double variant of D3P and T77Q

As shown in FIG. 5, the following amino acid substitutions (64) to (91) resulted in two or more property changes, and were effective for multiple improvements.

(64) An amino acid substitution in which the mutation point is D3, the amino acid after substitution is Q, S or Y, and the property changes due to the amino acid substitution are improvements in heat resistance and oxidation resistance

(65) An amino acid substitution in which the mutation point is D3, the amino acid after substitution is P, and the property changes due to the amino acid substitution are improvements in heat resistance and reactivity

(66) An amino acid substitution in which the mutation point is D3, the amino acid after substitution is E, and the property changes due to the amino acid substitution are improvements in heat resistance, oxidation resistance and reactivity

(67) An amino acid substitution in which the mutation point is V6, the amino acid after substitution is P, and the property changes due to the amino acid substitution are a reduction in temperature stability and an improvement in oxidation resistance

(68) An amino acid substitution in which the mutation point is R26, the amino acid after substitution is K, Q, M, Y, D, G, N, P or S, and the property changes due to the amino acid substitution are a reduction in temperature stability and an improvement in oxidation resistance

(69) An amino acid substitution in which the mutation point is R26, the amino acid after substitution is V, and the property changes due to the amino acid substitution are improvements in heat resistance and oxidation resistance

(70) An amino acid substitution in which the mutation point is R26, the amino acid after substitution is H, and the property changes due to the amino acid substitution are a reduction in temperature stability, and improvements in oxidation resistance and reactivity

(71) an amino acid substitution in which the mutation point is E28, the amino acid after substitution is V, S, R, K, M, N, F, G, L or Y, and the property changes due to the amino acid substitution are a reduction in temperature stability and an improvement in oxidation resistance;

(72) An amino acid substitution in which the mutation point is V30, the amino acid after substitution is P, G, N, R or Y, and the property changes due to the amino acid substitution a reduction in temperature stability and an improvement in reactivity

(73) An amino acid substitution in which the mutation point is Y42, the amino acid after substitution is F, L or M, and the property changes due to the amino acid substitution are a reduction in temperature stability and an improvement in oxidation resistance

(74) An amino acid substitution in which the mutation point is E58, the amino acid after substitution is Y, M, A, F, I, V, R, K, L or Q, and the property changes due to the amino acid substitution are a reduction in temperature stability and an improvement in oxidation resistance

(75) An amino acid substitution in which the mutation point is L60, the amino acid after substitution is I, and the property changes due to the amino acid substitution are a reduction in temperature stability and an improvement in reactivity

(76) An amino acid substitution in which the mutation point is V67, the amino acid after substitution is A or S, and the property changes due to the amino acid substitution are a reduction in temperature stability and an improvement in oxidation resistance

(77) An amino acid substitution in which the mutation point is T68, the amino acid after substitution is C, L or M, and the property changes due to the amino acid substitution are a reduction in temperature stability and an improvement in oxidation resistance

(78) An amino acid substitution in which the mutation point is T68, the amino acid after substitution is V or I, and the property changes due to the amino acid substitution are improvements in heat resistance and oxidation resistance

(79) An amino acid substitution in which the mutation point is Q74, the amino acid after substitution is V, and the property changes due to the amino acid substitution are improvements in oxidation resistance and reactivity

(80) An amino acid substitution in which the mutation point is T77, the amino acid after substitution is C, and the property changes due to the amino acid substitution are a reduction in temperature stability and an improvement in oxidation resistance

(81) An amino acid substitution in which the mutation point is T77, the amino acid after substitution is E, and the property changes due to the amino acid substitution are a reduction in temperature stability and an improvement in reactivity

(82) An amino acid substitution in which the mutation point is T77, the amino acid after substitution is D, and the property changes due to the amino acid substitution are improvements in oxidation resistance and reactivity

(83) An amino acid substitution in which the mutation point is S199, the amino acid after substitution is G, and the property changes due to the amino acid substitution are a reduction in temperature stability and an improvement in reactivity

(84) An amino acid substitution in which the mutation point is S199, the amino acid after substitution is C, and the property changes due to the amino acid substitution are improvements in heat resistance, oxidation resistance and reactivity

(85) An amino acid substitution in which the mutation point is T273, the amino acid after substitution is E, and the property changes due to the amino acid substitution are a reduction in temperature stability and an improvement in oxidation resistance

(86) An amino acid substitution in which the mutation point is S284, the amino acid after substitution is M or F, and the property changes due to the amino acid substitution are a reduction in temperature stability and an improvement in reactivity

(87) An amino acid substitution in which the mutation point is S284, the amino acid after substitution is L or K, and the property changes due to the amino acid substitution are improvements in heat resistance and reactivity

(88) An amino acid substitution in which the mutation point is S284, the amino acid after substitution is H or R, and the property changes due to the amino acid substitution are improvements in heat resistance and oxidation resistance

(89) An amino acid substitution in which the mutation point is Y291, the amino acid after substitution is I, L, C, N, S or V, and the property changes due to the amino acid substitution are a reduction in temperature stability and an improvement in oxidation resistance

(90) An amino acid substitution in which the mutation point is S299, the amino acid after substitution is V, K, M or A, and the property changes due to amino acid substitution are a reduction in temperature stability and an improvement in reactivity

(91) An amino acid substitution in which the mutation point is S303, the amino acid after substitution is K, and the property changes due to the amino acid substitution are improvements in heat resistance and reactivity.

Among the above amino acid substitutions, the following amino acid substitutions are accompanied by two contradictory property changes, i.e., a reduction in temperature stability and an improvement in oxidation resistance. The identification of such amino acid substitutions is an unpredictable result. The modified enzyme having such a characteristic amino acid substitution is expected to be used in food applications that require inactivation of the enzyme at low temperatures.

R26K, R26Q, R26M, R26Y, R26D, R26G, R26N, R26P, R26S

E28V, E28R, E28K, E28M, E28N, E28F, E28G, E28L, E28Y

Y42F, Y42L, Y42M

E58Y, E58M, E58A, E58F, E58I, E58V, E58R, E58K, E58L, E58Q

V67A, V67S

T68C, T68L, T68M

T77C

T273E

Y291I, Y291L, Y291C, Y291N, Y291S, Y291V 2-4. Evaluation of Conversion into Deamidase The deamidation activity and the transglutaminase activity of the mature enzyme were calculated by the following formulas as values relative to the wild type enzyme, and then the degree of change in substrate specificity (i.e., conversion into deamidase) was evaluated based on the deamidation activity (ratio relative to the wild type)/transglutaminase activity (ratio relative to the wild type) to identify amino acid substitutions effective for conversion into deamidase. The deamidation activity was measured by the following method, and the transglutaminase activity was measured by the above-mentioned activity measurement method using the substrate solution (R-1).

$$\text{Deamidation activity(ratio relative to the wild type)} \\ (\%) = \text{(deamidation activity of mutated enzyme)/} \\ \text{(deamidation activity of wild type enzyme)} \times 100$$

$$\text{Transglutaminase activity(ratio relative to the wild} \\ \text{type) (\%)} = \text{(transglutaminase activity of mutated} \\ \text{enzyme)/(transglutaminase activity of wild-type} \\ \text{enzyme)} \times 100$$

<Method for Measuring Deamidation Activity>

The maturated enzyme is diluted to an appropriate concentration with a 200 mM potassium phosphate buffer (pH 7.0) (sample solution). To 20 μL of the sample solution, 80 μL of a substrate solution (1% Z-Gln-Gly, 200 mM potassium phosphate buffer, pH 7.0) is added, and the solution mixture is mixed, and caused to react at 37° C. for 24 hours. Using Ammonia Test Wako (WAKO), 40 μL of a coloring reagent A, 20 μL of a coloring reagent B, and 40 μL of a coloring reagent C are added to 20 μL of the reaction sample, and the mixture is caused to react at 37° C. for 10 minutes. The colored sample (50 μL) and a protein-removing solution (50 μL) are mixed and centrifuged. Then, the supernatant is recovered, and the absorbance at 630 nm is measured.

FIG. 6 shows the evaluation results of the conversion into deamidase. If the deamidation activity/transglutaminase activity value exceeds 1, conversion into deamidase has occurred. The following amino acid substitutions (92) to (134) were determined to be effective.

(92) An amino acid substitution in which the mutation point is R5, and the amino acid after substitution is Q, P, C, M, I, V, Y, F, S, N, T or G

(93) An amino acid substitution in which the mutation point is Y34, and the amino acid after substitution is H or M

(94) An amino acid substitution in which the mutation point is W59, and the amino acid after substitution is K or E

(95) An amino acid substitution in which the mutation point is S61, and the amino acid after substitution is T, V, Y, D, I, L, N, E, M, F, W, Q, P, H or K

(96) An amino acid substitution in which the mutation point is Y62, and the amino acid after substitution is D or P

(97) An amino acid substitution in which the mutation point is G63, and the amino acid after substitution is D, Q, Y, R, K, H, P, M, N, C, F, L, W, T, V or S

(98) An amino acid substitution in which the mutation point is V65, and the amino acid after substitution is C, T or K

(99) An amino acid substitution in which the mutation point is G66, and the amino acid after substitution is W or K (100) An amino acid substitution in which the mutation point is T68, and the amino acid after substitution is P or H (101) An amino acid substitution in which the mutation point is W69, and the amino acid after substitution is Y, D or P (102) An amino acid substitution in which the mutation point is Q74, and the amino acid after substitution is R or P (103) An amino acid substitution in which the mutation point is F85, and the amino acid after substitution is Y, W, L, I, Q, C, T, A, V, S, R, H or N (104) An amino acid substitution in which the mutation point is F108, and the amino acid after substitution is Q, C, E, S or N (105) An amino acid substitution in which the mutation point is F117, and the amino acid after substitution is C, I, W, V, A, G, T or N (106) An amino acid substitution in which the mutation point is Y198, and the amino acid after substitution is F, H, L, S, M or I (107) An amino acid substitution in which the mutation point is S199, and the amino acid after substitution is Q or P (108) An amino acid substitution in which the mutation point is K200, and the amino acid after substitution is Y, M, I, R, L or V (109) An amino acid substitution in which the mutation point is H201, and the amino acid after substitution is K, R, M, L or Q (110) An amino acid substitution in which the mutation point is F202, and the amino acid after substitution is Y, M, H, V or C (111) An amino acid substitution in which the mutation point is W203, and the amino acid after substitution is Y (112) An amino acid substitution in which the mutation point is F223, and the amino acid after substitution is Y, M, L, W, V, H, G or A (113) An amino acid substitution in which the mutation point is R238, and the amino acid after substitution is A, D, V, G, H or S (114) An amino acid substitution in which the mutation point is F251, and the amino acid after substitution is H, N, C, M, R, S, A, T, L, P, G, V or Q (115) An amino acid substitution in which the mutation point is V252, and the amino acid after substitution is M, L, T or C (116) An amino acid substitution in which the mutation point is N253, and the amino acid after substitution is T, V, K, C or R (117) An amino acid substitution in which the mutation point is Y256, and the amino acid after substitution is L, V or I (118) An amino acid substitution in which the mutation point is G257, and the amino acid after substitution is A or C (119) An amino acid substitution in which the mutation point is W258, and the amino acid after substitution is Y, F or N (120) An amino acid substitution in which the mutation point is T273, and the amino acid after substitution is N (121) An amino acid substitution in which the mutation point is G275, and the amino acid after substitution is A, C, S, V, K, I, F, H, R, L, P, Q, Y, N, M or T (122) An amino acid substitution in which the mutation point is N276, and the amino acid after substitution is G, M, Q or H (123) An amino acid substitution in which the mutation point is H277, and the amino acid after substitution is N, S, Q, C, E, K, D, I, R, M, P, L, W, V, Y, G, F or T (124) An amino acid substitution in which the mutation point is Y278, and the amino acid after substitution is P or D (125) An amino acid substitution in which the mutation point is H279, and the amino acid after substitution is N (126) An amino acid substitution in which the mutation point is S284, and the amino acid after substitution is C (127) An amino acid substitution in which the mutation point is M288, and the amino acid after substitution is V, Q or T (128) An amino acid substitution in which the mutation point is V290, and the amino acid after substitution is T, C, L, M, A, S or N (129) An amino acid substitution in which the mutation point is Y291, and the amino acid after substitution is H, T, E or G (130) An amino acid substitution in which the mutation point is W298, and the amino acid after substitution is F, Y, I, L or M (131) An amino acid substitution in which the mutation point is S299, and the amino acid after substitution is N or P (132) An amino acid substitution in which the mutation point is Y302, and the amino acid after substitution is L, H, M, V, C, T, P, S or W (133) An amino acid substitution in which the mutation point is S303, and the amino acid after substitution is I, Q, D, H or E (134) An amino acid substitution in which the mutation point is F305, and the amino acid after substitution is W, H or Y As more preferred amino acid substitutions, the following amino acid substitutions having a deamidation activity/transglutaminase activity value of 1.2 or more were identified.

R5Q, R5P, R5C, R5M, R5I, R5V, R5Y, R5F, R5S, R5N, R5T, R5G

Y34H, Y34M

W59K, W59E

S61T, S61V, S61Y, S61D, S61I, S61L, S61N, S61E, S61M, S61F, S61W, S61Q, S61P, S61H, S61K

Y62D, Y62P

G63D, G63Q, G63Y, G63R, G63K, G63H, G63P, G63M, G63N, G63C, G63F, G63L, G63W, G63T, G63V, G63S

V65C, V65T, V65K

G66W, G66K

T68P, T68H

W69Y, W69D, W69P

Q74R, Q74P

F85Y, F85W, F85L, F85I, F85Q, F85C, F85T, F85A, F85V, F85S, F85R, F85H, F85N

F108Q, F108C, F108E, F108S, F108N

F117C, F117I, F117W, F117V, F117A, F117G, F117T, F117N

Y198F, Y198H, Y198L, Y198S, Y198M, Y198I

S199Q, S199P

K200Y, K200M, K200I, K200R, K200L, K200V

H201K, H201R, H201M, H201L, H201Q

F202Y, F202M, F202H, F202V, F202C

W203Y

F223Y, F223M, F223L, F223W, F223V, F223H, F223G, F223A

R238A, R238D, R238V, R238G, R238H, R238S

F251H, F251N, F251C, F251M, F251R, F251S, F251A, F251T, F251L, F251P, F251G, F251V, F251Q

V252M, V252L, V252T, V252C

N253T, N253V, N253K, N253C, N253R

Y256L, Y256V, Y256I

G257A, G257C

W258Y, W258F, W258N

T273N

G275A, G275C, G275S, G275V, G275K, G275I, G275F, G275H, G275R, G275L, G275P, G275Q, G275Y, G275N, G275M, G275T

N276G, N276M, N276Q, N276H

H277N, H277S, H277Q, H277C, H277E, H277K, H277D, H277I, H277R, H277M, H277P, H277L, H277W, H277V, H277Y, H277G, H277F, H277T

Y278P, Y278D

H279N

S284C

M288V, M288Q, M288T

V290T, V290C, V290L, V290M, V290A, V290S, V290N

Y291H, Y291T, Y291E, Y291G

W298F, W298Y, W298I, W298L, W298M

S299N, S299P

Y302L, Y302H, Y302M, Y302V, Y302C, Y302T, Y302P, Y302S, Y302W

S303I, S303Q, S303D, S303H, S303E

F305W, F305H, F305Y

As further preferred amino acid substitutions, the following amino acid substitutions having a deamidation activity/transglutaminase activity value of 2 or more were identified.

R5Y, R5F, R5S, R5N, R5T, R5G

Y34M

S61T, S61V, S61Y, S61D, S61I, S61L, S61N, S61E, S61M, S61F, S61W, S61Q, S61P, S61H, S61K

Y62P

G63D, G63Q, G63Y, G63R, G63K, G63H, G63P, G63M, G63N, G63C, G63F, G63L, G63W, G63T, G63V, G63S

V65C, V65T, V65K

G66K

T68P, T68H

W69D, W69P

F85L, F85I, F85Q, F85C, F85T, F85A, F85V, F85S, F85R, F85H, F85N

F108C, F108E, F108S, F108N

F117C, F117I, F117W, F117V, F117A, F117G, F117T, F117N

Y198L, Y198S, Y198M, Y198I

S199Q, S199P

K200Y, K200M, K200I, K200R, K200L, K200V

H201K, H201R, H201M, H201L, H201Q

F202M, F202H, F202V, F202C

W203Y

F223M, F223L, F223W, F223V, F223H, F223G, F223A

R238H, R238S

F251N, F251C, F251M, F251R, F251S, F251A, F251T, F251L, F251P, F251G, F251V, F251Q

V252L, V252T, V252C

N253T, N253V, N253K, N253C, N253R

Y256L, Y256V, Y256I

G257A, G257C

W258Y, W258F, W258N

T273N

G275C, G275S, G275V, G275K, G275I, G275F, G275H, G275R, G275L, G275P, G275Q, G275Y, G275N, G275M, G275T

N276G, N276M, N276Q, N276H

H277S, H277Q, H277C, H277E, H277K, H277D, H277I, H277R, H277M, H277P, H277L, H277W, H277V, H277Y, H277G, H277F, H277T

Y278P, Y278D

M288Q, M288T

V290M, V290A, V290S, V290N

Y291T, Y291E, Y291G

W298F, W298Y, W298I, W298L, W298M

S299P

Y302L, Y302H, Y302M, Y302V, Y302C, Y302T, Y302P, Y302S, Y302W

F305H, F305Y

As particularly preferred amino acid substitutions, the following amino acid substitutions having a deamidation activity/transglutaminase activity value of 10 or more were identified.

S61Y, S61D, S61I, S61L, S61N, S61E, S61M, S61F, S61W, S61Q, S61P, S61H, S61K

Y62P

G63D, G63Q, G63Y, G63R, G63K, G63H, G63P, G63M, G63N, G63C, G63F, G63L, G63W, G63T, G63V, G63S

V65T, V65K

G66K

T68P, T68H

W69D, W69P

F85H, F85N

F117G, F117T, F117N

Y198S, Y198M, Y198I

S199P

K200M, K200I, K200R, K200L, K200V

H201M, H201L, H201Q

F202V, F202C

W203Y

F223W, F223V, F223H, F223G, F223A

F251L, F251P, F251G, F251V, F251Q

N253T, N253V, N253K, N253C, N253R

Y256L, Y256V, Y256I

G257C

W258N

G275V, G275K, G275I, G275F, G275H, G275R, G275L, G275P, G275Q, G275Y, G275N, G275M, G275T

N276G, N276M, N276Q, N276H

H277S, H277Q, H277C, H277E, H277K, H277D, H277I, H277R, H277M, H277P, H277L, H277W, H277V, H277Y, H277G, H277F, H277T

Y278P, Y278D

M288T

V290S, V290N

Y291G

W298Y, W298I, W298L, W298M

F305Y

INDUSTRIAL APPLICABILITY

The modified transglutaminase of the present invention has improved practically important properties and has a high industrial value. Therefore, the modified transglutaminase is also expected to be used not only in existing applications, but also in new applications.

The present invention is not limited to the above description of the embodiments and examples of the present invention at all. Various modifications that can be easily achieved by those skilled in the art without departing from the claims also fall within the scope of the present invention. The contents of the articles, the patent laid-open publications, patent publications, and the like specified herein shall be cited by incorporation in their entity.

[Sequence Listing Free Text]

SEQ ID NO 2: Explanation of artificial sequence: R26N variant

SEQ ID NO: 3: Explanation of artificial sequence: R26Y variant

SEQ ID NO: 4: Explanation of artificial sequence: R26S variant

SEQ ID NO: 5: Explanation of artificial sequence: E28N variant

SEQ ID NO: 6: Explanation of artificial sequence: E28G variant

SEQ ID NO: 7: Explanation of artificial sequence: E28F variant

SEQ ID NO: 8: Explanation of artificial sequence: E28Y variant

SEQ ID NO: 9: Explanation of artificial sequence: E58R variant

SEQ ID NO: 10: Explanation of artificial sequence: E58L variant

SEQ ID NO: 18: Explanation of artificial sequence: R26N variant

SEQ ID NO: 19: Explanation of artificial sequence: R26Y variant

SEQ ID NO: 20: Explanation of artificial sequence: R26S variant

SEQ ID NO: 21: Explanation of artificial sequence: E28N variant

SEQ ID NO: 22: Explanation of artificial sequence: E28G variant

SEQ ID NO: 23: Explanation of artificial sequence: E28F variant

SEQ ID NO: 24: Explanation of artificial sequence: E28Y variant

SEQ ID NO: 25: Explanation of artificial sequence: E58R variant

SEQ ID NO: 26: Explanation of artificial sequence: E58L variant

[Sequence Listing]

---

The invention claimed is:

1. A modified transglutaminase, wherein the modified transglutaminase exhibits a property change corresponding to the an amino acid substitution, the property changes due to the amino acid substitution are a reduction in temperature stability and an improvement in oxidation resistance, the modified transglutaminase has an amino acid sequence comprising the amino acid sequence of SEQ ID NO: 1 with any one of the following amino acid substitutions (1) to (10), or an amino acid sequence showing having 90% or more sequence identity to the amino acid sequence of SEQ ID NO: 1 with the amino acid substitutions (1) to (10), provided that a difference in the amino acid sequence occurs at a portion other than the position of the amino acid substitution:

(1) an amino acid substitution at residue V6, the amino acid after substitution is P;

(2) an amino acid substitution at residue R26, the amino acid after substitution is K, Q, M, Y, D, G, N, P or H;

(3) an amino acid substitution at residue E28, the amino acid after substitution is V, R, K, M, N, F, G, L or Y;

(4) an amino acid substitution at residue Y42, the amino acid after substitution is F, L or M;

(5) an amino acid substitution at residue E58, the amino acid after substitution is Y, M, A, F, I, V, R, K, L or Q;

(6) an amino acid substitution at residue V67, the amino acid after substitution is A or S;

(7) an amino acid substitution at residue T68, the amino acid after substitution is C, L or M;

(8) an amino acid substitution at residue T77, the amino acid after substitution is C;

(9) an amino substitution at residue T273, the amino acid after substitution is E; and

(10) an amino acid substitution at residue Y291, the amino acid after substitution is I, L, C, N, S or V.

2. A gene encoding the modified transglutaminase according to claim 1.

3. The gene according to claim 2, comprising a base the nucleotide sequence of any one of SEQ ID NOs: 18, 19 and 21 to 26.

4. A recombinant DNA comprising the gene according to claim 2.

5. A microorganism possessing comprising the recombinant DNA according to claim 4.

6. An enzyme preparation comprising the modified transglutaminase according to claim 1, and at least one of an excipient, a buffer, a suspending agent, a stabilizer, a preservative, an antiseptic, physiological saline, various proteins, degradation products of various proteins, various extracts, various salts, various antioxidants, cysteine, glutathione, sodium glutamate, sodium inosinate, sodium guanylate, calcined shell calcium, and silicon dioxide.

7. A method for preparing a modified transglutaminase, comprising the following steps (I) to (III):

(I) providing a nucleic acid sequence encoding the amino acid sequence of the modified transglutaminase according to claim 1;

(II) expressing translating the nucleic acid sequence to express an expression product, and (III) recovering an the expression product.

8. The method according to claim 7, wherein the amino acid sequence is an the amino acid sequence of any one of SEQ ID NOs: 2, 3, and 5 to 10.

9. The method according to claim 8, wherein the nucleic acid sequence comprises a base the nucleic acid sequence of any one of SEQ ID NOs: 18, 19 and 21 to 26.

* * * * *

SEQUENCE LISTING

```
Sequence total quantity: 30
SEQ ID NO: 1           moltype = AA   length = 331
FEATURE                Location/Qualifiers
source                 1..331
                       mol_type = protein
                       organism = Streptomyces mobaraensis
SEQUENCE: 1
DSDDRVTPPA EPLDRMPDPY RPSYGRAETV VNNYIRKWQQ VYSHRDGRKQ QMTEEQREWL  60
SYGCVGVTWV NSGQYPTNRL AFASFDEDRF KNELKNGRPR SGETRAEFEG RVAKESFDEE  120
KGFQRAREVA SVMNRALENA HDESAYLDNL KKELANGNDA LRNEDARSPF YSALRNTPSF  180
```

```
KERNGGNHDP SRMKAVIYSK HFWSGQDRSS SADKRKYGDP DAFRPAPGTG LVDMSRDRNI  240
PRSPTSPGEG FVNFDYGWFG AQTEADADKT VWTHGNHYHA PNGSLGAMHV YESKFRNWSE  300
GYSDFDRGAY VITFIPKSWN TAPDKVKQGW P                                331

SEQ ID NO: 2            moltype = AA   length = 331
FEATURE                 Location/Qualifiers
REGION                  1..331
                        note = R26N mutant
source                  1..331
                        mol_type = protein
                        organism = synthetic construct
SEQUENCE: 2
DSDDRVTPPA EPLDRMPDPY RPSYGNAETV VNNYIRKWQQ VYSHRDGRKQ QMTEEQREWL  60
SYGCVGVTWV NSGQYPTNRL AFASFDEDRF KNELKNGRPR SGETRAEFEG RVAKESFDEE  120
KGFQRAREVA SVMNRALENA HDESAYLDNL KKELANGNDA LRNEDARSPF YSALRNTPSF  180
KERNGGNHDP SRMKAVIYSK HFWSGQDRSS SADKRKYGDP DAFRPAPGTG LVDMSRDRNI  240
PRSPTSPGEG FVNFDYGWFG AQTEADADKT VWTHGNHYHA PNGSLGAMHV YESKFRNWSE  300
GYSDFDRGAY VITFIPKSWN TAPDKVKQGW P                                331

SEQ ID NO: 3            moltype = AA   length = 331
FEATURE                 Location/Qualifiers
REGION                  1..331
                        note = R26Y mutant
source                  1..331
                        mol_type = protein
                        organism = synthetic construct
SEQUENCE: 3
DSDDRVTPPA EPLDRMPDPY RPSYGYAETV VNNYIRKWQQ VYSHRDGRKQ QMTEEQREWL  60
SYGCVGVTWV NSGQYPTNRL AFASFDEDRF KNELKNGRPR SGETRAEFEG RVAKESFDEE  120
KGFQRAREVA SVMNRALENA HDESAYLDNL KKELANGNDA LRNEDARSPF YSALRNTPSF  180
KERNGGNHDP SRMKAVIYSK HFWSGQDRSS SADKRKYGDP DAFRPAPGTG LVDMSRDRNI  240
PRSPTSPGEG FVNFDYGWFG AQTEADADKT VWTHGNHYHA PNGSLGAMHV YESKFRNWSE  300
GYSDFDRGAY VITFIPKSWN TAPDKVKQGW P                                331

SEQ ID NO: 4            moltype = AA   length = 331
FEATURE                 Location/Qualifiers
REGION                  1..331
                        note = R26S mutant
source                  1..331
                        mol_type = protein
                        organism = synthetic construct
SEQUENCE: 4
DSDDRVTPPA EPLDRMPDPY RPSYGSAETV VNNYIRKWQQ VYSHRDGRKQ QMTEEQREWL  60
SYGCVGVTWV NSGQYPTNRL AFASFDEDRF KNELKNGRPR SGETRAEFEG RVAKESFDEE  120
KGFQRAREVA SVMNRALENA HDESAYLDNL KKELANGNDA LRNEDARSPF YSALRNTPSF  180
KERNGGNHDP SRMKAVIYSK HFWSGQDRSS SADKRKYGDP DAFRPAPGTG LVDMSRDRNI  240
PRSPTSPGEG FVNFDYGWFG AQTEADADKT VWTHGNHYHA PNGSLGAMHV YESKFRNWSE  300
GYSDFDRGAY VITFIPKSWN TAPDKVKQGW P                                331

SEQ ID NO: 5            moltype = AA   length = 331
FEATURE                 Location/Qualifiers
REGION                  1..331
                        note = E28N mutant
source                  1..331
                        mol_type = protein
                        organism = synthetic construct
SEQUENCE: 5
DSDDRVTPPA EPLDRMPDPY RPSYGRANTV VNNYIRKWQQ VYSHRDGRKQ QMTEEQREWL  60
SYGCVGVTWV NSGQYPTNRL AFASFDEDRF KNELKNGRPR SGETRAEFEG RVAKESFDEE  120
KGFQRAREVA SVMNRALENA HDESAYLDNL KKELANGNDA LRNEDARSPF YSALRNTPSF  180
KERNGGNHDP SRMKAVIYSK HFWSGQDRSS SADKRKYGDP DAFRPAPGTG LVDMSRDRNI  240
PRSPTSPGEG FVNFDYGWFG AQTEADADKT VWTHGNHYHA PNGSLGAMHV YESKFRNWSE  300
GYSDFDRGAY VITFIPKSWN TAPDKVKQGW P                                331

SEQ ID NO: 6            moltype = AA   length = 331
FEATURE                 Location/Qualifiers
REGION                  1..331
                        note = E28G mutant
source                  1..331
                        mol_type = protein
                        organism = synthetic construct
SEQUENCE: 6
DSDDRVTPPA EPLDRMPDPY RPSYGRAGTV VNNYIRKWQQ VYSHRDGRKQ QMTEEQREWL  60
SYGCVGVTWV NSGQYPTNRL AFASFDEDRF KNELKNGRPR SGETRAEFEG RVAKESFDEE  120
KGFQRAREVA SVMNRALENA HDESAYLDNL KKELANGNDA LRNEDARSPF YSALRNTPSF  180
KERNGGNHDP SRMKAVIYSK HFWSGQDRSS SADKRKYGDP DAFRPAPGTG LVDMSRDRNI  240
PRSPTSPGEG FVNFDYGWFG AQTEADADKT VWTHGNHYHA PNGSLGAMHV YESKFRNWSE  300
GYSDFDRGAY VITFIPKSWN TAPDKVKQGW P                                331
```

```
SEQ ID NO: 7            moltype = AA   length = 331
FEATURE                Location/Qualifiers
REGION                 1..331
                       note = E28F mutant
source                 1..331
                       mol_type = protein
                       organism = synthetic construct
SEQUENCE: 7
DSDDRVTPPA EPLDRMPDPY RPSYGRAFTV VNNYIRKWQQ VYSHRDGRKQ QMTEEQREWL    60
SYGCVGVTWV NSGQYPTNRL AFASFDEDRF KNELKNGRPR SGETRAEFEG RVAKESFDEE   120
KGFQRAREVA SVMNRALENA HDESAYLDNL KKELANGNDA LRNEDARSPF YSALRNTPSF   180
KERNGGNHDP SRMKAVIYSK HFWSGQDRSS SADKRKYGDP DAFRPAPGTG LVDMSRDRNI   240
PRSPTSPGEG FVNFDYGWFG AQTEADADKT VWTHGNHYHA PNGSLGAMHV YESKFRNWSE   300
GYSDFDRGAY VITFIPKSWN TAPDKVKQGW P                                 331

SEQ ID NO: 8            moltype = AA   length = 331
FEATURE                Location/Qualifiers
REGION                 1..331
                       note = E28Y mutant
source                 1..331
                       mol_type = protein
                       organism = synthetic construct
SEQUENCE: 8
DSDDRVTPPA EPLDRMPDPY RPSYGRAYTV VNNYIRKWQQ VYSHRDGRKQ QMTEEQREWL    60
SYGCVGVTWV NSGQYPTNRL AFASFDEDRF KNELKNGRPR SGETRAEFEG RVAKESFDEE   120
KGFQRAREVA SVMNRALENA HDESAYLDNL KKELANGNDA LRNEDARSPF YSALRNTPSF   180
KERNGGNHDP SRMKAVIYSK HFWSGQDRSS SADKRKYGDP DAFRPAPGTG LVDMSRDRNI   240
PRSPTSPGEG FVNFDYGWFG AQTEADADKT VWTHGNHYHA PNGSLGAMHV YESKFRNWSE   300
GYSDFDRGAY VITFIPKSWN TAPDKVKQGW P                                 331

SEQ ID NO: 9            moltype = AA   length = 331
FEATURE                Location/Qualifiers
REGION                 1..331
                       note = E58R mutant
source                 1..331
                       mol_type = protein
                       organism = synthetic construct
SEQUENCE: 9
DSDDRVTPPA EPLDRMPDPY RPSYGRAETV VNNYIRKWQQ VYSHRDGRKQ QMTEEQRRWL    60
SYGCVGVTWV NSGQYPTNRL AFASFDEDRF KNELKNGRPR SGETRAEFEG RVAKESFDEE   120
KGFQRAREVA SVMNRALENA HDESAYLDNL KKELANGNDA LRNEDARSPF YSALRNTPSF   180
KERNGGNHDP SRMKAVIYSK HFWSGQDRSS SADKRKYGDP DAFRPAPGTG LVDMSRDRNI   240
PRSPTSPGEG FVNFDYGWFG AQTEADADKT VWTHGNHYHA PNGSLGAMHV YESKFRNWSE   300
GYSDFDRGAY VITFIPKSWN TAPDKVKQGW P                                 331

SEQ ID NO: 10           moltype = AA   length = 331
FEATURE                Location/Qualifiers
REGION                 1..331
                       note = E58L mutant
source                 1..331
                       mol_type = protein
                       organism = synthetic construct
SEQUENCE: 10
DSDDRVTPPA EPLDRMPDPY RPSYGRAETV VNNYIRKWQQ VYSHRDGRKQ QMTEEQRLWL    60
SYGCVGVTWV NSGQYPTNRL AFASFDEDRF KNELKNGRPR SGETRAEFEG RVAKESFDEE   120
KGFQRAREVA SVMNRALENA HDESAYLDNL KKELANGNDA LRNEDARSPF YSALRNTPSF   180
KERNGGNHDP SRMKAVIYSK HFWSGQDRSS SADKRKYGDP DAFRPAPGTG LVDMSRDRNI   240
PRSPTSPGEG FVNFDYGWFG AQTEADADKT VWTHGNHYHA PNGSLGAMHV YESKFRNWSE   300
GYSDFDRGAY VITFIPKSWN TAPDKVKQGW P                                 331

SEQ ID NO: 11           moltype = AA   length = 410
FEATURE                Location/Qualifiers
source                 1..410
                       mol_type = protein
                       organism = Streptomyces mobaraensis
SEQUENCE: 11
MSQRGRTLVF AALGAVMCTT ALMPSAGAAT GSGSGSGTGE EKRSYAETHR LTADDVDDIN    60
ALNESAPAAS SAGPSFRAPD SDERVTPPAE PLDRMPDPYR PSYGRAETIV NNYIRKWQQV   120
YSHRDGRKQQ MTEEQREWLS YGCVGVTWVN SGQYPTNRLA FAFFDEDKYK NELKNGRPRS   180
GETRAEFEGR VAKDSFDEAK GFQRARDVAS VMNKALENAH DEGAYLDNLK KELANGNDAL   240
RNEDARSPFY SALRNTPSFK DRNGGNHDPS KMKAVIYSKH FWSGQDRSGS SDKRKYGDPE   300
AFRPDRGTGL VDMSRDRNIP RSPTSPGESF VNFDYGWFGA QTEADADKTV WTHGNHYHAP   360
NGSLGAMHVY ESKFRNWSDG YSDFDRGAYV VTFVPKSWNT APDKVTQGWP             410

SEQ ID NO: 12           moltype = AA   length = 418
FEATURE                Location/Qualifiers
source                 1..418
                       mol_type = protein
                       organism = Streptomyces albireticuli
```

```
SEQUENCE: 12
MYKRPRFLTF AAAGAVICTA GFTPSVSQAA GGGDVVTKGS YAETHGLTAD DIKNINALNE   60
RAMAVGQPDK PPTETPPSAG PPSRTPDSDD DRETPPAEPL DRMPDAYRAY GGRATTVVNN  120
YIRKWQQVYS HRDGKKQQMT EEQREMLSYG CVGVTWVNSG LYPTNRLAFA SFDENKYKND  180
LTNTSPRPGE TRAEFEGRIA KGSFDERKGF KRARDVASVM NKALENAHDE GTYISNLKAD  240
LTNKNDALLH EDSRSNFYSA LRNTPSFRER DGGNYDPSKM KAVIYSKHFW SGQDQRGSSD  300
KRKYGDAEAF RPDQGTGLVD MSRDRNIPRS PTSPGEGWVN FDYGWFGAQT EADADKTTWT  360
HGDHYHAPNS DLGPMHVHES KFRNWSAGYA DFDRGAYVIT FIPKSWNTAP GKVEQGWP    418

SEQ ID NO: 13           moltype = AA   length = 400
FEATURE                 Location/Qualifiers
source                  1..400
                        mol_type = protein
                        organism = Streptomyces luteireticuli
SEQUENCE: 13
FATVSAVVCT AGLMPSVSQA AGNREGEEKP SYAETHGLTA ADVENINALN ERALTLGRHG   60
ATPSFRAPDS ANVRETPPAE PLDRMPDAYR ARGGRATTVV NNYIRKWQQV YSHLDGKKQQ  120
MTEEQREKLS YGCVGVTWVN SGPYPTNRLA FSFFDEDKYK NDLKNTRPLA GETRAEFEGR  180
IAKASFDEGK GFKRARDVAS IMNKALENAH DEGAYLDKLK TELTNNNDAL LHEDSRSNFY  240
SALRNTPSFK ERDGGNYDPS RMKAVIYSKH FWSGQDQRGS SDKRKYGDPE AFRPDRGTGL  300
VDMSKDRNIP RSPANPGEGW VNFDYGWFGA QTEADADKTI WTHGDHYHAP NGDLGPMHVY  360
ESKFRNWSAG YADFDRGTYM IALIPKSWNT APAKVKQGWP                        400

SEQ ID NO: 14           moltype = AA   length = 418
FEATURE                 Location/Qualifiers
source                  1..418
                        mol_type = protein
                        organism = Streptomyces cinnamoneus
SEQUENCE: 14
MHQRRRLLAF ATVGAFICTA GLTPSVSQAA GSGDGKEKGS YAETHGLTAD DVKNINALNE   60
SALTLGQPGK PPAELPPSAS ASSRAPASDD DRVTPPAEPL DRMPDAYRAY GGRATTVVNN  120
YIRKWQQVYS HRDGKKQQMT EEQREKLSYG CVGVTWVNSG PYPTNKLAFA FFDENKYKND  180
LKNTSPRPGE TRAEFEGRIA KDSFDEGKGF KRARDVASIM NKALENAHDE GTYIDHLKTE  240
LTNKNDALLH EDSRSNFYSA LRNTPSFKER DGGNYDPSKM KAVIYSKHFW SGQDQRGPSD  300
KRKYGDPEAF RPAQGTGLVD MSKDKSIPRS PANPGEGWVN FDYGWFGAQT EADADNTTWT  360
HGDHYHAPNS DLGPMHVHES KFRKWSAGYE DFDRGSYVIT FIPKSWNTAP AAVKQGWP    418

SEQ ID NO: 15           moltype = AA   length = 418
FEATURE                 Location/Qualifiers
source                  1..418
                        mol_type = protein
                        organism = Streptomyces platensis
SEQUENCE: 15
MYKRRSLLAF ATVSAAIFTA GVMPSVSHAA SGGDGETEGS YAETHGLTAE DVKNINALNK   60
RALTAGQPGN SLAELPPSVS ALFRAPDAAD ERVTPPAEPL NRMPDAYRAY GGRATTVVNN  120
YIRKWQQVYS HRDGIQQQMT EEQREKLSYG CVGVTWVNSG PYPTNKLAFA FFDEDKYKSD  180
LENSRPRPNE TQAEFEGRIV KDSFDEGKGF KRARDVASVM NKALDSAHDE GTYIDNLKKE  240
LANKNDALRY EDSRSNFYSA LRNTPSFKER DGGNYDPSKM KAVVYSKHFW SGQDQRGSSD  300
KRKYGDPDAF RPDQGTGLVD MSKDRNIPRS PARPGESWVN FDYGWFGAQT EADADKTIWT  360
HANHYHAPNG GVGPMNVYES KFRNWSAGYA DFDRGTYVIT FIPKSWNTAP AEVKQGWS    418

SEQ ID NO: 16           moltype = AA   length = 418
FEATURE                 Location/Qualifiers
source                  1..418
                        mol_type = protein
                        organism = Streptomyces hygroscopicus
SEQUENCE: 16
MYKRRSLLAF ATVSAAIFTA GVMPSVSHAA SGGDGEREGS YAETHGLTAE DVKNINALNK   60
RALTAGQPGN SLAELPPSVS ALFRAPDAAD ERVTPPAEPL NRMPDAYRAY GGRATTVVNN  120
YIRKWQQVYS HRDGIQQQMT EEQREKLSYG CVGVTWVNSG PYPTNKLAFA FFDEDKYKSD  180
LENSRPRPNE TQAEFEGRIV KDSFDEGKGF KRARDVASIM NKALDSAHDE GTYIDNLKKE  240
LANKNDALRY EDSRSNFYSA LRNTPSFKER DGGNYDPSKM KAVVYSKHFW SGQDQRGSSD  300
KRKYGDPDAF RPDQGTGLVD MSKDRNIPRS PARPGESWVN FDYGWFGAQT EADADKTIWT  360
HANHYHAPNG GVGPMNVYES KFRNWSAGYA DFDRGTYVIT FIPKSWNTAP AEVKQGWS    418

SEQ ID NO: 17           moltype = DNA   length = 1134
FEATURE                 Location/Qualifiers
source                  1..1134
                        mol_type = other DNA
                        organism = Streptomyces mobaraensis
SEQUENCE: 17
atggacaatg gcgcggggga agagacgaag tcctacgccg aaacctaccg cctcacggcg   60
gatgacgtcg cgaacatcaa cgcgctcaac gaaagcgctc cggccgcttc gagcgccggc  120
ccgtcgttcc gggcccccga ctccgacgac agggtcaccc ctccgctcga cggctcgac   180
aggatgcccg acccgtaccg tccctcgtac ggcaggccg agacggtcgt caacaactac  240
atacgcaagt ggcagcaggt ctacagccac cgcgacggca ggaagcagca gatgaccgag  300
gagcagcggg agtggctgtc ctacggctgc gtcggtgtca cctgggtcaa ttcgggtcag  360
tacccgacga acagactggc cttcgcgtcc ttcgacgagg acaggttcaa gaacgagctg  420
aagaacggca ggccccggtc cggcgagacg cgggcggagt cgagggccg cgtcgcgaag  480
```

```
gagagcttcg acgaggagaa gggcttccag cgggcgcgtg aggtggcgtc cgtcatgaac    540
agggccctgg agaacgccca cgacgagagc gcttacctcg acaacctcaa gaaggaactg    600
gcgaacggca acgacgccct gcgcaacgag gacgcccgtt ccccgttcta ctcggcgctg    660
cggaacacgc cgtccttcaa ggagcggaac ggaggcaatc acgacccgtc caggatgaag    720
gccgtcatct actcgaagca cttctggagc ggccaggacc ggtcgagttc ggccgacaag    780
aggaagtacg gcgacccgga cgccttccgc cccgcccocgg gcaccggcct ggtcgacatg    840
tcgagggaca ggaacattcc gcgcagcccc accagcccg gtgagggatt cgtcaatttc    900
gactacggct ggttcggcgc ccagacggaa gcggacgccg acaagaccgt ctggacccac    960
ggaaatcact atcacgcgcc caatggcagc ctgggtgcca tgcatgtcta cgagagcaag   1020
ttccgcaact ggtccgaggg ttactcggac ttcgaccgcg gagcctatgt gatcaccttc   1080
atccccaaga gctggaacac cgcccccgac aaggtaaagc agggctggcc gtga          1134

SEQ ID NO: 18           moltype = DNA  length = 996
FEATURE                 Location/Qualifiers
misc_feature            1..996
                        note = R26N mutant
source                  1..996
                        mol_type = other DNA
                        organism = synthetic construct SEQUENCE: 18
gactccgacg acagggtcac ccctcccgcc gagccgctcg acaggatgcc cgacccgtac    60
cgtccctcgt acggcaacgc cgagacggtc gtcaacaact acatacgcaa gtggcagcag   120
gtctacagcc accgcgacgg caggaagcag cagatgaccg aggagcagcg ggagtggctg   180
tcctacggct gcgtcggtgt cacctgggtc aattcgggtc agtacccgac gaacagactg   240
gccttcgcgt ccttcgacga ggacaggttc aagaacgagc tgaagaacgg caggccccgg   300
tccggcgaga cgcgggcgga gttcgagggc cgcgtcgcga aggagagctt cgacgaggag   360
aagggcttcc agcgggcgcg tgaggtggcg tccgtcatga acagggccct ggagaacgcc   420
cacgacgaga gcgcttacct cgacaacctc aagaaggaac tggcgaacgg caacgacgcc   480
ctgcgcaacg aggacgcccg ttccccgttc tactcggcgc tgcggaacac gccgtccttc   540
aaggagcgga acggaggcaa tcacgacccg tccaggatga aggccgtcat ctactcgaag   600
cacttctgga gcggccagga ccggtcgagt tcggccgaca gagaggaagta cggcgacccg   660
gacgccttcc gccccgcccc gggcaccggc ctggtcgaca tgtcgaggga caggaacatt   720
ccgcgcagcc ccaccagccc cggtgaggga ttcgtcaatt tcgactacgg ctggttcggc   780
gcccagacgg aagcggacgc cgacaagacc gtctggaccc acggaaatca ctatcacgcg   840
cccaatggca gcctgggtgc catgcatgtc tacgagagca gttccgcaa ctggtccgag   900
ggttactcgg acttcgaccg cggagcctat gtgatcacct tcatcoccaa gagctggaac   960
accgcccccg acaaggtaaa gcagggctgg ccgtga                             996

SEQ ID NO: 19           moltype = DNA  length = 996
FEATURE                 Location/Qualifiers
misc_feature            1..996
                        note = R26Y mutant
source                  1..996
                        mol_type = other DNA
                        organism = synthetic construct SEQUENCE: 19
gactccgacg acagggtcac ccctcccgcc gagccgctcg acaggatgcc cgacccgtac    60
cgtccctcgt acggctacgc cgagacggtc gtcaacaact acatacgcaa gtggcagcag   120
gtctacagcc accgcgacgg caggaagcag cagatgaccg aggagcagcg ggagtggctg   180
tcctacggct gcgtcggtgt cacctgggtc aattcgggtc agtacccgac gaacagactg   240
gccttcgcgt ccttcgacga ggacaggttc aagaacgagc tgaagaacgg caggccccgg   300
tccggcgaga cgcgggcgga gttcgagggc cgcgtcgcga aggagagctt cgacgaggag   360
aagggcttcc agcgggcgcg tgaggtggcg tccgtcatga acagggccct ggagaacgcc   420
cacgacgaga gcgcttacct cgacaacctc aagaaggaac tggcgaacgg caacgacgcc   480
ctgcgcaacg aggacgcccg ttccccgttc tactcggcgc tgcggaacac gccgtccttc   540
aaggagcgga acggaggcaa tcacgacccg tccaggatga aggccgtcat ctactcgaag   600
cacttctgga gcggccagga ccggtcgagt tcggccgaca gagaggaagta cggcgacccg   660
gacgccttcc gccccgcccc gggcaccggc ctggtcgaca tgtcgaggga caggaacatt   720
ccgcgcagcc ccaccagccc cggtgaggga ttcgtcaatt tcgactacgg ctggttcggc   780
gcccagacgg aagcggacgc cgacaagacc gtctggaccc acggaaatca ctatcacgcg   840
cccaatggca gcctgggtgc catgcatgtc tacgagagca gttccgcaa ctggtccgag   900
ggttactcgg acttcgaccg cggagcctat gtgatcacct tcatcoccaa gagctggaac   960
accgcccccg acaaggtaaa gcagggctgg ccgtga                             996

SEQ ID NO: 20           moltype = DNA  length = 996
FEATURE                 Location/Qualifiers
misc_feature            1..996
                        note = R26S mutant
source                  1..996
                        mol_type = other DNA
                        organism = synthetic construct SEQUENCE: 20
gactccgacg acagggtcac ccctcccgcc gagccgctcg acaggatgcc cgacccgtac    60
cgtccctcgt acggcagcgc cgagacggtc gtcaacaact acatacgcaa gtggcagcag   120
gtctacagcc accgcgacgg caggaagcag cagatgaccg aggagcagcg ggagtggctg   180
tcctacggct gcgtcggtgt cacctgggtc aattcgggtc agtacccgac gaacagactg   240
gccttcgcgt ccttcgacga ggacaggttc aagaacgagc tgaagaacgg caggccccgg   300
tccggcgaga cgcgggcgga gttcgagggc cgcgtcgcga aggagagctt cgacgaggag   360
aagggcttcc agcgggcgcg tgaggtggcg tccgtcatga acagggccct ggagaacgcc   420
```

-continued

```
cacgacgaga gcgcttacct cgacaacctc aagaaggaac tggcgaacgg caacgacgcc   480
ctgcgcaacg aggacgcccg ttccccgttc tactcggcgc tgcggaacac gccgtccttc   540
aaggagcgga acggaggcaa tcacgacccg tccaggatga aggccgtcat ctactcgaag   600
cacttctgga gcggccagga ccggtcgagt tcggccgaca agaggaagta cggcgacccg   660
gacgccttcc gccccgcccc gggcaccggc ctggtcgaca tgtcgaggga caggaacatt   720
ccgcgcagcc ccaccagccc cggtgaggga ttcgtcaatt tcgactacgg ctggttcggc   780
gcccagacga aagcggacgc cgacaagacc gtctggaccc acggaaatca ctatcacgcg   840
cccaatggca gcctgggtgc catgcatgtc tacgagagca agttccgcaa ctggtccgag   900
ggttactcgg acttcgaccg cggagcctat gtgatcacct tcatccccaa gagctggaac   960
accgcccccg acaaggtaaa gcagggctgg ccgtga                              996
```

```
SEQ ID NO: 21              moltype = DNA   length = 996
FEATURE                    Location/Qualifiers
misc_feature               1..996
                           note = E28N mutant
source                     1..996
                           mol_type = other DNA
                           organism = synthetic construct
SEQUENCE: 21
gactccgacg acagggtcac ccctcccgcc gagccgctcg acaggatgcc cgacccgtac   60
cgtccctcgt acggcagggc caacacggtc gtcaacaact acatacgcaa gtggcagcag   120
gtctacagcc accgcgacgg caggaagcag cagatgaccg aggagcagcg ggagtggctg   180
tcctacggct gcgtcggtgt cacctgggtc aattcgggtc agtacccgac gaacagactg   240
gccttcgcgt ccttcgacga ggacaggttc aagaacgagc tgaagaacgg caggccccgg   300
tccggcgaga cgcggggcgga gttcgagggc gcgtcgcga aggagagctt cgacgaggag   360
aagggcttcc agcgggcgcg tgaggtggcg tccgtcatga acagggccct ggagaacgcc   420
cacgacgaga gcgcttacct cgacaacctc aagaaggaac tggcgaacgg caacgacgcc   480
ctgcgcaacg aggacgcccg ttccccgttc tactcggcgc tgcggaacac gccgtccttc   540
aaggagcgga acggaggcaa tcacgacccg tccaggatga aggccgtcat ctactcgaag   600
cacttctgga gcggccagga ccggtcgagt tcggccgaca agaggaagta cggcgacccg   660
gacgccttcc gccccgcccc gggcaccggc ctggtcgaca tgtcgaggga caggaacatt   720
ccgcgcagcc ccaccagccc cggtgaggga ttcgtcaatt tcgactacgg ctggttcggc   780
gcccagacga aagcggacgc cgacaagacc gtctggaccc acggaaatca ctatcacgcg   840
cccaatggca gcctgggtgc catgcatgtc tacgagagca agttccgcaa ctggtccgag   900
ggttactcgg acttcgaccg cggagcctat gtgatcacct tcatccccaa gagctggaac   960
accgcccccg acaaggtaaa gcagggctgg ccgtga                              996
```

```
SEQ ID NO: 22              moltype = DNA   length = 996
FEATURE                    Location/Qualifiers
misc_feature               1..996
                           note = E28G mutant
source                     1..996
                           mol_type = other DNA
                           organism = synthetic construct
SEQUENCE: 22
gactccgacg acagggtcac ccctcccgcc gagccgctcg acaggatgcc cgacccgtac   60
cgtccctcgt acggcagggc cggcacggtc gtcaacaact acatacgcaa gtggcagcag   120
gtctacagcc accgcgacgg caggaagcag cagatgaccg aggagcagcg ggagtggctg   180
tcctacggct gcgtcggtgt cacctgggtc aattcgggtc agtacccgac gaacagactg   240
gccttcgcgt ccttcgacga ggacaggttc aagaacgagc tgaagaacgg caggccccgg   300
tccggcgaga cgcggggcgga gttcgagggc gcgtcgcga aggagagctt cgacgaggag   360
aagggcttcc agcgggcgcg tgaggtggcg tccgtcatga acagggccct ggagaacgcc   420
cacgacgaga gcgcttacct cgacaacctc aagaaggaac tggcgaacgg caacgacgcc   480
ctgcgcaacg aggacgcccg ttccccgttc tactcggcgc tgcggaacac gccgtccttc   540
aaggagcgga acggaggcaa tcacgacccg tccaggatga aggccgtcat ctactcgaag   600
cacttctgga gcggccagga ccggtcgagt tcggccgaca agaggaagta cggcgacccg   660
gacgccttcc gccccgcccc gggcaccggc ctggtcgaca tgtcgaggga caggaacatt   720
ccgcgcagcc ccaccagccc cggtgaggga ttcgtcaatt tcgactacgg ctggttcggc   780
gcccagacga aagcggacgc cgacaagacc gtctggaccc acggaaatca ctatcacgcg   840
cccaatggca gcctgggtgc catgcatgtc tacgagagca agttccgcaa ctggtccgag   900
ggttactcgg acttcgaccg cggagcctat gtgatcacct tcatccccaa gagctggaac   960
accgcccccg acaaggtaaa gcagggctgg ccgtga                              996
```

```
SEQ ID NO: 23              moltype = DNA   length = 996
FEATURE                    Location/Qualifiers
misc_feature               1..996
                           note = E28F mutant
source                     1..996
                           mol_type = other DNA
                           organism = synthetic construct
SEQUENCE: 23
gactccgacg acagggtcac ccctcccgcc gagccgctcg acaggatgcc cgacccgtac   60
cgtccctcgt acggcagggc cttcacggtc gtcaacaact acatacgcaa gtggcagcag   120
gtctacagcc accgcgacgg caggaagcag cagatgaccg aggagcagcg ggagtggctg   180
tcctacggct gcgtcggtgt cacctgggtc aattcgggtc agtacccgac gaacagactg   240
gccttcgcgt ccttcgacga ggacaggttc aagaacgagc tgaagaacgg caggccccgg   300
tccggcgaga cgcggggcgga gttcgagggc gcgtcgcga aggagagctt cgacgaggag   360
aagggcttcc agcgggcgcg tgaggtggcg tccgtcatga acagggccct ggagaacgcc   420
cacgacgaga gcgcttacct cgacaacctc aagaaggaac tggcgaacgg caacgacgcc   480
```

```
ctgcgcaacg aggacgcccg ttccccgttc tactcggcgc tgcggaacac gccgtccttc    540
aaggagcgga acggaggcaa tcacgacccg tccaggatga aggccgtcat ctactcgaag    600
cacttctgga gcggccagga ccggtcgagt tcggccgaca agaggaagta cggcgacccg    660
gacgccttcc gccccgcccc gggcaccggc ctggtcgaca tgtcgaggga caggaacatt    720
ccgcgcagcc ccaccagccc cggtgaggga ttcgtcaatt tcgactacgg ctggttcggc    780
gcccagacgg aagcggacgc cgacaagacc gtctggaccc acggaaatca ctatcacgcg    840
cccaatggca gcctgggtgc catgcatgtc tacgagagca agttccgcaa ctggtccgag    900
ggttactcgg acttcgaccg cggagcctat gtgatcacct tcatccccaa gagctggaac    960
accgcccccg acaaggtaaa gcagggctgg ccgtga                             996
```

SEQ ID NO: 24                    moltype = DNA   length = 996
FEATURE                          Location/Qualifiers
misc_feature                     1..996
                                 note = E28Y mutant
source                           1..996
                                 mol_type = other DNA
                                 organism = synthetic construct
SEQUENCE: 24

```
gactccgacg acagggtcac ccctcccgcc gagccgctcg acaggatgcc cgacccgtac    60
cgtccctcgt acggcagggc ctacacggtc gtcaacaact acatacgcaa gtggcagcag    120
gtctacagcc accgcgacgg caggaagcag cagatgaccg aggagcagcg ggagtggctg    180
tcctacggct gcgtcggtgt cacctggbtc aattcgggtc agtacccgac gaacagactg    240
gccttcgcgt ccttcgacga ggacaggttc aagaacgagc tgaagaacgg caggccccgg    300
tccggcgaga cgcgggcgga gttcgagggc cgcgtcgcga aggagagctt cgacgaggag    360
aagggcttcc agcgggcgcg tgaggtggcg tccgtcatga cacagggccct ggagaacgcc    420
cacgacgaga gcgcttacct cgacaacctc aagaaggaac tggcgaacgg caacgacgcc    480
ctgcgcaacg aggacgcccg ttccccgttc tactcggcgc tgcggaacac gccgtccttc    540
aaggagcgga acggaggcaa tcacgacccg tccaggatga aggccgtcat ctactcgaag    600
cacttctgga gcggccagga ccggtcgagt tcggccgaca agaggaagta cggcgacccg    660
gacgccttcc gccccgcccc gggcaccggc ctggtcgaca tgtcgaggga caggaacatt    720
ccgcgcagcc ccaccagccc cggtgaggga ttcgtcaatt tcgactacgg ctggttcggc    780
gcccagacgg aagcggacgc cgacaagacc gtctggaccc acggaaatca ctatcacgcg    840
cccaatggca gcctgggtgc catgcatgtc tacgagagca agttccgcaa ctggtccgag    900
ggttactcgg acttcgaccg cggagcctat gtgatcacct tcatccccaa gagctggaac    960
accgcccccg acaaggtaaa gcagggctgg ccgtga                             996
```

SEQ ID NO: 25                    moltype = DNA   length = 996
FEATURE                          Location/Qualifiers
misc_feature                     1..996
                                 note = E58R mutant
source                           1..996
                                 mol_type = other DNA
                                 organism = synthetic construct
SEQUENCE: 25

```
gactccgacg acagggtcac ccctcccgcc gagccgctcg acaggatgcc cgacccgtac    60
cgtccctcgt acggcagggc cgagacggtc gtcaacaact acatacgcaa gtggcagcag    120
gtctacagcc accgcgacgg caggaagcag cagatgaccg aggagcagcg gaggtggctg    180
tcctacggct gcgtcggtgt cacctggbtc aattcgggtc agtacccgac gaacagactg    240
gccttcgcgt ccttcgacga ggacaggttc aagaacgagc tgaagaacgg caggccccgg    300
tccggcgaga cgcgggcgga gttcgagggc cgcgtcgcga aggagagctt cgacgaggag    360
aagggcttcc agcgggcgcg tgaggtggcg tccgtcatga cacagggccct ggagaacgcc    420
cacgacgaga gcgcttacct cgacaacctc aagaaggaac tggcgaacgg caacgacgcc    480
ctgcgcaacg aggacgcccg ttccccgttc tactcggcgc tgcggaacac gccgtccttc    540
aaggagcgga acggaggcaa tcacgacccg tccaggatga aggccgtcat ctactcgaag    600
cacttctgga gcggccagga ccggtcgagt tcggccgaca agaggaagta cggcgacccg    660
gacgccttcc gccccgcccc gggcaccggc ctggtcgaca tgtcgaggga caggaacatt    720
ccgcgcagcc ccaccagccc cggtgaggga ttcgtcaatt tcgactacgg ctggttcggc    780
gcccagacgg aagcggacgc cgacaagacc gtctggaccc acggaaatca ctatcacgcg    840
cccaatggca gcctgggtgc catgcatgtc tacgagagca agttccgcaa ctggtccgag    900
ggttactcgg acttcgaccg cggagcctat gtgatcacct tcatccccaa gagctggaac    960
accgcccccg acaaggtaaa gcagggctgg ccgtga                             996
```

SEQ ID NO: 26                    moltype = DNA   length = 996
FEATURE                          Location/Qualifiers
misc_feature                     1..996
                                 note = E58L mutant
source                           1..996
                                 mol_type = other DNA
                                 organism = synthetic construct
SEQUENCE: 26

```
gactccgacg acagggtcac ccctcccgcc gagccgctcg acaggatgcc cgacccgtac    60
cgtccctcgt acggcagggc cgagacggtc gtcaacaact acatacgcaa gtggcagcag    120
gtctacagcc accgcgacgg caggaagcag cagatgaccg aggagcagcg gctgtggctg    180
tcctacggct gcgtcggtgt cacctggbtc aattcgggtc agtacccgac gaacagactg    240
gccttcgcgt ccttcgacga ggacaggttc aagaacgagc tgaagaacgg caggccccgg    300
tccggcgaga cgcgggcgga gttcgagggc cgcgtcgcga aggagagctt cgacgaggag    360
aagggcttcc agcgggcgcg tgaggtggcg tccgtcatga cacagggccct ggagaacgcc    420
cacgacgaga gcgcttacct cgacaacctc aagaaggaac tggcgaacgg caacgacgcc    480
ctgcgcaacg aggacgcccg ttccccgttc tactcggcgc tgcggaacac gccgtccttc    540
```

-continued

```
aaggagcgga acggaggcaa tcacgacccg tccaggatga aggccgtcat ctactcgaag   600
cacttctgga gcggccagga ccggtcgagt tcggccgaca agaggaagta cggccgacccg  660
gacgccttcc gccccgcccc gggcaccggc ctggtcgaca tgtcgaggga caggaacatt   720
ccgcgcagcc ccaccagccc cggtgaggga ttcgtcaatt tcgactacgg ctggttcggc   780
gcccagacgg aagcggacgc cgacaagacc gtctggaccc acggaaatca ctatcacgcg   840
cccaatggca gcctgggtgc catgcatgtc tacgagagca agttccgcaa ctggtccgag   900
ggttactcgg acttcgaccg cggagcctat gtgatcacct tcatccccaa gagctggaac   960
accgcccccg acaaggtaaa gcagggctgg ccgtga                             996
```

```
SEQ ID NO: 27          moltype = AA   length = 31
FEATURE                Location/Qualifiers
source                 1..31
                       mol_type = protein
                       organism = Streptomyces mobaraensis
SEQUENCE: 27
MRIRRRALVF ATMSAVLCTA GFMPSAGEAA A                                  31

SEQ ID NO: 28          moltype = AA   length = 45
FEATURE                Location/Qualifiers
source                 1..45
                       mol_type = protein
                       organism = Streptomyces mobaraensis
SEQUENCE: 28
DNGAGEETKS YAETYRLTAD DVANINALNE SAPAASSAGP SFRAP                   45

SEQ ID NO: 29          moltype = DNA   length = 93
FEATURE                Location/Qualifiers
source                 1..93
                       mol_type = other DNA
                       organism = Streptomyces mobaraensis
SEQUENCE: 29
atgcgcatac gccggagagc tctcgtcttc gccactatga gtgcggtgtt atgcaccgcc   60
ggattcatgc cgtcggccgg cgaggccgcc gcc                                93

SEQ ID NO: 30          moltype = DNA   length = 135
FEATURE                Location/Qualifiers
source                 1..135
                       mol_type = other DNA
                       organism = Streptomyces mobaraensis
SEQUENCE: 30
gacaatggcg cgggggaaga gacgaagtcc tacgccgaaa cctaccgcct cacggcggat   60
gacgtcgcga acatcaacgc gctcaacgaa agcgctccgg ccgcttcgag cgccggcccg   120
tcgttccggg ccccc                                                   135
```